United States Patent
Wu et al.

(10) Patent No.: US 11,510,990 B2
(45) Date of Patent: Nov. 29, 2022

(54) CONJUGATES OF FUSION PROTEINS OF GLP-1 AND FGF21

(71) Applicant: BEIJING QL BIOPHARMACEUTICAL CO., LTD., Beijing (CN)

(72) Inventors: Xinle Wu, Beijing (CN); Haixia Zou, Beijing (CN); Yuanyuan Zhang, Beijing (CN); Bo Wu, Beijing (CN); Wei Guo, Beijing (CN)

(73) Assignee: BEIJING QL BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/485,424

(22) Filed: Sep. 26, 2021

(65) Prior Publication Data
US 2022/0016254 A1    Jan. 20, 2022

Related U.S. Application Data

(63) Continuation-in-part of application No. PCT/CN2021/070766, filed on Jan. 8, 2021.

(30) Foreign Application Priority Data

Jan. 11, 2020 (WO) ................ PCT/CN2020/071566
Nov. 20, 2020 (WO) ................ PCT/CN2020/130515

(51) Int. Cl.
  *A61K 47/60*    (2017.01)
  *C07K 14/50*    (2006.01)
  *C07K 14/605*   (2006.01)

(52) U.S. Cl.
  CPC .............. *A61K 47/60* (2017.08); *C07K 14/50* (2013.01); *C07K 14/605* (2013.01); *C07K 2319/915* (2013.01)

(58) Field of Classification Search
  CPC combination set(s) only.
  See application file for complete search history.

(56) References Cited

U.S. PATENT DOCUMENTS

| | | | |
|---|---|---|---|
| 5,208,020 A | 5/1993 | Chari et al. |
| 6,191,102 B1 | 2/2001 | DiMarchi et al. |
| 6,441,163 B1 | 8/2002 | Chari et al. |
| 6,444,788 B1 | 9/2002 | Staby |
| 6,583,111 B1 | 6/2003 | DiMarchi et al. |
| 6,737,236 B1 | 5/2004 | Pieken et al. |
| 7,083,970 B2 | 8/2006 | Schultz et al. |
| 7,084,243 B2 | 8/2006 | Glaesner et al. |
| 7,211,557 B2 | 5/2007 | DiMarchi et al. |
| 7,452,966 B2 | 11/2008 | Glaesner et al. |
| 7,498,308 B2 | 3/2009 | Glaesner et al. |
| 7,534,763 B2 | 5/2009 | Qian et al. |
| 7,576,190 B2 | 8/2009 | Glaesner et al. |
| 7,582,607 B2 | 9/2009 | Frye et al. |
| 7,622,445 B2 | 11/2009 | Frye et al. |
| 7,696,172 B2 | 4/2010 | Thomason et al. |
| 7,855,279 B2 | 12/2010 | Schellenberger et al. |
| 8,012,931 B2 | 9/2011 | Cujec et al. |
| 8,273,854 B2 | 9/2012 | Glaesner et al. |
| 8,541,369 B2 | 9/2013 | Dickinson et al. |
| 8,557,769 B2 | 10/2013 | Coskun et al. |
| 8,557,771 B2 | 10/2013 | Fan et al. |
| 8,563,521 B2 | 10/2013 | Skerra et al. |
| 8,673,860 B2 | 3/2014 | Schellenberger et al. |
| 8,809,499 B2 | 8/2014 | Fan et al. |
| 8,883,726 B2 | 11/2014 | Dickinson et al. |
| 8,969,289 B2 | 3/2015 | Gosselin et al. |
| 9,163,227 B2 | 10/2015 | Annathur et al. |
| 9,249,211 B2 | 2/2016 | Schellenberger et al. |
| 9,434,778 B2 | 9/2016 | Morin et al. |
| 9,458,214 B2 | 10/2016 | Boettcher et al. |
| 9,480,753 B2 | 11/2016 | Tagmose et al. |
| 9,498,534 B2 | 11/2016 | Reedtz-Runge et al. |
| 9,655,974 B2 | 5/2017 | Tagmose et al. |
| 9,744,213 B2 | 8/2017 | Wieczorek et al. |
| 9,895,417 B2 | 2/2018 | Wieczorek et al. |
| 10,035,839 B2 | 7/2018 | Baldwin et al. |
| 10,124,039 B2 | 11/2018 | Wieczorek et al. |
| 10,138,291 B2 | 11/2018 | Chhabra et al. |
| 10,172,953 B2 | 1/2019 | Schellenberger et al. |
| 10,407,479 B2 | 9/2019 | Kopec et al. |
| 10,413,590 B2 | 9/2019 | Ling et al. |
| 10,421,798 B2 | 9/2019 | Schellenberger et al. |
| 10,548,953 B2 | 2/2020 | Liu et al. |
| 10,583,174 B2 | 3/2020 | Gobel et al. |
| 10,669,323 B2 | 6/2020 | Boettcher et al. |
| 11,136,364 B2 | 10/2021 | Kim et al. |
| 2002/0081663 A1 | 6/2002 | Conklin |
| 2003/0220243 A1 | 11/2003 | Glaesner et al. |
| 2004/0002442 A1 | 1/2004 | Pan et al. |
| 2004/0259780 A1 | 12/2004 | Glasebrook et al. |
| 2005/0238649 A1 | 10/2005 | Doronina et al. |
| 2006/0003419 A1 | 1/2006 | Pan et al. |
| 2006/0153860 A1 | 7/2006 | Cho et al. |
| 2007/0036806 A1 | 2/2007 | Glaesner et al. |
| 2007/0092940 A1 | 4/2007 | Eigenbrot et al. |
| 2007/0142278 A1 | 6/2007 | Beals et al. |
| 2007/0173452 A1 | 7/2007 | DiMarchi et al. |
| 2007/0253966 A1 | 11/2007 | Glaesner et al. |
| 2007/0265200 A1 | 11/2007 | Glaesner et al. |

(Continued)

FOREIGN PATENT DOCUMENTS

| | | |
|---|---|---|
| CN | 100569798 C | 12/2009 |
| CN | 102361647 A | 2/2012 |

(Continued)

OTHER PUBLICATIONS

Wang et al., "Expanding the Genetic Code of *Escherichia coli*", Science 292: 498-500, Apr. 20, 2001.

(Continued)

*Primary Examiner* — Lianko G Garyu
(74) *Attorney, Agent, or Firm* — Jun He Law Offices P.C.; James J. Zhu

(57) ABSTRACT

The present disclosure provides conjugates of polypeptides comprising GLP-1, polypeptide linker and FGF21. Pharmaceutical compositions comprising the same and methods of treating diseases are also provided.

16 Claims, 23 Drawing Sheets

Specification includes a Sequence Listing.

(56) References Cited

U.S. PATENT DOCUMENTS

| | | |
|---|---|---|
| 2008/0096819 A1 | 4/2008 | Grabstein et al. |
| 2008/0171856 A1 | 7/2008 | Steeves et al. |
| 2009/0092582 A1 | 4/2009 | Bogin et al. |
| 2009/0111742 A1 | 4/2009 | Kharitonenkov et al. |
| 2009/0156478 A1 | 6/2009 | Lau et al. |
| 2009/0176700 A1 | 7/2009 | Knudsen et al. |
| 2010/0216715 A1 | 8/2010 | Tagmose et al. |
| 2010/0317057 A1 | 12/2010 | Lau et al. |
| 2011/0034373 A1 | 2/2011 | Coskun et al. |
| 2011/0213131 A1 | 9/2011 | Christensen et al. |
| 2011/0312881 A1 | 12/2011 | Silverman et al. |
| 2012/0004183 A1 | 1/2012 | Deiters et al. |
| 2012/0129766 A1 | 5/2012 | Boettcher et al. |
| 2012/0172298 A1 | 7/2012 | Andersen et al. |
| 2012/0238496 A1 | 9/2012 | Fan et al. |
| 2012/0277154 A1 | 11/2012 | Fan et al. |
| 2012/0282279 A1 | 11/2012 | Das et al. |
| 2013/0129724 A1 | 5/2013 | Boettcher et al. |
| 2013/0164310 A1 | 6/2013 | Annathur et al. |
| 2013/0190232 A1 | 7/2013 | Tagmose et al. |
| 2013/0203651 A1 | 8/2013 | Sommerfeld et al. |
| 2013/0252884 A1 | 9/2013 | Garibay et al. |
| 2013/0324460 A1 | 12/2013 | Dickinson et al. |
| 2014/0024586 A1 | 1/2014 | Coskun et al. |
| 2014/0056893 A1 | 2/2014 | Coskun et al. |
| 2014/0073563 A1 | 3/2014 | Boscheinen et al. |
| 2014/0142023 A1 | 5/2014 | Sommerfeld et al. |
| 2014/0162949 A1 | 6/2014 | Cleland et al. |
| 2014/0213512 A1 | 7/2014 | Ellison et al. |
| 2014/0243266 A1 | 8/2014 | Ling et al. |
| 2015/0011462 A1 | 1/2015 | Reedtz-Runge et al. |
| 2015/0141335 A1 | 5/2015 | Ma et al. |
| 2015/0231210 A1 | 8/2015 | Sommerfeld et al. |
| 2016/0137711 A1 | 5/2016 | Schellenberger et al. |
| 2016/0158321 A1 | 6/2016 | Cleland et al. |
| 2016/0194371 A1 | 7/2016 | Boscheinen et al. |
| 2016/0279199 A1 | 9/2016 | Sommerfeld et al. |
| 2017/0145464 A1 | 5/2017 | Gosselin et al. |
| 2017/0166621 A1 | 6/2017 | Boettcher et al. |
| 2017/0182122 A1 | 6/2017 | Ling et al. |
| 2017/0182123 A1 | 6/2017 | Ling et al. |
| 2017/0182124 A1 | 6/2017 | Wieczorek et al. |
| 2017/0320927 A1 | 11/2017 | Sauerberg et al. |
| 2018/0125988 A1 | 5/2018 | Yang et al. |
| 2018/0236033 A1 | 8/2018 | Sommerfeld et al. |
| 2018/0280474 A1 | 10/2018 | Xu et al. |
| 2018/0371041 A1 | 12/2018 | Sommerfeld et al. |
| 2019/0085043 A1 | 3/2019 | Boscheinen et al. |
| 2019/0153115 A1 | 5/2019 | Schellenberger et al. |
| 2019/0185533 A1 | 6/2019 | Kopec et al. |
| 2019/0201491 A1 | 7/2019 | Canning et al. |
| 2019/0314452 A1 | 10/2019 | Hong et al. |
| 2020/0024318 A1 | 1/2020 | Kim et al. |
| 2020/0360530 A1 | 11/2020 | DiMarchi et al. |
| 2021/0196794 A1 | 7/2021 | Chen et al. |

FOREIGN PATENT DOCUMENTS

| | | |
|---|---|---|
| CN | 102770538 A | 11/2012 |
| CN | 101993496 B | 6/2013 |
| CN | 104024273 A | 9/2014 |
| CN | 106432510 A | 2/2017 |
| CN | 109836486 A | 6/2019 |
| CN | 110028587 A | 7/2019 |
| CN | 110087671 A | 8/2019 |
| WO | 2010065439 A1 | 6/2010 |
| WO | 2017116207 A1 | 7/2017 |
| WO | 2017220706 A1 | 12/2017 |
| WO | 2018166461 A1 | 9/2018 |

OTHER PUBLICATIONS

Wang and Schultz et al., "An Expanded Eukaryotic Genetic Code", Science 301: 964-967, Aug. 15, 2003.

Dennis et al., "Albumin Binding as a General Strategy for Improving the Pharmacokinetics of Proteins", J. Biol Chem. 277, 38 (2002) 35035-35043.

Brinkley, "A Brief Survey of Methods for Preparing Protein Conjugates with Dyes, Haptens, and Cross-Linking Reagents", Bioconjugate Chem., vol. 3, No. 1, 2-13, 1992.

Means et al., "Chemical Modifications of Proteins: History and Applications", Bioconjugate Chem., vol. 1, No. 1, 2-12,1990.

Carlsson et al., "Protein Thiolation and Reversible Protein-Protein Conjugation N-Succinimidyl 3-(2-Pyridyldithio)Propionate, A New Heterobifunctional Reagent", Blochem. J. (1978) 173, 723-737.

Batzer et al., "Enhanced evolutionary PCR using oligonucleotides with inosine at the 3'-terminus", Nucleic Acids Research (1991), vol. 19, No. 18, 5081.

Ohtsuka et al., "An Alternative Approach to Deoxyoligonucleotides as Hybridization Probes by Insertion of Deoxyinosine at Ambiguous Codon Positions*", J. Biol. Chem. 260: 2605-2608 (1985).

Rossolini et al., "Use of deoxyinosine-containing primers vs degenerate primers for polymerase chain reaction based on ambiguous sequence information", Mol. Cell. Probes 8:91-98 (1994)).

Boettcher,B.R. "Gastric bypass surgery mimetic approaches", Drug Discovery Today, vol. 22, No. 8, May 30, 2017 (May 30, 2017), pp. 1242-1249.

Omar et al., "Fibroblast Growth Factor 21 (FGF21) and Glucagon Like-Peptide 1 Contribute to Diabetes Resistance in Glucagon Receptor Deficient Mice", Diabetes Publish Ahead of Print, published online Sep. 23, 2013, pp. 1-27.

Altschul et al., "Basic Local Alignment Search Tool", J. Mol. Biol., 215:403-410 (1990).

Altschul et al., "Gapped BLAST and PSI-BLAST: a new generation of protein database search programs", Nucleic Acids Research, 1997, vol. 25, No. 17, 3389-3402.

Higgins et al., "Using CLUSTAL for Multiple Sequence Alignments", Methods in Enzymology, 266:383-402 (1996).

Larkin et al., "Clustal W and Clustal X version 2.0", Bioinformatics (Oxford, England), 23(21): 2947-8 (2007).

Tezze et al.,"FGF21 as Modulator of Metabolism in Health and Disease", Front Physiol. 2019, 10:419.

Fisher FM et al., "Understanding the Physiology of FGF21", Annu Rev Physiol, 2016, 78:223-241.

Carter et al., "High Level *Escherichia coli* Expression and Production of a Bivalent Humanized Anitbody Fragment", Bio/Technology 10:163-167 (1992).

Fusion polypeptide

| SEQ ID NO: | Sequence |
|---|---|
| 2 | HGEGTFTSDVSSYLEEQAAKEFIAWLVRGGGGGGSGGGGSGGGGSGGGGSHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGGSQGRSPSYKS |
| 4 | HGEGTFTSDVSSYLEEQAAREFIAWLVRGGGGGGSGGGGSGGGGSGGGGKHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGGSQGRSPSYKS |
| 5 | HGEGTFTSDVSSYLEEQAAREFIAWLVRGGGGGGSGGGGSGGGGSGGGGKHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGKSQGRSPSYAS |
| 6 | HGEGTFTSDVSSYLEEQAAREFIAWLVRGGGGGGSGGGGSGGGGSGGGGSHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGKSQGRSPSYAS |
| 7 | HGEGTFTSDVSSYLEEQAAREFIAWLVRGGGGGGSGGGGSGGGGSGGGGSHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVKPSQGRSPSYAS |
| 8 | HGEGTFTSDVSSYLEEQAAREFIAWLVRGGGGGGSGGGGSGGGGSGGGGSHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGGSQKRSPSYAS |
| 9 | HGEGTFTSDVSSYLEEQAAREFIAWLVRGGGGGGSGGGGSGGGGSGGGGSHPIPDSSPLLQFGGQVRQRYLYTDDAQQTEAHLEIREDGTVGGAADQSPESLLQLRALRPGVIQILGVRTSRFLCQRPDGALYGSLHFDPEACSFRELLLEDGYNVYQSEAHGLPLHLPGQRSPHRDPAPRGPARFLPLPGLPPALPEPPGILAPQPPDVGSSDPLSLVGGSQGRSPSYKS |

Figure 5A

| | |
|---|---|
| 10 | HGEGTFTSDVSSYLEEQAAREFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGKSQGRSPSYES |
| 11 | HGEGTFTSDVSSYLEEQAAREFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVKPSQGRSPSYES |
| 12 | HGEGTFTSDVSSYLEEQAAREFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGGSQKRSPSYES |
| 13 | HGEGTFTSDVSSYLEEQAAREFIAWLVRGGGGAQPGAQPGAQPGAQPGA QPHPIPDSSPLLQFGGQVRQRYLYTDDAQQTEAHLEIREDGTVGGAADQS PESLLQLRALRPGVIQILGVRTSRFLCQRPDGALYGSLHFDPEACSFRELL LEDGYNVYQSEAHGLPLHLPGQRSPHRDPAPRGPARFLPLPGLPPALPEPP GILAPQPPDVGSSDPLSLVGKSQGRSPSYES |
| 14 | HGEGTFTSDVSSYLEEQAAREFIAWLVRGGGGQEPGQEPGQEPGQEPGQ EPHPIPDSSPLLQFGGQVRQRYLYTDDAQQTEAHLEIREDGTVGGAADQS PESLLQLRALRPGVIQILGVRTSRFLCQRPDGALYGSLHFDPEACSFRELL LEDGYNVYQSEAHGLPLHLPGQRSPHRDPAPRGPARFLPLPGLPPALPEPP GILAPQPPDVGSSDPLSLVGKSQGRSPSYES |
| 15 | HGEGTFTSDVSSYLEEQAAREFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGPSQGRSPSYKS |
| 16 | HGEGTFTSDVSSYLEEQAAKEFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGKSQGRSPSYES |
| 17 | HGEGTFTSDVSSYLEEQAAKEFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVKPSQGRSPSYES |
| 18 | HGEGTFTSDVSSYLEEQAAKEFIAWLVRGGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGGSQKRSPSYES |

Figure 5B

| 19 | HGEGTFTSDVSSYLEEQAAREFIAWLVRGGGGGGGSGGGGSGGGGSGG
GGKHPIPDSSPLLQFGGQVRQRYLYTDDAQQTEAHLEIREDGTVGGAAD
QSPESLLQLRALRPGVIQILGVRTSRFLCQRPDGALYGSLHFDPEACSFRE
LLLEDGYNVYQSEAHGLPLHLPGQRSPHRDPAPRGPARFLPLPGLPPALP
EPPGILAPQPPDVGSSDPLSLVGKSQGRSPSYES |
|---|---|
| 20 | HGEGTFTSDVSSYLEEQAAREFIAWLVRGGGGGGGSGGGGSGGGGSGG
GGKHPIPDSSPLLQFGGQVRQRYLYTDDAQQTEAHLEIREDGTVGGAAD
QSPESLLQLRALRPGVIQILGVRTSRFLCQRPDGALYGSLHFDPEACSFRE
LLLEDGYNVYQSEAHGLPLHLPGQRSPHRDPAPRGPARFLPLPGLPPALP
EPPGILAPQPPDVGSSDPLSLVKPSQGRSPSYES |
| 21 | HGEGTFTSDVSSYLEEQAAREFIAWLVRGGGGGGGSGGGGSGGGGSGG
GGKHPIPDSSPLLQFGGQVRQRYLYTDDAQQTEAHLEIREDGTVGGAAD
QSPESLLQLRALRPGVIQILGVRTSRFLCQRPDGALYGSLHFDPEACSFRE
LLLEDGYNVYQSEAHGLPLHLPGQRSPHRDPAPRGPARFLPLPGLPPALP
EPPGILAPQPPDVGSSDPLSLVGGSQKRSPSYES |
| 22 | HGEGTFTSDVSSYLEEQAAREFIAWLVRGGGGGGGSGGGGSGGGGSGG
GGKHPIPDSSPLLQFGGQVRQRYLYTDDAQQTEAHLEIREDGTVGGAAD
QSPESLLQLRALRPGVIQILGVRTSRFLCQRPDGALYGSLHFDPEACSFRE
LLLEDGYNVYQSEAHGLPLHLPGQRSPHRDPAPRGPARFLPLPGLPPALP
EPPGILAPQPPDVGSSDPLSLVGGSQGRSPSYK |
| 24 | HGEGTFTSDVSSYLEEQAAREFIAWLVRGGGGGGGSGGGGSGGGGSGG
GGKHPIPDSSPLLQFGGQVRQRYLYTDDAQQTEAHLEIREDGTVGGAAD
QSPESLLQLRALRPGVIQILGVRTSRFLCQRPDGALYGSLHFDPEACSFRE
LLLEDGYNVYQSEAHGLPLHLPGQRSPHRDPAPRGPARFLPLPGLPPALP
EPPGILAPQPPDVGSSDPLSLVKGSQGRSPSYES |
| 26 | HGEGTFTSDVSSYLEEQAAREFIAWLVRGGGGGGGKHPIPDSSPLLQFGG
QVRQRYLYTDDAQQTEAHLEIREDGTVGGAADQSPESLLQLRALRPGVI
QILGVRTSRFLCQRPDGALYGSLHFDPEACSFRELLLEDGYNVYQSEAHG
LPLHLPGQRSPHRDPAPRGPARFLPLPGLPPALPEPPGILAPQPPDVGSSDP
LSLVGGSQKRSPSYES |
| 27 | HGEGTFTSDVSSYLEEQAAREFIAWLVRGGGGGGGSGGGGKHPIPDSSPL
LQFGGQVRQRYLYTDDAQQTEAHLEIREDGTVGGAADQSPESLLQLRAL
RPGVIQILGVRTSRFLCQRPDGALYGSLHFDPEACSFRELLLEDGYNVYQ
SEAHGLPLHLPGQRSPHRDPAPRGPARFLPLPGLPPALPEPPGILAPQPPDV
GSSDPLSLVGGSQKRSPSYES |
| 28 | HGEGTFTSDVSSYLEEQAAREFIAWLVRGGGGGGGSGGGGSGGGGSGG
GGSGGGGSGGGGSGGGGSGGGGKHPIPDSSPLLQFGGQVRQRYLYTDD
AQQTEAHLEIREDGTVGGAADQSPESLLQLRALRPGVIQILGVRTSRFLC
QRPDGALYGSLHFDPEACSFRELLLEDGYNVYQSEAHGLPLHLPGQRSPH
RDPAPRGPARFLPLPGLPPALPEPPGILAPQPPDVGSSDPLSLVGGSQKRSP
SYES |

Figure 5C

| | |
|---|---|
| 29 | HGEGTFTSDVSSYLEEQAAREFIAWLVRGGGGAQPGAQPGAQPGAQPGA QPGAQPGAQPGAQPGAQPGAQPGAQPGAQPGAQPGAQPGAQPGA QPGAQPGAQPGAQKHPIPDSSPLLQFGGQVRQRYLYTDDAQQTEAHLEI REDGTVGGAADQSPESLLQLRALRPGVIQILGVRTSRFLCQRPDGALYGS LHFDPEACSFRELLLEDGYNVYQSEAHGLPLHLPGQRSPHRDPAPRGPAR FLPLPGLPPALPEPPGILAPQPPDVGSSDPLSLVGGSQKRSPSYES |
| 30 | HGEGTFTSDVSSYLEEQAAREFIAWLVRGGGGAQPGAQPGAQPGAQPGA QKHPIPDSSPLLQFGGQVRQRYLYTDDAQQTEAHLEIREDGTVGGAADQ SPESLLQLRALRPGVIQILGVRTSRFLCQRPDGALYGSLHFDPEACSFREL LLEDGYNVYQSEAHGLPLHLPGQRSPHRDPAPRGPARFLPLPGLPPALPE PPGILAPQPPDVGSSDPLSLVGGSQKRSPSYES |
| 31 | HGEGTFTSDVSSYLEEQAAREFIAWLVRGGGGAQPGAQPGAQPGAQPGA QPGAQPGAQPGAQPGAQPGAQPGAQKHPIPDSSPLLQFGGQVRQR YLYTDDAQQTEAHLEIREDGTVGGAADQSPESLLQLRALRPGVIQILGVR TSRFLCQRPDGALYGSLHFDPEACSFRELLLEDGYNVYQSEAHGLPLHLP GQRSPHRDPAPRGPARFLPLPGLPPALPEPPGILAPQPPDVGSSDPLSLVGG SQKRSPSYES |
| 32 | HGEGTFTSDVSSYLEEQAAREFIAWLVRGGGGAQPGAQPGAQPGAQPGA QPGAQPGAQPGAQPGAQKHPIPDSSPLLQFGGQVRQRYLYTDDAQ QTEAHLEIREDGTVGGAADQSPESLLQLRALRPGVIQILGVRTSRFLCQRP DGALYGSLHFDPEACSFRELLLEDGYNVYQSEAHGLPLHLPGQRSPHRDP APRGPARFLPLPGLPPALPEPPGILAPQPPDVGSSDPLSLVGGSQKRSPSYE S |
| 33 | HGEGTFTSDVSSYLEEQAAREFIAWLVRGGGGAQPGAQKHPIPDSSPLLQ FGGQVRQRYLYTDDAQQTEAHLEIREDGTVGGAADQSPESLLQLRALRP GVIQILGVRTSRFLCQRPDGALYGSLHFDPEACSFRELLLEDGYNVYQSE AHGLPLHLPGQRSPHRDPAPRGPARFLPLPGLPPALPEPPGILAPQPPDVG SSDPLSLVGGSQKRSPSYES |
| 34 | HGEGTFTSDVSSYLEEQAAREFIAWLVRGGGGAQKHPIPDSSPLLQFGGQ VRQRYLYTDDAQQTEAHLEIREDGTVGGAADQSPESLLQLRALRPGVIQI LGVRTSRFLCQRPDGALYGSLHFDPEACSFRELLLEDGYNVYQSEAHGLP LHLPGQRSPHRDPAPRGPARFLPLPGLPPALPEPPGILAPQPPDVGSSDPLS LVGGSQKRSPSYES |
| 35 | HGEGTFTSDVSSYLEEQAAKEFIAWLVRGGGGGGSGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVKGSQGRSPSYES |
| 77 | HGEGTFTSDVSSYLEEQAAREFIAWLVRGGGGGGKHPIPDSSPLLQFGG QVRQRYLYTDDAQQTEAHLEIREDGTVGGAADQSPESLLQLRALRPGVI QILGVRTSRFLCQRPDGALYGSLHFDPEACSFRELLLEDGYNVYQSEAHG LPLHLPGQRSPHRDPAPRGPARFLPLPGLPPALPEPPGILAPQPPDVGSSDP LSLVGKSQGRSPSYES |

Figure 5D

| | |
|---|---|
| 78 | HGEGTFTSDVSSYLEEQAAREFIAWLVRGGGGGGGSGGGGKHPIPDSSPL LQFGGQVRQRYLYTDDAQQTEAHLEIREDGTVGGAADQSPESLLQLRAL RPGVIQILGVRTSRFLCQRPDGALYGSLHFDPEACSFRELLLEDGYNVYQ SEAHGLPLHLPGQRSPHRDPAPRGPARFLPLPGLPPALPEPPGILAPQPPDV GSSDPLSLVGKSQGRSPSYES |
| 79 | HGEGTFTSDVSSYLEEQAAREFIAWLVRGGGGGGSGGGGSGGGGSGG GGSGGGGSGGGGSGGGGSGGGGKHPIPDSSPLLQFGGQVRQRYLYTDD AQQTEAHLEIREDGTVGGAADQSPESLLQLRALRPGVIQILGVRTSRFLC QRPDGALYGSLHFDPEACSFRELLLEDGYNVYQSEAHGLPLHLPGQRSPH RDPAPRGPARFLPLPGLPPALPEPPGILAPQPPDVGSSDPLSLVGKSQGRSP SYES |
| 80 | HGEGTFTSDVSSYLEEQAAREFIAWLVRGGGGAQPGAQPGAQPGAQPGA QPGAQPGAQPGAQPGAQPGAQPGAQPGAQPGAQPGAQPGAQPGAQPGA QPGAQPGAQPGAQKHPIPDSSPLLQFGGQVRQRYLYTDDAQQTEAHLEI REDGTVGGAADQSPESLLQLRALRPGVIQILGVRTSRFLCQRPDGALYGS LHFDPEACSFRELLLEDGYNVYQSEAHGLPLHLPGQRSPHRDPAPRGPAR FLPLPGLPPALPEPPGILAPQPPDVGSSDPLSLVGKSQGRSPSYES |
| 81 | HGEGTFTSDVSSYLEEQAAREFIAWLVRGGGGAQPGAQPGAQPGAQPGA QPGAQPGAQPGAQPGAQPGAQPGAQPGAQKHPIPDSSPLLQFGGQVRQR YLYTDDAQQTEAHLEIREDGTVGGAADQSPESLLQLRALRPGVIQILGVR TSRFLCQRPDGALYGSLHFDPEACSFRELLLEDGYNVYQSEAHGLPLHLP GQRSPHRDPAPRGPARFLPLPGLPPALPEPPGILAPQPPDVGSSDPLSLVGK SQGRSPSYES |
| 82 | HGEGTFTSDVSSYLEEQAAREFIAWLVRGGGGAQPGAQPGAQPGAQPGA QPGAQPGAQPGAQPGAQPGAQKHPIPDSSPLLQFGGQVRQRYLYTDDAQ QTEAHLEIREDGTVGGAADQSPESLLQLRALRPGVIQILGVRTSRFLCQRP DGALYGSLHFDPEACSFRELLLEDGYNVYQSEAHGLPLHLPGQRSPHRDP APRGPARFLPLPGLPPALPEPPGILAPQPPDVGSSDPLSLVGKSQGRSPSYE S |
| 83 | HGEGTFTSDVSSYLEEQAAREFIAWLVRGGGGAQPGAQKHPIPDSSPLLQ FGGQVRQRYLYTDDAQQTEAHLEIREDGTVGGAADQSPESLLQLRALRP GVIQILGVRTSRFLCQRPDGALYGSLHFDPEACSFRELLLEDGYNVYQSE AHGLPLHLPGQRSPHRDPAPRGPARFLPLPGLPPALPEPPGILAPQPPDVG SSDPLSLVGKSQGRSPSYES |
| 84 | HGEGTFTSDVSSYLEEQAAREFIAWLVRGGGGAQKHPIPDSSPLLQFGGQ VRQRYLYTDDAQQTEAHLEIREDGTVGGAADQSPESLLQLRALRPGVIQI LGVRTSRFLCQRPDGALYGSLHFDPEACSFRELLLEDGYNVYQSEAHGLP LHLPGQRSPHRDPAPRGPARFLPLPGLPPALPEPPGILAPQPPDVGSSDPLS LVGKSQGRSPSYES |
| 85 | HGEGTFTSDVSSYLEEQAAREFIAWLVRGGGGGGSGGGGSGGGGKGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGKSQGRSPSYES |

Figure 5E

| | |
|---|---|
| 86 | HGEGTFTSDVSSYLEEQAAREFIAWLVRGGGGGGGSGGGGKGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGKSQGRSPSYES |
| 87 | HGEGTFTSDVSSYLEEQAAREFIAWLVRGGGGGGGKGGGGSGGGGSGG GGSHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGKSQGRSPSYES |
| 88 | HGEGTFTSDVSSYLEEQAAREFIAWLVRGGGGAQPGAQPGAQPGAQPGA QKHPIPDSSPLLQFGGQVRQRYLYTDDAQQTEAHLEIREDGTVGGAADQ SPESLLQLRALRPGVIQILGVRTSRFLCQRPDGALYGSLHFDPEACSFREL LLEDGYNVYQSEAHGLPLHLPGQRSPHRDPAPRGPARFLPLPGLPPALPE PPGILAPQPPDVGSSDPLSLVGKSQGRSPSYES |
| 116 | HGEGTFTSDVSSYLEEQAAREFIAWLVRGGGGGGGSGGGGSGGGGSGG GGKHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGGSQGRSPSYEK |
| 117 | HGEGTFTSDVSSYLEEQAAREFIAWLVRGGGGGGGSGGGGSGGGGSGG GGKHPIPDSSPLLQFGGQVRQRYLYTDDAQQTEAHLEIREDGTVGGAAD QSPESLLQLRALRPGVIQILGVRTSRFLCQRPDGALYGSLHFDPEACSFRE LLLEDGYNVYQSEAHGLPLHLPGQRSPHRDPAPRGPARFLPLPGLPPALP EPPGILAPQPPDVGSSDPLSLVGGSQGRSPSYESK |
| 148 | HGEGTFTSDVSSYLEEQAAKEFIAWLVRGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGCSQGRSPSYES |
| 149 | HGEGTFTSDVSSYLEEQAAKEFIAWLVRGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQCRSPSYES |
| 150 | HGEGTFTSDVSSYLEEQAAKEFIAWLVRGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQGRSPSYESC |
| 151 | HGEGTFTSDVSSYLEEQAAKEFIAWLVRGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQGRSPSYCS |

Figure 5F

| 152 | HGEGTFTSDVSSYLEEQAAKEFIAWLVRGGGGAQPGAQPGAQPGAQPG
AQCHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGCSQGRSPSYES |
|---|---|
| 153 | HGEGTFTSDVSSYLEEQAAKEFIAWLVRGGGGAQPGAQPGAQPGAQPG
AQCHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGGSQCRSPSYES |
| 154 | HGEGTFTSDVSSYLEEQAAKEFIAWLVRGGGGAQPGAQPGAQPGAQPG
AQCHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGGSQGRSPSYCS |
| 155 | HGEGTFTSDVSSYLEEQAAKEFIAWLVRGGGGAQPGAQPGAQPGAQPG
AQPGAQCHPIPDSSPLLQFGGQVRQRYLYTDDAQQTEAHLEIREDGTVG
GAADQSPESLLQLKALKPGVIQILGVKTSRFLCQRPDGALYGSLHFDPEA
CSFRELLLEDGYNVYQSEAHGLPLHLPGQKSPHRDPAPRGPARFLPLPGL
PPALPEPPGILAPQPPDVGSSDPLSLVGGSQCRSPSYES |
| 156 | HGEGTFTSDVSSYLEEQAAKEFIAWLVRGGGGAQPGAQPGAQPGAQPG
AQPGAQPGAQCHPIPDSSPLLQFGGQVRQRYLYTDDAQQTEAHLEIRED
GTVGGAADQSPESLLQLKALKPGVIQILGVKTSRFLCQRPDGALYGSLHF
DPEACSFRELLLEDGYNVYQSEAHGLPLHLPGQKSPHRDPAPRGPARFLP
LPGLPPALPEPPGILAPQPPDVGSSDPLSLVGGSQCRSPSYES |
| 157 | HGEGTFTSDVSSYLEEQAAKEFIAWLVKGGGGGGSGGGGSGGGGSGG
GGCHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGGSQCRSPSYES |
| 158 | HGEGTFTSDVSSYLEEQAAKEFIAWLVKGGGGGGSGGGGSGGGGCGG
GGSHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGGSQCRSPSYES |
| 159 | HGEGTFTSDVSSYLEEQAAKEFIAWLVKGGGGGGSGGGGCGGGGSGG
GGSHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGGSQCRSPSYES |
| 160 | HGEGTFTSDVSSYLEEQAAKEFIAWLVKGGGGGGSGGGGSGGGGSGG
GGCHPIPDSSPLLQFGGQVRQRYLYTDDAQQTEAHLEIREDGTVGGAAD
QSPESLLQLKALKPGVIQILGVKTSRFLCQRPDGALYGSLHFDPEACSFRE
LLLEDGYNVYQSEAHGLPLHLPGQKSPHRDPAPRGPARFLPLPGLPPALP
EPPGILAPQPPDVGSSDPLSLVGCSQGRSPSYES |

Figure 5G

| 161 | HGEGTFTSDVSSYLEEQAAKEFIAWLVKGGGGGGGSGGGGSGGGGCGG GGSHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGCSQGRSPSYES |
|---|---|
| 162 | HGEGTFTSDVSSYLEEQAAKEFIAWLVKGGGGGGGSGGGGCGGGGSGG GGSHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGCSQGRSPSYES |
| 163 | HGEGTFTSDVSSYLEEQAAKEFIAWLVKGGGGSAPGSPAGSPTGSAPGSP CHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELLL EDGYNVYQSEAHGLPLHLPGQKSPHRDPAPRGPARFLPLPGLPPALPEPP GILAPQPPDVGSSDPLSLVGGSQCRSPSYES |
| 164 | HGEGTFTSDVSSYLEEQAAKEFIAWLVKGGGGGGGSGGGGSGGGGCGG GGSGGGGSGGGGSHPIPDSSPLLQFGGQVRQRYLYTDDAQQTEAHLEIRE DGTVGGAADQSPESLLQLKALKPGVIQILGVKTSRFLCQRPDGALYGSLH FDPEACSFRELLLEDGYNVYQSEAHGLPLHLPGQKSPHRDPAPRGPARFL PLPGLPPALPEPPGILAPQPPDVGSSDPLSLVGGSQCRSPSYES |
| 165 | HGEGTFTSDVSSYLEEQAAKEFIAWLVKGGGGSAPGSPAGSPTGSAPGSP CHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELLL EDGYNVYQSEAHGLPLHLPGQKSPHRDPAPRGPARFLPLPGLPPALPEPP GILAPQPPDVGSSDPLSLVGCSQGRSPSYES |
| 166 | EGTFTSDVSSYLEEQAAKEFIAWLVKGGGGGGGSGGGGSGGGGSGGGG CHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELLL EDGYNVYQSEAHGLPLHLPGQKSPHRDPAPRGPARFLPLPGLPPALPEPP GILAPQPPDVGSSDPLSLVGCSQGRSPSYES |
| 167 | HGEGTFTSDVSSYLEEQAAKEFIAWLVKGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSC |
| 168 | HGEGTFTSDVSSYLEEQAAKEFIAWLVKGGGGAQPGAQPGAQPGAQPG AQPCQAPGAQPGAQPGAQPGAQPGAQPGAQPGAQPGAQPGAQPGAQPG AQPGAQPGAQPGAQPHPIPDSSPLLQFGGQVRQRYLYTDDAQQTEAHLEI REDGTVGGAADQSPESLLQLKALKPGVIQILGVKTSRFLCQRPDGALYGS LHFDPEACSFRELLLEDGYNVYQSEAHGLPLHLPGQKSPHRDPAPRGPAR FLPLPGLPPALPEPPGILAPQPPDVGSSDPLSLVGCSQGRSPSYES |

Figure 5H

| 169 | HGEGTFTSDVSSYLEEQAAKEFIAWLVKGGGGAQPGAQPGAQPGAQPG AQPGAQPGAQPGQCPGAQPGAQPGAQPGAQPGAQPGAQPGAQPGAQPG AQPGAQPGAQPGAQPHPIPDSSPLLQFGGQVRQRYLYTDDAQQTEAHLEI REDGTVGGAADQSPESLLQLKALKPGVIQILGVKTSRFLCQRPDGALYGS LHFDPEACSFRELLLEDGYNVYQSEAHGLPLHLPGQKSPHRDPAPRGPAR FLPLPGLPPALPEPPGILAPQPPDVGSSDPLSLVGCSQGRSPSYES |
|---|---|
| 170 | HGEGTFTSDVSSYLEEQAAKEFIAWLVKGGGGAQPGAQPGQCPGAQPG AQPGAQPGAQPGAQPGAQPGAQPGAQPGAQPGAQPGAQPGAQPGAQPG AQPGAQPGAQPGAQPHPIPDSSPLLQFGGQVRQRYLYTDDAQQTEAHLEI REDGTVGGAADQSPESLLQLKALKPGVIQILGVKTSRFLCQRPDGALYGS LHFDPEACSFRELLLEDGYNVYQSEAHGLPLHLPGQKSPHRDPAPRGPAR FLPLPGLPPALPEPPGILAPQPPDVGSSDPLSLVGCSQGRSPSYES |
| 1 | HGEGTFTSDVSSYLEEQAAKEFIAWLVKGGGGGGGSGGGGSGGGGSGG GGCHPIPDSSPLLQFGGQVRQRYLYTDDAQQTEAHLEIREDGTVGGAAD QSPESLLQLKALKPGVIQILGVKTCRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQGRSPSYES |
| 23 | HGEGTFTSDVSSYLEEQAAKEFIAWLVKGGGGGGGSGGGCSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQGRSPSYES |
| 25 | HGEGTFTSDVSSYLEEQAAKEFIAWLVKGGGGGGGSGGGGSGGGGSGG GGCHPIPDSSPLLQFGGQVRQRYLYTDDAQQTEAHLEIREDGTVGGAAD QSPESLLQLKALKPGVIQILGVKTSRFLCQRPDGALYGSLHFDPEACSFRE LLLEDGYNVYQSEAHGLPLHLPGQKSPHRDPAPRGPARFLPLPGLPPALP EPPGILAPQPPDVGSSDPLSLVGGSQGRSPSYES |
| 76 | HGEGTFTSDVSSYLEEQAAKEFIAWLVKGGGGGGGSGGGGSGGGGSGG GCSGGGGSGGGGSGGGGSGGGGCHPIPDSSPLLQFGGQVRQRYLYTDDA QQTEAHLEIREDGTVGGAADQSPESLLQLKALKPGVIQILGVKTSRFLCQ RPDGALYGSLHFDPEACSFRELLLEDGYNVYQSEAHGLPLHLPGQKSPHR DPAPRGPARFLPLPGLPPALPEPPGILAPQPPDVGSSDPLSLVGGSQGRSPS YES |

Figure 5I

FGF21

| SEQ ID NO: | Sequence |
|---|---|
| 36 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGNKSPHRDPAPRGPARFLPLPGLPPA LPEPPGILAPQPPDVGSSDPLSMVGPSQGRSPSYAS |
| 37 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQGRSPSYKS |
| 38 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGKSQGRSPSYAS |
| 39 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVKPSQGRSPSYAS |
| 40 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQKRSPSYAS |
| 41 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGKSQGRSPSYES |
| 42 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVKPSQGRSPSYES |
| 43 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQKRSPSYES |
| 44 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGPSQGRSPSYKS |
| 45 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQGRSPSYK |

Figure 5J

| | |
|---|---|
| 46 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVKGSQGRSPSYES |
| 118 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQGRSPSYEK |
| 119 | HPIPDSSPLLQFGGQVRQRYLYTDDAQQTEAHLEIREDGTVGGAADQS PESLLQLRALRPGVIQILGVRTSRFLCQRPDGALYGSLHFDPEACSFRE LLLEDGYNVYQSEAHGLPLHLPGQRSPHRDPAPRGPARFLPLPGLPPA LPEPPGILAPQPPDVGSSDPLSLVGGSQGRSPSYESK |
| 135 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSC |
| 136 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGCSQGRSPSYES |
| 137 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGGSQCRSPSYES |
| 138 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGGSQGRSPSYCS |
| 139 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGGSQGRSPSYES |
| 140 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGGSQGRSPSYESC |
| 171 | HPIPDSSPLLQFGGQVRQRYLYTDDAQQTEAHLEIREDGTVGGAADQS PESLLQLKALKPGVIQILGVKTCRFLCQRPDGALYGSLHFDPEACSFRE LLLEDGYNVYQSEAHGLPLHLPGQKSPHRDPAPRGPARFLPLPGLPPA LPEPPGILAPQPPDVGSSDPLSLVGGSQGRSPSYES |

Figure 5K

GLP1

| SEQ ID NO: | GLP-1 |
|---|---|
| 50 | HAEGTFTSDVSSYLEGQAAKEFIAWLVKGRG |
| 51 | X7X8EGTFTSDVSSYLEX22QAAX26X27FIAWLVX34GX36G |
| 52 | HGEGTFTSDVSSYLEEQAAKEFIAWLVRGGG |
| 53 | HGEGTFTSDVSSYLEEQAAREFIAWLVRGGG |
| 115 | HGEGTFTSDVSSYLEEQAAREFIAWLVRGKG |
| 121 | EGTFTSDVSSYLEEQAAKEFIAWLVKGGG |
| 120 | HGEGTFTSDVSSYLEEQAAKEFIAWLVKGGG |

Figure 5L

Polypeptide Linker

| SEQ ID NO: | Linker |
|---|---|
| 54 | GGGGSGGGGSGGGGSGGGGS |
| 55 | GAQPGAQPGAQPGAQPGAQP |
| 56 | GQEPGQEPGQEPGQEPGQEP |
| 57 | GGGGS |
| 58 | GGGGSGGGGS |
| 59 | GGGGSGGGGSGGGGSGGGGSGGGGSGGGGSGGGGSGGGGS |
| 60 | GAQPGAQPGAQPGAQPGAQPGAQPGAQPGAQPGAQPGAQPGAQPGAQPGAQPGAQPGAQPGAQPGAQPGAQPGAQP |
| 62 | GAQPGAQPGAQPGAQPGAQPGAQPGAQPGAQPGAQPGAQPGAQPGAQP |
| 63 | GAQPGAQPGAQPGAQPGAQPGAQPGAQPGAQPGAQPGAQP |
| 64 | GAQPGAQP |
| 65 | GAQP |
| 66 | GGGGSGGGGSGGGGSGGGGK |
| 67 | GGGGK |
| 68 | GGGGSGGGGK |
| 69 | GGGGSGGGGSGGGGSGGGGSGGGGSGGGGSGGGGSGGGGSGGGGK |
| 70 | GAQPGAQPGAQPGAQPGAQPGAQPGAQPGAQPGAQPGAQPGAQPGAQPGAQPGAQPGAQPGAQPGAQPGAQPGAQK |
| 71 | GAQPGAQPGAQPGAQPGAQK |

Figure 5M

| 72 | GAQPGAQPGAQPGAQPGAQPGAQPGAQPGAQPGAQPGAQPGAQPGAQK |
| --- | --- |
| 73 | GAQPGAQPGAQPGAQPGAQPGAQPGAQPGAQPGAQPGAQK |
| 74 | GAQPGAQK |
| 75 | GAQK |
| 89 | GGGGSGGGGSGGGGKGGGGS |
| 90 | GGGGSGGGGKGGGGSGGGGS |
| 91 | GGGGKGGGGSGGGGSGGGGS |
| 109 | GQAPGQAPGQAPGQAPGQAP |
| 110 | GSQPGSQPGSQPGSQPGSQP |
| 111 | GPAQGPAQGPAQGPAQGPAQ |
| 112 | GPQAGPQAGPQAGPQAGPQA |
| 113 | GASPGASPGASPGASPGASP |
| 3 | GPASGPASGPASGPASGPAS |
| 47 | GPSAGPSAGPSAGPSAGPSA |
| 48 | GGGSGGGSGGGSGGGSGGGS |
| 49 | GSGSGSGSGSGSGSGSGSGS |
| 61 | GGGGSGGGGSGGGGSGGGGSGGGGS |
| 141 | GAQPGAQPGAQPGAQPGAQPGAQP |
| 142 | GAQPGAQPGAQPGAQPGAQPGAQPGAQP |
| 143 | GSAPGSPAGSPTGSAPGSPA |
| 144 | GGGGSGGGGSGGGGSGGGGSGGGGSGGGGS |
| 145 | GAQPGAQPGAQPGAQPGAQPGQAPGAQPGAQPGAQPGAQPGAQPGAQPGAQPGAQPGAQPGAQPGAQPGAQPGAQP |
| 146 | GAQPGAQPGAQPGAQPGAQPGAQPGAQPGQAPGAQPGAQPGAQPGAQPGAQPGAQPGAQPGAQPGAQPGAQPGAQP |
| 147 | GAQPGAQPGQAPGAQPGAQPGAQPGAQPGAQPGAQPGAQPGAQPGAQPGAQPGAQPGAQPGAQPGAQPGAQPGAQP |
| 122 | GGGGSGGGGSGGGGSGGGGC |
| 123 | GAQPGAQPGAQPGAQPGAQC |
| 124 | GAQPGAQPGAQPGAQPGAQPGAQC |

Figure 5N

| 125 | GAQPGAQPGAQPGAQPGAQPGAQPGAQC |
| --- | --- |
| 126 | GGGGSGGGGSGGGGCGGGGS |
| 127 | GGGGSGGGGCGGGGSGGGGS |
| 128 | GSAPGSPAGSPTGSAPGSPC |
| 129 | GGGGSGGGGSGGGGCGGGGSGGGGSGGGGS |
| 130 | GAQPGAQPGAQPGAQPGAQPCQAPGAQPGAQPGAQPGAQPGAQPGAQPGAQPGAQPGAQPGAQPGAQPGAQPGAQPGAQP |
| 131 | GAQPGAQPGAQPGAQPGAQPGAQPGAQPGQCPGAQPGAQPGAQPGAQPGAQPGAQPGAQPGAQPGAQPGAQPGAQPGAQP |
| 132 | GAQPGAQPGQCPGAQPGAQPGAQPGAQPGAQPGAQPGAQPGAQPGAQPGAQPGAQPGAQPGAQPGAQPGAQPGAQPGAQP |
| 133 | GGGGSGGGCSGGGGSGGGGC |
| 134 | GGGGSGGGGSGGGGSGGGCSGGGGSGGGGSGGGGSGGGGC |

Figure 5O

Repeating Sequence of Polypeptide Linker

| SEQ ID NO | Sequences |
| --- | --- |
| 92 | GQEP |
| 93 | GEQP |
| 94 | GPQE |
| 95 | GPEQ |
| 96 | GSEP |
| 97 | GESP |
| 98 | GPSE |
| 99 | GPES |
| 100 | GQAP |
| 101 | GPAQ |
| 102 | GPQA |
| 103 | GSQP |
| 104 | GASP |
| 105 | GPAS |
| 106 | GPSA |
| 107 | GGGS |
| 108 | GSGS |
| 57 | GGGGS |
| 65 | GAQP |
| 143 | GSAPGSPAGSPTGSAPGSPA |

Figure 5P

Albumin binding peptide

| SEQ ID NO | Sequences |
|---|---|
| 114 | DICLPRWGCLW |

Figure 5Q

SEQUENCE LISTING

<160> NUMBER OF SEQ ID NOS: 171

<210> SEQ ID NO 1
<211> LENGTH: 232
<212> TYPE: PRT
<213> ORGANISM: Artificial Sequence
<220> FEATURE:
<223> OTHER INFORMATION: Synthetic

<400> SEQUENCE: 1

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
            35                  40                  45

Gly Gly Cys His Pro Ile Pro Asp Ser Ser Pro Leu Leu Gln Phe Gly
 50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Cys Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Gly Ser Gln
            210                 215                 220

Gly Arg Ser Pro Ser Tyr Glu Ser
225                 230

<210> SEQ ID NO 2
<211> LENGTH: 232
<212> TYPE: PRT
<213> ORGANISM: Artificial Sequence
<220> FEATURE:
<223> OTHER INFORMATION: Synthetic

<400> SEQUENCE: 2

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Gly Ser Gly Gly Gly Gly Ser Gly Gly
            35                  40                  45

Gly Gly Ser His Pro Ile Pro Asp Ser Ser Pro Leu Leu Gln Phe Gly
 50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Lys Ser
225                 230

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Gly Pro Ala Ser Gly Pro Ala Ser Gly Pro Ala Ser Gly Pro Ala Ser
1               5                   10                  15

Gly Pro Ala Ser
            20

<210> SEQ ID NO 4
<211> LENGTH: 232
<212> TYPE: PRT
<213> ORGANISM: Artificial Sequence
<220> FEATURE:
<223> OTHER INFORMATION: Synthetic

<400> SEQUENCE: 4

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly Gly Gly
        35                  40                  45

Gly Gly Lys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Lys Ser
225                 230

<210> SEQ ID NO 5
<211> LENGTH: 232
<212> TYPE: PRT
<213> ORGANISM: Artificial Sequence
<220> FEATURE:
<223> OTHER INFORMATION: Synthetic

<400> SEQUENCE: 5

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly
        35                  40                  45

Gly Gly Lys His Pro Ile Pro Asp Ser Ser Pro Leu Leu Gln Phe Gly
    50                  55                  60

Gly Gln Val Arg Gln Arg Tyr Leu Tyr Thr Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Ala Ser
225                 230

<210> SEQ ID NO 6
<211> LENGTH: 232
<212> TYPE: PRT
<213> ORGANISM: Artificial Sequence
<220> FEATURE:
<223> OTHER INFORMATION: Synthetic

<400> SEQUENCE: 6

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly
        35                  40                  45

```
Gly Gly Ser His Pro Ile Pro Asp Ser Ser Pro Leu Leu Gln Phe Gly
 50                  55                  60

Gly Gln Val Arg Gln Arg Tyr Leu Tyr Thr Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Lys Ser Gln
210                 215                 220

Gly Arg Ser Pro Ser Tyr Ala Ser
225                 230

<210> SEQ ID NO 7
<211> LENGTH: 232
<212> TYPE: PRT
<213> ORGANISM: Artificial Sequence
<220> FEATURE:
<223> OTHER INFORMATION: Synthetic

<400> SEQUENCE: 7

His Gly Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Gly Gly Gly
                20                  25                  30

Gly Gly Gly Ser Gly Gly Gly Gly Ser Gly Gly Gly Gly Ser Gly Gly
            35                  40                  45

Gly Gly Ser His Pro Ile Pro Asp Ser Ser Pro Leu Leu Gln Phe Gly
 50                  55                  60

Gly Gln Val Arg Gln Arg Tyr Leu Tyr Thr Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175
```

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Lys Pro Ser Gln
        210                 215                 220

Gly Arg Ser Pro Ser Tyr Ala Ser
225                 230

<210> SEQ ID NO 8
<211> LENGTH: 232
<212> TYPE: PRT
<213> ORGANISM: Artificial Sequence
<220> FEATURE:
<223> OTHER INFORMATION: Synthetic

<400> SEQUENCE: 8

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Gly Ser Gly Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65              70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Lys Arg Ser Pro Ser Tyr Ala Ser
225                 230

<210> SEQ ID NO 9
<211> LENGTH: 232
<212> TYPE: PRT
<213> ORGANISM: Artificial Sequence
<220> FEATURE:
<223> OTHER INFORMATION: Synthetic -continued

<400> SEQUENCE: 9

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Gly Ser Gly Gly Gly Ser Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65              70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Gly Ser Gln
            210                 215                 220

Gly Arg Ser Pro Ser Tyr Lys Ser
225                 230
```

<210> SEQ ID NO 10
<211> LENGTH: 232
<212> TYPE: PRT
<213> ORGANISM: Artificial Sequence
<220> FEATURE:
<223> OTHER INFORMATION: Synthetic

<400> SEQUENCE: 10

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Gly Ser Gly Gly Gly Ser Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65              70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110
```

```
Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Glu Ser
225                 230

<210> SEQ ID NO 11
<211> LENGTH: 232
<212> TYPE: PRT
<213> ORGANISM: Artificial Sequence
<220> FEATURE:
<223> OTHER INFORMATION: Synthetic

<400> SEQUENCE: 11

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Gly Ser Gly Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Lys Pro Ser Gln
    210                 215                 220

Gly Arg Ser Pro Ser Tyr Glu Ser
225                 230
```

<210> SEQ ID NO 12
<211> LENGTH: 232
<212> TYPE: PRT
<213> ORGANISM: Artificial Sequence
<220> FEATURE:
<223> OTHER INFORMATION: Synthetic

<400> SEQUENCE: 12

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Lys Arg Ser Pro Ser Tyr Glu Ser
225                 230
```

<210> SEQ ID NO 13
<211> LENGTH: 232
<212> TYPE: PRT
<213> ORGANISM: Artificial Sequence
<220> FEATURE:
<223> OTHER INFORMATION: Synthetic

<400> SEQUENCE: 13

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80
```

```
Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Glu Ser
225                 230

<210> SEQ ID NO 14
<211> LENGTH: 232
<212> TYPE: PRT
<213> ORGANISM: Artificial Sequence
<220> FEATURE:
<223> OTHER INFORMATION: Synthetic

<400> SEQUENCE: 14

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Gln Glu Pro Gly Gln Glu Pro Gly Gln Glu Pro Gly
        35                  40                  45

Gln Glu Pro His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205
```

Pro Asp Val Gly Ser Ser Asp Pro Leu Ser Leu Val Gly Lys Ser Gln
            210                 215                 220

Gly Arg Ser Pro Ser Tyr Glu Ser
225                 230

<210> SEQ ID NO 15
<211> LENGTH: 232
<212> TYPE: PRT
<213> ORGANISM: Artificial Sequence
<220> FEATURE:
<223> OTHER INFORMATION: Synthetic

<400> SEQUENCE: 15

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Pro Ser Gln
    210                 215                 220

Gly Arg Ser Pro Ser Tyr Lys Ser
225                 230

<210> SEQ ID NO 16
<211> LENGTH: 232
<212> TYPE: PRT
<213> ORGANISM: Artificial Sequence
<220> FEATURE:
<223> OTHER INFORMATION: Synthetic

<400> SEQUENCE: 16

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Ser Gly Gly Gly Ser Gly Gly
            35                  40                  45

```
Gly Gly Ser His Pro Ile Pro Asp Ser Ser Pro Leu Leu Gln Phe Gly
         50                  55                  60

Gly Gln Val Arg Gln Arg Tyr Leu Tyr Thr Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Glu Ser
225                 230

<210> SEQ ID NO 17
<211> LENGTH: 232
<212> TYPE: PRT
<213> ORGANISM: Artificial Sequence
<220> FEATURE:
<223> OTHER INFORMATION: Synthetic

<400> SEQUENCE: 17

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Gly
            20                  25                  30

Gly Gly Gly Ser Gly Gly Gly Ser Gly Gly Gly Gly Ser Gly Gly
        35                  40                  45

Gly Gly Ser His Pro Ile Pro Asp Ser Ser Pro Leu Leu Gln Phe Gly
         50                  55                  60

Gly Gln Val Arg Gln Arg Tyr Leu Tyr Thr Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175
```

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Lys Pro Ser Gln
            210                 215                 220

Gly Arg Ser Pro Ser Tyr Glu Ser
225                 230

<210> SEQ ID NO 18
<211> LENGTH: 232
<212> TYPE: PRT
<213> ORGANISM: Artificial Sequence
<220> FEATURE:
<223> OTHER INFORMATION: Synthetic

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Ser Gly Gly Gly Ser Gly Gly Gly Ser Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Gly Ser Gln
            210                 215                 220

Lys Arg Ser Pro Ser Tyr Glu Ser
225                 230

<210> SEQ ID NO 19
<211> LENGTH: 232
<212> TYPE: PRT
<213> ORGANISM: Artificial Sequence
<220> FEATURE:
<223> OTHER INFORMATION: Synthetic

<400> SEQUENCE: 19

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Glu Ser
225                 230

<210> SEQ ID NO 20
<211> LENGTH: 232
<212> TYPE: PRT
<213> ORGANISM: Artificial Sequence
<220> FEATURE:
<223> OTHER INFORMATION: Synthetic

<400> SEQUENCE: 20

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
                100                 105                 110

```
Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Lys Pro Ser Gln
    210                 215                 220

Gly Arg Ser Pro Ser Tyr Glu Ser
225                 230

<210> SEQ ID NO 21
<211> LENGTH: 232
<212> TYPE: PRT
<213> ORGANISM: Artificial Sequence
<220> FEATURE:
<223> OTHER INFORMATION: Synthetic

<400> SEQUENCE: 21

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Gly Ser Gly Gly Gly Gly Ser Gly Gly
        35                  40                  45

Gly Gly Lys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Lys Arg Ser Pro Ser Tyr Glu Ser
225                 230
```

```
<210> SEQ ID NO 22
<211> LENGTH: 231
<212> TYPE: PRT
<213> ORGANISM: Artificial Sequence
<220> FEATURE:
<223> OTHER INFORMATION: Synthetic

<400> SEQUENCE: 22

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Lys
225                 230

<210> SEQ ID NO 23
<211> LENGTH: 232
<212> TYPE: PRT
<213> ORGANISM: Artificial Sequence
<220> FEATURE:
<223> OTHER INFORMATION: Synthetic

<400> SEQUENCE: 23

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Cys Ser Gly Gly Gly Ser Gly Gly
            35                  40                  45

Gly Gly Cys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80
```

```
Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Gly Ser Gln
            210                 215                 220

Gly Arg Ser Pro Ser Tyr Glu Ser
225                 230

<210> SEQ ID NO 24
<211> LENGTH: 232
<212> TYPE: PRT
<213> ORGANISM: Artificial Sequence
<220> FEATURE:
<223> OTHER INFORMATION: Synthetic

<400> SEQUENCE: 24

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Gly Ser Gly Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65              70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205
```

Pro Asp Val Gly Ser Ser Asp Pro Leu Ser Leu Val Lys Gly Ser Gln
            210                 215                 220

Gly Arg Ser Pro Ser Tyr Glu Ser
225                 230

<210> SEQ ID NO 25
<211> LENGTH: 232
<212> TYPE: PRT
<213> ORGANISM: Artificial Sequence
<220> FEATURE:
<223> OTHER INFORMATION: Synthetic

<400> SEQUENCE: 25

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Glu Ser
225                 230

<210> SEQ ID NO 26
<211> LENGTH: 217
<212> TYPE: PRT
<213> ORGANISM: Artificial Sequence
<220> FEATURE:
<223> OTHER INFORMATION: Synthetic

<400> SEQUENCE: 26

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Lys His Pro Ile Pro Asp Ser Ser Pro Leu Leu Gln Phe
        35                  40                  45

```
Gly Gly Gln Val Arg Gln Arg Tyr Leu Tyr Thr Asp Asp Ala Gln Gln
 50                  55                  60

Thr Glu Ala His Leu Glu Ile Arg Glu Asp Gly Thr Val Gly Gly Ala
 65                  70                  75                  80

Ala Asp Gln Ser Pro Glu Ser Leu Leu Gln Leu Arg Ala Leu Arg Pro
                 85                  90                  95

Gly Val Ile Gln Ile Leu Gly Val Arg Thr Ser Arg Phe Leu Cys Gln
            100                 105                 110

Arg Pro Asp Gly Ala Leu Tyr Gly Ser Leu His Phe Asp Pro Glu Ala
            115                 120                 125

Cys Ser Phe Arg Glu Leu Leu Leu Glu Asp Gly Tyr Asn Val Tyr Gln
130                 135                 140

Ser Glu Ala His Gly Leu Pro Leu His Leu Pro Gly Gln Arg Ser Pro
145                 150                 155                 160

His Arg Asp Pro Ala Pro Arg Gly Pro Ala Arg Phe Leu Pro Leu Pro
                165                 170                 175

Gly Leu Pro Pro Ala Leu Pro Glu Pro Pro Gly Ile Leu Ala Pro Gln
            180                 185                 190

Pro Pro Asp Val Gly Ser Ser Asp Pro Leu Ser Leu Val Gly Gly Ser
            195                 200                 205

Gln Lys Arg Ser Pro Ser Tyr Glu Ser
210                 215

<210> SEQ ID NO 27
<211> LENGTH: 222
<212> TYPE: PRT
<213> ORGANISM: Artificial Sequence
<220> FEATURE:
<223> OTHER INFORMATION: Synthetic

<400> SEQUENCE: 27

His Gly Glu Gly Thr Phe Thr Ser Asp Val Ser Ser Tyr Leu Glu Glu
 1                   5                  10                  15

Gln Ala Ala Arg Glu Phe Ile Ala Trp Leu Val Arg Gly Gly Gly Gly
                 20                  25                  30

Gly Gly Gly Ser Gly Gly Gly Lys His Pro Ile Pro Asp Ser Ser
             35                 40                  45

Pro Leu Leu Gln Phe Gly Gly Gln Val Arg Gln Arg Tyr Leu Tyr Thr
 50                  55                  60

Asp Asp Ala Gln Gln Thr Glu Ala His Leu Glu Ile Arg Glu Asp Gly
 65                  70                  75                  80

Thr Val Gly Gly Ala Ala Asp Gln Ser Pro Glu Ser Leu Leu Gln Leu
                 85                  90                  95

Arg Ala Leu Arg Pro Gly Val Ile Gln Ile Leu Gly Val Arg Thr Ser
            100                 105                 110

Arg Phe Leu Cys Gln Arg Pro Asp Gly Ala Leu Tyr Gly Ser Leu His
            115                 120                 125

Phe Asp Pro Glu Ala Cys Ser Phe Arg Glu Leu Leu Leu Glu Asp Gly
130                 135                 140

Tyr Asn Val Tyr Gln Ser Glu Ala His Gly Leu Pro Leu His Leu Pro
145                 150                 155                 160

Gly Gln Arg Ser Pro His Arg Asp Pro Ala Pro Arg Gly Pro Ala Arg
                165                 170                 175

Phe Leu Pro Leu Pro Gly Leu Pro Pro Ala Leu Pro Glu Pro Pro Gly
            180                 185                 190
```

```
Ile Leu Ala Pro Gln Pro Pro Asp Val Gly Ser Ser Asp Pro Leu Ser
            195                 200                 205

Leu Val Gly Gly Ser Gln Lys Arg Ser Pro Ser Tyr Glu Ser
    210                 215                 220

<210> SEQ ID NO 28
<211> LENGTH: 252
<212> TYPE: PRT
<213> ORGANISM: Artificial Sequence
<220> FEATURE:
<223> OTHER INFORMATION: Synthetic

<400> SEQUENCE: 28

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Ser Gly Gly Gly Ser Gly Gly
        35                  40                  45

Gly Gly Ser Gly Gly Gly Ser Gly Gly Gly Ser Gly Gly Gly
    50                  55                  60

Gly Ser Gly Gly Gly Lys His Pro Ile Pro Asp Ser Ser Pro Leu
65                  70                  75                  80

Leu Gln Phe Gly Gly Gln Val Arg Gln Arg Tyr Leu Tyr Thr Asp Asp
                85                  90                  95

Ala Gln Gln Thr Glu Ala His Leu Glu Ile Arg Glu Asp Gly Thr Val
            100                 105                 110

Gly Gly Ala Ala Asp Gln Ser Pro Glu Ser Leu Leu Gln Leu Arg Ala
        115                 120                 125

Leu Arg Pro Gly Val Ile Gln Ile Leu Gly Val Arg Thr Ser Arg Phe
    130                 135                 140

Leu Cys Gln Arg Pro Asp Gly Ala Leu Tyr Gly Ser Leu His Phe Asp
145                 150                 155                 160

Pro Glu Ala Cys Ser Phe Arg Glu Leu Leu Leu Glu Asp Gly Tyr Asn
                165                 170                 175

Val Tyr Gln Ser Glu Ala His Gly Leu Pro Leu His Leu Pro Gly Gln
            180                 185                 190

Arg Ser Pro His Arg Asp Pro Ala Pro Arg Gly Pro Ala Arg Phe Leu
        195                 200                 205

Pro Leu Pro Gly Leu Pro Pro Ala Leu Pro Glu Pro Pro Gly Ile Leu
    210                 215                 220

Ala Pro Gln Pro Pro Asp Val Gly Ser Ser Asp Pro Leu Ser Leu Val
225                 230                 235                 240

Gly Gly Ser Gln Lys Arg Ser Pro Ser Tyr Glu Ser
                245                 250

<210> SEQ ID NO 29
<211> LENGTH: 292
<212> TYPE: PRT
<213> ORGANISM: Artificial Sequence
<220> FEATURE:
<223> OTHER INFORMATION: Synthetic

<400> SEQUENCE: 29

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30
```

Ala Gln Pro Gly Ala Gln Pro Gly Ala Gln Pro Gly
         35                  40                  45

Ala Gln Pro Gly Ala Gln Pro Gly Ala Gln Pro Gly
 50                  55                  60

Ala Gln Pro Gly Ala Gln Pro Gly Ala Gln Pro Gly
65                  70                  75                  80

Ala Gln Pro Gly Ala Gln Pro Gly Ala Gln Pro Gly
             85                  90                  95

Ala Gln Pro Gly Ala Gln Pro Gly Ala Gln Lys His
            100                 105                 110

Pro Ile Pro Asp Ser Ser Pro Leu Leu Gln Phe Gly Gly Gln Val Arg
            115                 120                 125

Gln Arg Tyr Leu Tyr Thr Asp Asp Ala Gln Gln Thr Glu Ala His Leu
130                 135                 140

Glu Ile Arg Glu Asp Gly Thr Val Gly Gly Ala Ala Asp Gln Ser Pro
145                 150                 155                 160

Glu Ser Leu Leu Gln Leu Arg Ala Leu Arg Pro Gly Val Ile Gln Ile
                165                 170                 175

Leu Gly Val Arg Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
    210                 215                 220

Leu Pro Leu His Leu Pro Gly Gln Arg Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Pro Asp Val Gly
            260                 265                 270

Ser Ser Asp Pro Leu Ser Leu Val Gly Gly Ser Gln Lys Arg Ser Pro
        275                 280                 285

Ser Tyr Glu Ser
    290

<210> SEQ ID NO 30
<211> LENGTH: 232
<212> TYPE: PRT
<213> ORGANISM: Artificial Sequence
<220> FEATURE:
<223> OTHER INFORMATION: Synthetic

<400> SEQUENCE: 30

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Lys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

```
Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
        210                 215                 220

Lys Arg Ser Pro Ser Tyr Glu Ser
225                 230

<210> SEQ ID NO 31
<211> LENGTH: 260
<212> TYPE: PRT
<213> ORGANISM: Artificial Sequence
<220> FEATURE:
<223> OTHER INFORMATION: Synthetic

<400> SEQUENCE: 31

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Ala Gln Pro Gly Ala Gln Lys His
65                  70                  75                  80

Pro Ile Pro Asp Ser Ser Pro Leu Leu Gln Phe Gly Gly Gln Val Arg
                85                  90                  95

Gln Arg Tyr Leu Tyr Thr Asp Asp Ala Gln Gln Thr Glu Ala His Leu
            100                 105                 110

Glu Ile Arg Glu Asp Gly Thr Val Gly Gly Ala Ala Asp Gln Ser Pro
        115                 120                 125

Glu Ser Leu Leu Gln Leu Arg Ala Leu Arg Pro Gly Val Ile Gln Ile
    130                 135                 140

Leu Gly Val Arg Thr Ser Arg Phe Leu Cys Gln Arg Pro Asp Gly Ala
145                 150                 155                 160

Leu Tyr Gly Ser Leu His Phe Asp Pro Glu Ala Cys Ser Phe Arg Glu
                165                 170                 175

Leu Leu Leu Glu Asp Gly Tyr Asn Val Tyr Gln Ser Glu Ala His Gly
            180                 185                 190

Leu Pro Leu His Leu Pro Gly Gln Arg Ser Pro His Arg Asp Pro Ala
        195                 200                 205

Pro Arg Gly Pro Ala Arg Phe Leu Pro Leu Pro Gly Leu Pro Pro Ala
    210                 215                 220
```

```
Leu Pro Glu Pro Pro Gly Ile Leu Ala Pro Gln Pro Asp Val Gly
225                 230                 235                 240

Ser Ser Asp Pro Leu Ser Leu Val Gly Ser Gln Lys Arg Ser Pro
            245                 250                 255

Ser Tyr Glu Ser
            260
```

<210> SEQ ID NO 32
<211> LENGTH: 252
<212> TYPE: PRT
<213> ORGANISM: Artificial Sequence
<220> FEATURE:
<223> OTHER INFORMATION: Synthetic

<400> SEQUENCE: 32

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
            50                  55                  60

Ala Gln Pro Gly Ala Gln Lys His Pro Ile Pro Asp Ser Ser Pro Leu
65                  70                  75                  80

Leu Gln Phe Gly Gly Gln Val Arg Gln Arg Tyr Leu Tyr Thr Asp Asp
                85                  90                  95

Ala Gln Gln Thr Glu Ala His Leu Glu Ile Arg Glu Asp Gly Thr Val
            100                 105                 110

Gly Gly Ala Ala Asp Gln Ser Pro Glu Ser Leu Leu Gln Leu Arg Ala
            115                 120                 125

Leu Arg Pro Gly Val Ile Gln Ile Leu Gly Val Arg Thr Ser Arg Phe
130                 135                 140

Leu Cys Gln Arg Pro Asp Gly Ala Leu Tyr Gly Ser Leu His Phe Asp
145                 150                 155                 160

Pro Glu Ala Cys Ser Phe Arg Glu Leu Leu Leu Glu Asp Gly Tyr Asn
                165                 170                 175

Val Tyr Gln Ser Glu Ala His Gly Leu Pro Leu His Leu Pro Gly Gln
            180                 185                 190

Arg Ser Pro His Arg Asp Pro Ala Pro Arg Gly Pro Ala Arg Phe Leu
            195                 200                 205

Pro Leu Pro Gly Leu Pro Pro Ala Leu Pro Glu Pro Pro Gly Ile Leu
210                 215                 220

Ala Pro Gln Pro Pro Asp Val Gly Ser Ser Asp Pro Leu Ser Leu Val
225                 230                 235                 240

Gly Gly Ser Gln Lys Arg Ser Pro Ser Tyr Glu Ser
                245                 250
```

<210> SEQ ID NO 33
<211> LENGTH: 220
<212> TYPE: PRT
<213> ORGANISM: Artificial Sequence
<220> FEATURE:
<223> OTHER INFORMATION: Synthetic

<400> SEQUENCE: 33

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Lys His Pro Ile Pro Asp Ser Ser Pro Leu
        35                  40                  45

Leu Gln Phe Gly Gly Val Arg Gln Arg Tyr Leu Tyr Thr Asp Asp
    50                  55                  60

Ala Gln Gln Thr Glu Ala His Leu Glu Ile Arg Glu Asp Gly Thr Val
65                  70                  75                  80

Gly Gly Ala Ala Asp Gln Ser Pro Glu Ser Leu Leu Gln Leu Arg Ala
                85                  90                  95

Leu Arg Pro Gly Val Ile Gln Ile Leu Gly Val Arg Thr Ser Arg Phe
                100                 105                 110

Leu Cys Gln Arg Pro Asp Gly Ala Leu Tyr Gly Ser Leu His Phe Asp
            115                 120                 125

Pro Glu Ala Cys Ser Phe Arg Glu Leu Leu Leu Glu Asp Gly Tyr Asn
    130                 135                 140

Val Tyr Gln Ser Glu Ala His Gly Leu Pro Leu His Leu Pro Gly Gln
145                 150                 155                 160

Arg Ser Pro His Arg Asp Pro Ala Pro Arg Gly Pro Ala Arg Phe Leu
                165                 170                 175

Pro Leu Pro Gly Leu Pro Pro Ala Leu Pro Glu Pro Pro Gly Ile Leu
            180                 185                 190

Ala Pro Gln Pro Pro Asp Val Gly Ser Ser Asp Pro Leu Ser Leu Val
        195                 200                 205

Gly Gly Ser Gln Lys Arg Ser Pro Ser Tyr Glu Ser
        210                 215                 220
```

<210> SEQ ID NO 34
<211> LENGTH: 216
<212> TYPE: PRT
<213> ORGANISM: Artificial Sequence
<220> FEATURE:
<223> OTHER INFORMATION: Synthetic

<400> SEQUENCE: 34

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Lys His Pro Ile Pro Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Arg Ala Leu Arg Pro Gly
                85                  90                  95

Val Ile Gln Ile Leu Gly Val Arg Thr Ser Arg Phe Leu Cys Gln Arg
                100                 105                 110

Pro Asp Gly Ala Leu Tyr Gly Ser Leu His Phe Asp Pro Glu Ala Cys
            115                 120                 125
```

Ser Phe Arg Glu Leu Leu Leu Glu Asp Gly Tyr Asn Val Tyr Gln Ser
130                 135                 140

Glu Ala His Gly Leu Pro Leu His Leu Pro Gly Gln Arg Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
                180                 185                 190

Pro Asp Val Gly Ser Ser Asp Pro Leu Ser Leu Val Gly Gly Ser Gln
                195                 200                 205

Lys Arg Ser Pro Ser Tyr Glu Ser
210                 215

<210> SEQ ID NO 35
<211> LENGTH: 232
<212> TYPE: PRT
<213> ORGANISM: Artificial Sequence
<220> FEATURE:
<223> OTHER INFORMATION: Synthetic

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Gly Gly Gly Ser Gly Gly Gly Ser Gly Gly Gly Ser Gly Gly
                35                  40                  45

Gly Gly Ser His Pro Ile Pro Asp Ser Ser Pro Leu Leu Gln Phe Gly
50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
                100                 105                 110

Val Ile Gln Ile Leu Gly Val Arg Thr Ser Arg Phe Leu Cys Gln Arg
                115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
                180                 185                 190

Leu Pro Pro Ala Leu Pro Glu Pro Pro Gly Ile Leu Ala Pro Gln Pro
                195                 200                 205

Pro Asp Val Gly Ser Ser Asp Pro Leu Ser Leu Val Lys Gly Ser Gln
                210                 215                 220

Gly Arg Ser Pro Ser Tyr Glu Ser
225                 230

<210> SEQ ID NO 36
<211> LENGTH: 181
<212> TYPE: PRT
<213> ORGANISM: Artificial Sequence
<220> FEATURE:
<223> OTHER INFORMATION: Synthetic

<400> SEQUENCE: 36

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 37
<211> LENGTH: 181
<212> TYPE: PRT
<213> ORGANISM: Artificial Sequence
<220> FEATURE:
<223> OTHER INFORMATION: Synthetic

<400> SEQUENCE: 37

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Ser Gln Gly Arg Ser
                165                 170                 175

Pro Ser Tyr Lys Ser
            180

<210> SEQ ID NO 38
<211> LENGTH: 181
<212> TYPE: PRT
<213> ORGANISM: Artificial Sequence
<220> FEATURE:
<223> OTHER INFORMATION: Synthetic

<400> SEQUENCE: 38

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Lys Ser Gln Gly Arg Ser
                165                 170                 175

Pro Ser Tyr Ala Ser
            180

<210> SEQ ID NO 39
<211> LENGTH: 181
<212> TYPE: PRT
<213> ORGANISM: Artificial Sequence
<220> FEATURE:
<223> OTHER INFORMATION: Synthetic

<400> SEQUENCE: 39

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Lys Pro Ser Gln Gly Arg Ser
                165                 170                 175

Pro Ser Tyr Ala Ser
            180

<210> SEQ ID NO 40
<211> LENGTH: 181
<212> TYPE: PRT
<213> ORGANISM: Artificial Sequence
<220> FEATURE:
<223> OTHER INFORMATION: Synthetic

<400> SEQUENCE: 40

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Ser Gln Lys Arg Ser
                165                 170                 175

Pro Ser Tyr Ala Ser
            180

<210> SEQ ID NO 41
<211> LENGTH: 181
<212> TYPE: PRT
<213> ORGANISM: Artificial Sequence
<220> FEATURE:
<223> OTHER INFORMATION: Synthetic
```

```
<400> SEQUENCE: 41

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Lys Ser Gln Gly Arg Ser
                165                 170                 175

Pro Ser Tyr Glu Ser
            180

<210> SEQ ID NO 42
<211> LENGTH: 181
<212> TYPE: PRT
<213> ORGANISM: Artificial Sequence
<220> FEATURE:
<223> OTHER INFORMATION: Synthetic

<400> SEQUENCE: 42

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160
```

```
Gly Ser Ser Asp Pro Leu Ser Leu Val Lys Pro Ser Gln Gly Arg Ser
                165                 170                 175

Pro Ser Tyr Glu Ser
            180

<210> SEQ ID NO 43
<211> LENGTH: 181
<212> TYPE: PRT
<213> ORGANISM: Artificial Sequence
<220> FEATURE:
<223> OTHER INFORMATION: Synthetic

<400> SEQUENCE: 43

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Lys Arg Ser
                165                 170                 175

Pro Ser Tyr Glu Ser
            180

<210> SEQ ID NO 44
<211> LENGTH: 181
<212> TYPE: PRT
<213> ORGANISM: Artificial Sequence
<220> FEATURE:
<223> OTHER INFORMATION: Synthetic

<400> SEQUENCE: 44

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95
```

-continued

```
Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Pro Ser Gln Gly Arg Ser
                165                 170                 175

Pro Ser Tyr Lys Ser
            180

<210> SEQ ID NO 45
<211> LENGTH: 180
<212> TYPE: PRT
<213> ORGANISM: Artificial Sequence
<220> FEATURE:
<223> OTHER INFORMATION: Synthetic

<400> SEQUENCE: 45

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Ser Gln Gly Arg Ser
                165                 170                 175

Pro Ser Tyr Lys
            180

<210> SEQ ID NO 46
<211> LENGTH: 181
<212> TYPE: PRT
<213> ORGANISM: Artificial Sequence
<220> FEATURE:
<223> OTHER INFORMATION: Synthetic

<400> SEQUENCE: 46

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30
```

-continued

```
Leu Glu Ile Arg Glu Asp Gly Thr Val Gly Ala Ala Asp Gln Ser
             35                  40                  45

Pro Glu Ser Leu Leu Gln Leu Arg Ala Leu Arg Pro Gly Val Ile Gln
 50                  55                  60

Ile Leu Gly Val Arg Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Lys Gly Ser Gln Gly Arg Ser
                165                 170                 175

Pro Ser Tyr Glu Ser
            180

<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Gly Pro Ser Ala Gly Pro Ser Ala Gly Pro Ser Ala Gly Pro Ser Ala
 1               5                  10                  15

Gly Pro Ser Ala
             20

<210> SEQ ID NO 48
<211> LENGTH: 20
<212> TYPE: PRT
<213> ORGANISM: Artificial Sequence
<220> FEATURE:
<223> OTHER INFORMATION: Synthetic

<400> SEQUENCE: 48

Gly Gly Gly Ser Gly Gly Gly Ser Gly Gly Gly Ser Gly Gly Gly Ser
 1               5                  10                  15

Gly Gly Gly Ser
             20

<210> SEQ ID NO 49
<211> LENGTH: 20
<212> TYPE: PRT
<213> ORGANISM: Artificial Sequence
<220> FEATURE:
<223> OTHER INFORMATION: Synthetic

<400> SEQUENCE: 49

Gly Ser Gly Ser Gly Ser Gly Ser Gly Ser Gly Ser Gly Ser Gly Ser
 1               5                  10                  15

Gly Ser Gly Ser
             20
```

```
<210> SEQ ID NO 50
<211> LENGTH: 31
<212> TYPE: PRT
<213> ORGANISM: Artificial Sequence
<220> FEATURE:
<223> OTHER INFORMATION: Synthetic

<400> SEQUENCE: 50

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is His, imidazole-4-acetate (IA), or
      imidazolepropionic acid (IPA).
<220> FEATURE:
<221> NAME/KEY: MISC_FEATURE
<222> LOCATION: (2)..(2)
<223> OTHER INFORMATION: Xaa is Ala, Gly, Ser, Val, Aib, Thr, Ile or
      Leu.
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (20)..(20)
<223> OTHER INFORMATION: Xaa is Lys, Arg or Cys.
<220> FEATURE:
<221> NAME/KEY: MISC_FEATURE
<222> LOCATION: (21)..(21)
<223> OTHER INFORMATION: Xaa is Glu, Lys or Cys.
<220> FEATURE:
<221> NAME/KEY: MISC_FEATURE
<222> LOCATION: (28)..(28)
<223> OTHER INFORMATION: Xaa is Arg, Lys or Cys.
<220> FEATURE:
<221> NAME/KEY: MISC_FEATURE
<222> LOCATION: (30)..(30)
<223> OTHER INFORMATION: Xaa is Lys, Arg, Gly or Cys.

<400> SEQUENCE: 51

Xaa Xaa Glu Gly Thr Phe Thr Ser Asp Val Ser Ser Tyr Leu Glu Xaa
1               5                   10                  15

Gln Ala Ala Xaa Xaa Phe Ile Ala Trp Leu Val Xaa Gly Xaa Gly
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Synthetic

<400> SEQUENCE: 52

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly
            20                  25                  30
```

```
<210> SEQ ID NO 53
<211> LENGTH: 31
<212> TYPE: PRT
<213> ORGANISM: Artificial Sequence
<220> FEATURE:
<223> OTHER INFORMATION: Synthetic

<400> SEQUENCE: 53

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30

<210> SEQ ID NO 54
<211> LENGTH: 20
<212> TYPE: PRT
<213> ORGANISM: Artificial Sequence
<220> FEATURE:
<223> OTHER INFORMATION: Synthetic

<400> SEQUENCE: 54

Gly Gly Gly Gly Ser Gly Gly Gly Gly Ser Gly Gly Gly Gly Ser Gly
1               5                   10                  15

Gly Gly Gly Ser
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic

<400> SEQUENCE: 55

Gly Ala Gln Pro Gly Ala Gln Pro Gly Ala Gln Pro Gly Ala Gln Pro
1               5                   10                  15

Gly Ala Gln Pro
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic

<400> SEQUENCE: 56

Gly Gln Glu Pro Gly Gln Glu Pro Gly Gln Glu Pro Gly Gln Glu Pro
1               5                   10                  15

Gly Gln Glu Pro
            20

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Gly Gly Gly Gly Ser
1               5
```

```
<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Gly Gly Gly Gly Ser Gly Gly Gly Gly Ser
1               5                   10

<210> SEQ ID NO 59
<211> LENGTH: 40
<212> TYPE: PRT
<213> ORGANISM: Artificial Sequence
<220> FEATURE:
<223> OTHER INFORMATION: Synthetic

<400> SEQUENCE: 59

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly
                20                  25                  30

Gly Gly Ser Gly Gly Gly Gly Ser
            35                  40

<210> SEQ ID NO 60
<211> LENGTH: 80
<212> TYPE: PRT
<213> ORGANISM: Artificial Sequence
<220> FEATURE:
<223> OTHER INFORMATION: Synthetic

<400> SEQUENCE: 60

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
     50                 55                  60

Gly Ala Gln Pro Gly Ala Gln Pro Gly Ala Gln Pro Gly Ala Gln Pro
65                  70                  75                  80

<210> SEQ ID NO 61
<211> LENGTH: 25
<212> TYPE: PRT
<213> ORGANISM: Artificial Sequence
<220> FEATURE:
<223> OTHER INFORMATION: Synthetic

<400> SEQUENCE: 61

Gly Gly Gly Gly Ser Gly Gly Gly Gly Ser Gly Gly Gly Ser Gly
1               5                   10                  15

Gly Gly Gly Ser Gly Gly Gly Gly Ser
                20                  25

<210> SEQ ID NO 62
<211> LENGTH: 48
<212> TYPE: PRT
<213> ORGANISM: Artificial Sequence
<220> FEATURE:
<223> OTHER INFORMATION: Synthetic
```

```
<400> SEQUENCE: 62

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
        35                  40                  45

<210> SEQ ID NO 63
<211> LENGTH: 40
<212> TYPE: PRT
<213> ORGANISM: Artificial Sequence
<220> FEATURE:
<223> OTHER INFORMATION: Synthetic

<400> SEQUENCE: 63

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro
        35                  40

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

Gly Ala Gln Pro Gly Ala Gln Pro
1               5

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Gly Ala Gln Pro
1

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66

Gly Gly Gly Gly Ser Gly Gly Gly Gly Ser Gly Gly Gly Gly Ser Gly
1               5                   10                  15

Gly Gly Gly Lys
            20

<210> SEQ ID NO 67
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 67

Gly Gly Gly Gly Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Gly Gly Gly Gly Ser Gly Gly Gly Gly Lys
1               5                   10

<210> SEQ ID NO 69
<211> LENGTH: 40
<212> TYPE: PRT
<213> ORGANISM: Artificial Sequence
<220> FEATURE:
<223> OTHER INFORMATION: Synthetic

<400> SEQUENCE: 69

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Lys
        35                  40

<210> SEQ ID NO 70
<211> LENGTH: 80
<212> TYPE: PRT
<213> ORGANISM: Artificial Sequence
<220> FEATURE:
<223> OTHER INFORMATION: Synthetic

<400> SEQUENCE: 70

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Lys
65                  70                  75                  80

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Gly Ala Gln Pro Gly Ala Gln Pro Gly Ala Gln Pro Gly Ala Gln Pro
1               5                   10                  15

Gly Ala Gln Lys
            20
```

<210> SEQ ID NO 72
<211> LENGTH: 48
<212> TYPE: PRT
<213> ORGANISM: Artificial Sequence
<220> FEATURE:
<223> OTHER INFORMATION: Synthetic

<400> SEQUENCE: 72

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Lys
        35                  40                  45

<210> SEQ ID NO 73
<211> LENGTH: 40
<212> TYPE: PRT
<213> ORGANISM: Artificial Sequence
<220> FEATURE:
<223> OTHER INFORMATION: Synthetic

<400> SEQUENCE: 73

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Lys
        35                  40

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Gly Ala Gln Pro Gly Ala Gln Lys
1               5

<210> SEQ ID NO 75
<211> LENGTH: 4
<212> TYPE: PRT
<213> ORGANISM: Artificial Sequence
<220> FEATURE:
<223> OTHER INFORMATION: Synthetic

<400> SEQUENCE: 75

Gly Ala Gln Lys
1

<210> SEQ ID NO 76
<211> LENGTH: 252
<212> TYPE: PRT
<213> ORGANISM: Artificial Sequence
<220> FEATURE:
<223> OTHER INFORMATION: Synthetic

<400> SEQUENCE: 76

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

```
Gly Gly Gly Ser Gly Gly Gly Ser Gly Gly Gly Ser Gly Gly
            35                  40                  45
Gly Cys Ser Gly Gly Gly Ser Gly Gly Gly Ser Gly Gly Gly
 50                  55                  60
Gly Ser Gly Gly Gly Cys His Pro Ile Pro Asp Ser Ser Pro Leu
 65                  70                  75                  80
Leu Gln Phe Gly Gly Gln Val Arg Gln Arg Tyr Leu Tyr Thr Asp Asp
                 85                  90                  95
Ala Gln Gln Thr Glu Ala His Leu Glu Ile Arg Glu Asp Gly Thr Val
            100                 105                 110
Gly Gly Ala Ala Asp Gln Ser Pro Glu Ser Leu Leu Gln Leu Lys Ala
            115                 120                 125
Leu Lys Pro Gly Val Ile Gln Ile Leu Gly Val Lys Thr Ser Arg Phe
130                 135                 140
Leu Cys Gln Arg Pro Asp Gly Ala Leu Tyr Gly Ser Leu His Phe Asp
145                 150                 155                 160
Pro Glu Ala Cys Ser Phe Arg Glu Leu Leu Leu Glu Asp Gly Tyr Asn
                165                 170                 175
Val Tyr Gln Ser Glu Ala His Gly Leu Pro Leu His Leu Pro Gly Gln
                180                 185                 190
Lys Ser Pro His Arg Asp Pro Ala Pro Arg Gly Pro Ala Arg Phe Leu
                195                 200                 205
Pro Leu Pro Gly Leu Pro Pro Ala Leu Pro Glu Pro Gly Ile Leu
            210                 215                 220
Ala Pro Gln Pro Pro Asp Val Gly Ser Ser Asp Pro Leu Ser Leu Val
225                 230                 235                 240
Gly Gly Ser Gln Gly Arg Ser Pro Ser Tyr Glu Ser
                245                 250

<210> SEQ ID NO 77
<211> LENGTH: 217
<212> TYPE: PRT
<213> ORGANISM: Artificial Sequence
<220> FEATURE:
<223> OTHER INFORMATION: Synthetic

<400> SEQUENCE: 77

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Gly
                20                  25                  30
Gly Gly Gly Lys His Pro Ile Pro Asp Ser Ser Pro Leu Leu Gln Phe
            35                  40                  45
Gly Gly Gln Val Arg Gln Arg Tyr Leu Tyr Thr Asp Asp Ala Gln Gln
 50                  55                  60
Thr Glu Ala His Leu Glu Ile Arg Glu Asp Gly Thr Val Gly Gly Ala
 65                  70                  75                  80
Ala Asp Gln Ser Pro Glu Ser Leu Leu Gln Leu Arg Ala Leu Arg Pro
                 85                  90                  95
Gly Val Ile Gln Ile Leu Gly Val Arg Thr Ser Arg Phe Leu Cys Gln
            100                 105                 110
Arg Pro Asp Gly Ala Leu Tyr Gly Ser Leu His Phe Asp Pro Glu Ala
            115                 120                 125
Cys Ser Phe Arg Glu Leu Leu Leu Glu Asp Gly Tyr Asn Val Tyr Gln
130                 135                 140
```

Ser Glu Ala His Gly Leu Pro Leu His Leu Pro Gly Gln Arg Ser Pro
145                 150                 155                 160

His Arg Asp Pro Ala Pro Arg Gly Pro Ala Arg Phe Leu Pro Leu Pro
                165                 170                 175

Gly Leu Pro Pro Ala Leu Pro Glu Pro Pro Gly Ile Leu Ala Pro Gln
            180                 185                 190

Pro Pro Asp Val Gly Ser Ser Asp Pro Leu Ser Leu Val Gly Lys Ser
        195                 200                 205

Gln Gly Arg Ser Pro Ser Tyr Glu Ser
    210                 215

<210> SEQ ID NO 78
<211> LENGTH: 222
<212> TYPE: PRT
<213> ORGANISM: Artificial Sequence
<220> FEATURE:
<223> OTHER INFORMATION: Synthetic

<400> SEQUENCE: 78

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Gly Lys His Pro Ile Pro Asp Ser Ser
            35                  40                  45

Pro Leu Leu Gln Phe Gly Gly Gln Val Arg Gln Arg Tyr Leu Tyr Thr
    50                  55                  60

Asp Asp Ala Gln Gln Thr Glu Ala His Leu Glu Ile Arg Glu Asp Gly
65                  70                  75                  80

Thr Val Gly Gly Ala Ala Asp Gln Ser Pro Glu Ser Leu Leu Gln Leu
                85                  90                  95

Arg Ala Leu Arg Pro Gly Val Ile Gln Ile Leu Gly Val Arg Thr Ser
                100                 105                 110

Arg Phe Leu Cys Gln Arg Pro Asp Gly Ala Leu Tyr Gly Ser Leu His
            115                 120                 125

Phe Asp Pro Glu Ala Cys Ser Phe Arg Glu Leu Leu Leu Glu Asp Gly
    130                 135                 140

Tyr Asn Val Tyr Gln Ser Glu Ala His Gly Leu Pro Leu His Leu Pro
145                 150                 155                 160

Gly Gln Arg Ser Pro His Arg Asp Pro Ala Pro Arg Gly Pro Ala Arg
                165                 170                 175

Phe Leu Pro Leu Pro Gly Leu Pro Pro Ala Leu Pro Glu Pro Pro Gly
            180                 185                 190

Ile Leu Ala Pro Gln Pro Pro Asp Val Gly Ser Ser Asp Pro Leu Ser
        195                 200                 205

Leu Val Gly Lys Ser Gln Gly Arg Ser Pro Ser Tyr Glu Ser
    210                 215                 220

<210> SEQ ID NO 79
<211> LENGTH: 252
<212> TYPE: PRT
<213> ORGANISM: Artificial Sequence
<220> FEATURE:
<223> OTHER INFORMATION: Synthetic

<400> SEQUENCE: 79

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Ser Gly Gly Gly Ser Gly Gly Gly Ser Gly Gly Gly
        50                  55                  60

Gly Ser Gly Gly Gly Lys His Pro Ile Pro Asp Ser Ser Pro Leu
65                  70                  75                  80

Leu Gln Phe Gly Gly Gln Val Arg Gln Arg Tyr Leu Tyr Thr Asp Asp
                85                  90                  95

Ala Gln Gln Thr Glu Ala His Leu Glu Ile Arg Glu Asp Gly Thr Val
                100                 105                 110

Gly Gly Ala Ala Asp Gln Ser Pro Glu Ser Leu Leu Gln Leu Arg Ala
                115                 120                 125

Leu Arg Pro Gly Val Ile Gln Ile Leu Gly Val Arg Thr Ser Arg Phe
130                 135                 140

Leu Cys Gln Arg Pro Asp Gly Ala Leu Tyr Gly Ser Leu His Phe Asp
145                 150                 155                 160

Pro Glu Ala Cys Ser Phe Arg Glu Leu Leu Leu Glu Asp Gly Tyr Asn
                165                 170                 175

Val Tyr Gln Ser Glu Ala His Gly Leu Pro Leu His Leu Pro Gly Gln
                180                 185                 190

Arg Ser Pro His Arg Asp Pro Ala Pro Arg Gly Pro Ala Arg Phe Leu
                195                 200                 205

Pro Leu Pro Gly Leu Pro Pro Ala Leu Pro Glu Pro Pro Gly Ile Leu
210                 215                 220

Ala Pro Gln Pro Pro Asp Val Gly Ser Ser Asp Pro Leu Ser Leu Val
225                 230                 235                 240

Gly Lys Ser Gln Gly Arg Ser Pro Ser Tyr Glu Ser
                245                 250

<210> SEQ ID NO 80
<211> LENGTH: 292
<212> TYPE: PRT
<213> ORGANISM: Artificial Sequence
<220> FEATURE:
<223> OTHER INFORMATION: Synthetic

<400> SEQUENCE: 80

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
                35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

```
Ala Gln Pro Gly Ala Gln Pro Gly Ala Gln Pro Gly Ala Gln Lys His
                100                 105                 110

Pro Ile Pro Asp Ser Ser Pro Leu Leu Gln Phe Gly Gly Gln Val Arg
            115                 120                 125

Gln Arg Tyr Leu Tyr Thr Asp Asp Ala Gln Gln Thr Glu Ala His Leu
        130                 135                 140

Glu Ile Arg Glu Asp Gly Thr Val Gly Gly Ala Ala Asp Gln Ser Pro
145                 150                 155                 160

Glu Ser Leu Leu Gln Leu Arg Ala Leu Arg Pro Gly Val Ile Gln Ile
                165                 170                 175

Leu Gly Val Arg Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
210                 215                 220

Leu Pro Leu His Leu Pro Gly Gln Arg Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Pro Asp Val Gly
            260                 265                 270

Ser Ser Asp Pro Leu Ser Leu Val Gly Lys Ser Gln Gly Arg Ser Pro
        275                 280                 285

Ser Tyr Glu Ser
    290

<210> SEQ ID NO 81
<211> LENGTH: 260
<212> TYPE: PRT
<213> ORGANISM: Artificial Sequence
<220> FEATURE:
<223> OTHER INFORMATION: Synthetic

<400> SEQUENCE: 81

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Ala Gln Pro Gly Ala Gln Lys His
65                  70                  75                  80

Pro Ile Pro Asp Ser Ser Pro Leu Leu Gln Phe Gly Gly Gln Val Arg
                85                  90                  95

Gln Arg Tyr Leu Tyr Thr Asp Asp Ala Gln Gln Thr Glu Ala His Leu
            100                 105                 110

Glu Ile Arg Glu Asp Gly Thr Val Gly Gly Ala Ala Asp Gln Ser Pro
        115                 120                 125

Glu Ser Leu Leu Gln Leu Arg Ala Leu Arg Pro Gly Val Ile Gln Ile
    130                 135                 140

Leu Gly Val Arg Thr Ser Arg Phe Leu Cys Gln Arg Pro Asp Gly Ala
145                 150                 155                 160
```

```
Leu Tyr Gly Ser Leu His Phe Asp Pro Glu Ala Cys Ser Phe Arg Glu
                165                 170                 175

Leu Leu Leu Glu Asp Gly Tyr Asn Val Tyr Gln Ser Glu Ala His Gly
            180                 185                 190

Leu Pro Leu His Leu Pro Gly Gln Arg Ser Pro His Arg Asp Pro Ala
        195                 200                 205

Pro Arg Gly Pro Ala Arg Phe Leu Pro Leu Pro Gly Leu Pro Pro Ala
    210                 215                 220

Leu Pro Glu Pro Pro Gly Ile Leu Ala Pro Gln Pro Pro Asp Val Gly
225                 230                 235                 240

Ser Ser Asp Pro Leu Ser Leu Val Gly Lys Ser Gln Gly Arg Ser Pro
                245                 250                 255

Ser Tyr Glu Ser
            260

<210> SEQ ID NO 82
<211> LENGTH: 252
<212> TYPE: PRT
<213> ORGANISM: Artificial Sequence
<220> FEATURE:
<223> OTHER INFORMATION: Synthetic

<400> SEQUENCE: 82

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
50                  55                  60

Ala Gln Pro Gly Ala Gln Lys His Pro Ile Pro Asp Ser Ser Pro Leu
65                  70                  75                  80

Leu Gln Phe Gly Gly Gln Val Arg Gln Arg Tyr Leu Tyr Thr Asp Asp
                85                  90                  95

Ala Gln Gln Thr Glu Ala His Leu Glu Ile Arg Glu Asp Gly Thr Val
            100                 105                 110

Gly Gly Ala Ala Asp Gln Ser Pro Glu Ser Leu Leu Gln Leu Arg Ala
        115                 120                 125

Leu Arg Pro Gly Val Ile Gln Ile Leu Gly Val Arg Thr Ser Arg Phe
    130                 135                 140

Leu Cys Gln Arg Pro Asp Gly Ala Leu Tyr Gly Ser Leu His Phe Asp
145                 150                 155                 160

Pro Glu Ala Cys Ser Phe Arg Glu Leu Leu Leu Glu Asp Gly Tyr Asn
                165                 170                 175

Val Tyr Gln Ser Glu Ala His Gly Leu Pro Leu His Leu Pro Gly Gln
            180                 185                 190

Arg Ser Pro His Arg Asp Pro Ala Pro Arg Gly Pro Ala Arg Phe Leu
        195                 200                 205

Pro Leu Pro Gly Leu Pro Pro Ala Leu Pro Glu Pro Pro Gly Ile Leu
    210                 215                 220

Ala Pro Gln Pro Pro Asp Val Gly Ser Ser Asp Pro Leu Ser Leu Val
225                 230                 235                 240

Gly Lys Ser Gln Gly Arg Ser Pro Ser Tyr Glu Ser
                245                 250
```

<210> SEQ ID NO 83
<211> LENGTH: 220
<212> TYPE: PRT
<213> ORGANISM: Artificial Sequence
<220> FEATURE:
<223> OTHER INFORMATION: Synthetic

<400> SEQUENCE: 83

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Lys His Pro Ile Pro Asp Ser Ser Pro Leu
        35                  40                  45

Leu Gln Phe Gly Gly Gln Val Arg Gln Arg Tyr Leu Tyr Thr Asp Asp
    50                  55                  60

Ala Gln Gln Thr Glu Ala His Leu Glu Ile Arg Glu Asp Gly Thr Val
65                  70                  75                  80

Gly Gly Ala Ala Asp Gln Ser Pro Glu Ser Leu Leu Gln Leu Arg Ala
                85                  90                  95

Leu Arg Pro Gly Val Ile Gln Ile Leu Gly Val Arg Thr Ser Arg Phe
            100                 105                 110

Leu Cys Gln Arg Pro Asp Gly Ala Leu Tyr Gly Ser Leu His Phe Asp
        115                 120                 125

Pro Glu Ala Cys Ser Phe Arg Glu Leu Leu Leu Glu Asp Gly Tyr Asn
    130                 135                 140

Val Tyr Gln Ser Glu Ala His Gly Leu Pro Leu His Leu Pro Gly Gln
145                 150                 155                 160

Arg Ser Pro His Arg Asp Pro Ala Pro Arg Gly Pro Ala Arg Phe Leu
                165                 170                 175

Pro Leu Pro Gly Leu Pro Pro Ala Leu Pro Glu Pro Gly Ile Leu
            180                 185                 190

Ala Pro Gln Pro Pro Asp Val Gly Ser Ser Asp Pro Leu Ser Leu Val
        195                 200                 205

Gly Lys Ser Gln Gly Arg Ser Pro Ser Tyr Glu Ser
    210                 215                 220
```

<210> SEQ ID NO 84
<211> LENGTH: 216
<212> TYPE: PRT
<213> ORGANISM: Artificial Sequence
<220> FEATURE:
<223> OTHER INFORMATION: Synthetic

<400> SEQUENCE: 84

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Lys His Pro Ile Pro Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Arg Ala Leu Arg Pro Gly
                85                  90                  95
```

```
Val Ile Gln Ile Leu Gly Val Arg Thr Ser Arg Phe Leu Cys Gln Arg
            100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Gln Arg Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Leu Val Gly Lys Ser Gln
            195                 200                 205

Gly Arg Ser Pro Ser Tyr Glu Ser
            210                 215

<210> SEQ ID NO 85
<211> LENGTH: 232
<212> TYPE: PRT
<213> ORGANISM: Artificial Sequence
<220> FEATURE:
<223> OTHER INFORMATION: Synthetic

<400> SEQUENCE: 85

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gly Gly Gly Ser Gly Gly Gly Gly Ser Gly Gly Gly Gly Lys Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Lys Ser Gln
            210                 215                 220

Gly Arg Ser Pro Ser Tyr Glu Ser
225                 230
```

<210> SEQ ID NO 86
<211> LENGTH: 232
<212> TYPE: PRT
<213> ORGANISM: Artificial Sequence
<220> FEATURE:
<223> OTHER INFORMATION: Synthetic

<400> SEQUENCE: 86

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Lys Gly Gly Gly Ser Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Gly Ile Leu Ala Pro Gln Pro
        195                 200                 205

Pro Asp Val Gly Ser Ser Asp Pro Leu Ser Leu Val Gly Lys Ser Gln
    210                 215                 220

Gly Arg Ser Pro Ser Tyr Glu Ser
225                 230
```

<210> SEQ ID NO 87
<211> LENGTH: 232
<212> TYPE: PRT
<213> ORGANISM: Artificial Sequence
<220> FEATURE:
<223> OTHER INFORMATION: Synthetic

<400> SEQUENCE: 87

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Lys Gly Gly Gly Ser Gly Gly Gly Ser Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80
```

```
Glu Ala His Leu Glu Ile Arg Glu Asp Gly Thr Val Gly Gly Ala Ala
                 85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Lys Ser Gln
            210                 215                 220

Gly Arg Ser Pro Ser Tyr Glu Ser
225                 230

<210> SEQ ID NO 88
<211> LENGTH: 232
<212> TYPE: PRT
<213> ORGANISM: Artificial Sequence
<220> FEATURE:
<223> OTHER INFORMATION: Synthetic

<400> SEQUENCE: 88

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205
```

Pro Asp Val Gly Ser Ser Asp Pro Leu Ser Leu Val Gly Lys Ser Gln
    210                 215                 220

Gly Arg Ser Pro Ser Tyr Glu Ser
225                 230

<210> SEQ ID NO 89
<211> LENGTH: 20
<212> TYPE: PRT
<213> ORGANISM: Artificial Sequence
<220> FEATURE:
<223> OTHER INFORMATION: Synthetic

<400> SEQUENCE: 89

Gly Gly Gly Gly Ser Gly Gly Gly Gly Ser Gly Gly Gly Gly Lys Gly
1               5                   10                  15

Gly Gly Gly Ser
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic

<400> SEQUENCE: 90

Gly Gly Gly Gly Ser Gly Gly Gly Gly Lys Gly Gly Gly Gly Ser Gly
1               5                   10                  15

Gly Gly Gly Ser
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic

<400> SEQUENCE: 91

Gly Gly Gly Gly Lys Gly Gly Gly Gly Ser Gly Gly Gly Gly Ser Gly
1               5                   10                  15

Gly Gly Gly Ser
            20

<210> SEQ ID NO 92
<211> LENGTH: 4
<212> TYPE: PRT
<213> ORGANISM: Artificial Sequence
<220> FEATURE:
<223> OTHER INFORMATION: Synthetic

<400> SEQUENCE: 92

Gly Gln Glu Pro
1

<210> SEQ ID NO 93
<211> LENGTH: 4
<212> TYPE: PRT
<213> ORGANISM: Artificial Sequence
<220> FEATURE:
<223> OTHER INFORMATION: Synthetic

<400> SEQUENCE: 93

Gly Glu Gln Pro
1

```
<210> SEQ ID NO 94
<211> LENGTH: 4
<212> TYPE: PRT
<213> ORGANISM: Artificial Sequence
<220> FEATURE:
<223> OTHER INFORMATION: Synthetic

<400> SEQUENCE: 94

Gly Pro Gln Glu
1

<210> SEQ ID NO 95
<211> LENGTH: 4
<212> TYPE: PRT
<213> ORGANISM: Artificial Sequence
<220> FEATURE:
<223> OTHER INFORMATION: Synthetic

<400> SEQUENCE: 95

Gly Pro Glu Gln
1

<210> SEQ ID NO 96
<211> LENGTH: 4
<212> TYPE: PRT
<213> ORGANISM: Artificial Sequence
<220> FEATURE:
<223> OTHER INFORMATION: Synthetic

<400> SEQUENCE: 96

Gly Ser Glu Pro
1

<210> SEQ ID NO 97
<211> LENGTH: 4
<212> TYPE: PRT
<213> ORGANISM: Artificial Sequence
<220> FEATURE:
<223> OTHER INFORMATION: Synthetic

<400> SEQUENCE: 97

Gly Glu Ser Pro
1

<210> SEQ ID NO 98
<211> LENGTH: 4
<212> TYPE: PRT
<213> ORGANISM: Artificial Sequence
<220> FEATURE:
<223> OTHER INFORMATION: Synthetic

<400> SEQUENCE: 98

Gly Pro Ser Glu
1

<210> SEQ ID NO 99
<211> LENGTH: 4
<212> TYPE: PRT
<213> ORGANISM: Artificial Sequence
<220> FEATURE:
<223> OTHER INFORMATION: Synthetic

<400> SEQUENCE: 99

Gly Pro Glu Ser
1
```

<210> SEQ ID NO 100
<211> LENGTH: 4
<212> TYPE: PRT
<213> ORGANISM: Artificial Sequence
<220> FEATURE:
<223> OTHER INFORMATION: Synthetic

<400> SEQUENCE: 100

Gly Gln Ala Pro
1

<210> SEQ ID NO 101
<211> LENGTH: 4
<212> TYPE: PRT
<213> ORGANISM: Artificial Sequence
<220> FEATURE:
<223> OTHER INFORMATION: Synthetic

<400> SEQUENCE: 101

Gly Pro Ala Gln
1

<210> SEQ ID NO 102
<211> LENGTH: 4
<212> TYPE: PRT
<213> ORGANISM: Artificial Sequence
<220> FEATURE:
<223> OTHER INFORMATION: Synthetic

<400> SEQUENCE: 102

Gly Pro Gln Ala
1

<210> SEQ ID NO 103
<211> LENGTH: 4
<212> TYPE: PRT
<213> ORGANISM: Artificial Sequence
<220> FEATURE:
<223> OTHER INFORMATION: Synthetic

<400> SEQUENCE: 103

Gly Ser Gln Pro
1

<210> SEQ ID NO 104
<211> LENGTH: 4
<212> TYPE: PRT
<213> ORGANISM: Artificial Sequence
<220> FEATURE:
<223> OTHER INFORMATION: Synthetic

<400> SEQUENCE: 104

Gly Ala Ser Pro
1

<210> SEQ ID NO 105
<211> LENGTH: 4
<212> TYPE: PRT
<213> ORGANISM: Artificial Sequence
<220> FEATURE:
<223> OTHER INFORMATION: Synthetic

<400> SEQUENCE: 105

Gly Pro Ala Ser
1

```
<210> SEQ ID NO 106
<211> LENGTH: 4
<212> TYPE: PRT
<213> ORGANISM: Artificial Sequence
<220> FEATURE:
<223> OTHER INFORMATION: Synthetic

<400> SEQUENCE: 106

Gly Pro Ser Ala
1

<210> SEQ ID NO 107
<211> LENGTH: 4
<212> TYPE: PRT
<213> ORGANISM: Artificial Sequence
<220> FEATURE:
<223> OTHER INFORMATION: Synthetic

<400> SEQUENCE: 107

Gly Gly Gly Ser
1

<210> SEQ ID NO 108
<211> LENGTH: 4
<212> TYPE: PRT
<213> ORGANISM: Artificial Sequence
<220> FEATURE:
<223> OTHER INFORMATION: Synthetic

<400> SEQUENCE: 108

Gly Ser Gly Ser
1

<210> SEQ ID NO 109
<211> LENGTH: 20
<212> TYPE: PRT
<213> ORGANISM: Artificial Sequence
<220> FEATURE:
<223> OTHER INFORMATION: Synthetic

<400> SEQUENCE: 109

Gly Gln Ala Pro Gly Gln Ala Pro Gly Gln Ala Pro Gly Gln Ala Pro
1               5                   10                  15

Gly Gln Ala Pro
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic

<400> SEQUENCE: 110

Gly Ser Gln Pro Gly Ser Gln Pro Gly Ser Gln Pro Gly Ser Gln Pro
1               5                   10                  15

Gly Ser Gln Pro
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic
```

-continued

<400> SEQUENCE: 111

Gly Pro Ala Gln Gly Pro Ala Gln Gly Pro Ala Gln Gly Pro Ala Gln
1               5                   10                  15

Gly Pro Ala Gln
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic

<400> SEQUENCE: 112

Gly Pro Gln Ala Gly Pro Gln Ala Gly Pro Gln Ala Gly Pro Gln Ala
1               5                   10                  15

Gly Pro Gln Ala
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic

<400> SEQUENCE: 113

Gly Ala Ser Pro Gly Ala Ser Pro Gly Ala Ser Pro Gly Ala Ser Pro
1               5                   10                  15

Gly Ala Ser Pro
            20

<210> SEQ ID NO 114
<211> LENGTH: 11
<212> TYPE: PRT
<213> ORGANISM: Artificial Sequence
<220> FEATURE:
<223> OTHER INFORMATION: Synthetic

<400> SEQUENCE: 114

Asp Ile Cys Leu Pro Arg Trp Gly Cys Leu Trp
1               5                   10

<210> SEQ ID NO 115
<211> LENGTH: 31
<212> TYPE: PRT
<213> ORGANISM: Artificial Sequence
<220> FEATURE:
<223> OTHER INFORMATION: Synthetic

<400> SEQUENCE: 115

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30

<210> SEQ ID NO 116
<211> LENGTH: 232
<212> TYPE: PRT
<213> ORGANISM: Artificial Sequence
<220> FEATURE:
<223> OTHER INFORMATION: Synthetic -continued

```
<400> SEQUENCE: 116

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Glu Lys
225                 230

<210> SEQ ID NO 117
<211> LENGTH: 233
<212> TYPE: PRT
<213> ORGANISM: Artificial Sequence
<220> FEATURE:
<223> OTHER INFORMATION: Synthetic

<400> SEQUENCE: 117

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gly Gly Gly Ser Gly Gly Gly Ser Gly Gly Gly Ser Gly Gly
            35                  40                  45

Gly Gly Lys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Arg Ala Leu Arg Pro Gly
            100                 105                 110
```

Val Ile Gln Ile Leu Gly Val Arg Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Arg Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Gly Arg Ser Pro Ser Tyr Glu Ser Lys
225                 230

<210> SEQ ID NO 118
<211> LENGTH: 181
<212> TYPE: PRT
<213> ORGANISM: Artificial Sequence
<220> FEATURE:
<223> OTHER INFORMATION: Synthetic

<400> SEQUENCE: 118

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Glu Lys
            180

<210> SEQ ID NO 119
<211> LENGTH: 182
<212> TYPE: PRT
<213> ORGANISM: Artificial Sequence
<220> FEATURE:
<223> OTHER INFORMATION: Synthetic

<400> SEQUENCE: 119

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Glu Ser Lys
            180

<210> SEQ ID NO 120
<211> LENGTH: 31
<212> TYPE: PRT
<213> ORGANISM: Artificial Sequence
<220> FEATURE:
<223> OTHER INFORMATION: Synthetic

<400> SEQUENCE: 120

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 121
<211> LENGTH: 29
<212> TYPE: PRT
<213> ORGANISM: Artificial Sequence
<220> FEATURE:
<223> OTHER INFORMATION: Synthetic

<400> SEQUENCE: 121

Glu Gly Thr Phe Thr Ser Asp Val Ser Ser Tyr Leu Glu Glu Gln Ala
1               5                   10                  15

Ala Lys Glu Phe Ile Ala Trp Leu Val Lys Gly Gly Gly
            20                  25

<210> SEQ ID NO 122
<211> LENGTH: 20
<212> TYPE: PRT
<213> ORGANISM: Artificial Sequence
<220> FEATURE:
<223> OTHER INFORMATION: Synthetic

```
<400> SEQUENCE: 122

Gly Gly Gly Gly Ser Gly Gly Gly Ser Gly Gly Gly Ser Gly
1               5                   10                  15

Gly Gly Gly Cys
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic

<400> SEQUENCE: 123

Gly Ala Gln Pro Gly Ala Gln Pro Gly Ala Gln Pro Gly Ala Gln Pro
1               5                   10                  15

Gly Ala Gln Cys
            20

<210> SEQ ID NO 124
<211> LENGTH: 24
<212> TYPE: PRT
<213> ORGANISM: Artificial Sequence
<220> FEATURE:
<223> OTHER INFORMATION: Synthetic

<400> SEQUENCE: 124

Gly Ala Gln Pro Gly Ala Gln Pro Gly Ala Gln Pro Gly Ala Gln Pro
1               5                   10                  15

Gly Ala Gln Pro Gly Ala Gln Cys
            20

<210> SEQ ID NO 125
<211> LENGTH: 28
<212> TYPE: PRT
<213> ORGANISM: Artificial Sequence
<220> FEATURE:
<223> OTHER INFORMATION: Synthetic

<400> SEQUENCE: 125

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Cys
            20                  25

<210> SEQ ID NO 126
<211> LENGTH: 20
<212> TYPE: PRT
<213> ORGANISM: Artificial Sequence
<220> FEATURE:
<223> OTHER INFORMATION: Synthetic

<400> SEQUENCE: 126

Gly Gly Gly Gly Ser Gly Gly Gly Ser Gly Gly Gly Cys Gly
1               5                   10                  15

Gly Gly Gly Ser
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic
```

<400> SEQUENCE: 127

Gly Gly Gly Gly Ser Gly Gly Gly Cys Gly Gly Gly Ser Gly
1               5                   10                  15

Gly Gly Gly Ser
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic

<400> SEQUENCE: 128

Gly Ser Ala Pro Gly Ser Pro Ala Gly Ser Pro Thr Gly Ser Ala Pro
1               5                   10                  15

Gly Ser Pro Cys
            20

<210> SEQ ID NO 129
<211> LENGTH: 30
<212> TYPE: PRT
<213> ORGANISM: Artificial Sequence
<220> FEATURE:
<223> OTHER INFORMATION: Synthetic

<400> SEQUENCE: 129

Gly Gly Gly Gly Ser Gly Gly Gly Gly Ser Gly Gly Gly Cys Gly
1               5                   10                  15

Gly Gly Gly Ser Gly Gly Gly Gly Ser Gly Gly Gly Gly Ser
            20                  25                  30

<210> SEQ ID NO 130
<211> LENGTH: 80
<212> TYPE: PRT
<213> ORGANISM: Artificial Sequence
<220> FEATURE:
<223> OTHER INFORMATION: Synthetic

<400> SEQUENCE: 130

Gly Ala Gln Pro Gly Ala Gln Pro Gly Ala Gln Pro Gly Ala Gln Pro
1               5                   10                  15

Gly Ala Gln Pro Cys Gln Ala Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 131
<211> LENGTH: 80
<212> TYPE: PRT
<213> ORGANISM: Artificial Sequence
<220> FEATURE:
<223> OTHER INFORMATION: Synthetic

<400> SEQUENCE: 131

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Cys Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 132
<211> LENGTH: 80
<212> TYPE: PRT
<213> ORGANISM: Artificial Sequence
<220> FEATURE:
<223> OTHER INFORMATION: Synthetic

<400> SEQUENCE: 132

Gly Ala Gln Pro Gly Ala Gln Pro Gly Gln Cys Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 133
<211> LENGTH: 20
<212> TYPE: PRT
<213> ORGANISM: Artificial Sequence
<220> FEATURE:
<223> OTHER INFORMATION: Synthetic

<400> SEQUENCE: 133

Gly Gly Gly Gly Ser Gly Gly Gly Cys Ser Gly Gly Gly Gly Ser Gly
1               5                   10                  15

Gly Gly Gly Cys
            20

<210> SEQ ID NO 134
<211> LENGTH: 40
<212> TYPE: PRT
<213> ORGANISM: Artificial Sequence
<220> FEATURE:
<223> OTHER INFORMATION: Synthetic

<400> SEQUENCE: 134

Gly Gly Gly Gly Ser Gly Gly Gly Gly Ser Gly Gly Gly Gly Ser Gly
1               5                   10                  15

Gly Gly Cys Ser Gly Gly Gly Gly Ser Gly Gly Gly Gly Ser Gly Gly
                20                  25                  30

Gly Gly Ser Gly Gly Gly Gly Cys
            35                  40

```
<210> SEQ ID NO 135
<211> LENGTH: 168
<212> TYPE: PRT
<213> ORGANISM: Artificial Sequence
<220> FEATURE:
<223> OTHER INFORMATION: Synthetic

<400> SEQUENCE: 135

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Cys
                165

<210> SEQ ID NO 136
<211> LENGTH: 181
<212> TYPE: PRT
<213> ORGANISM: Artificial Sequence
<220> FEATURE:
<223> OTHER INFORMATION: Synthetic

<400> SEQUENCE: 136

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Leu Pro Glu Pro Pro Gly Ile Leu Ala Pro Gln Pro Pro Asp Val
145                 150                 155                 160

Gly Ser Ser Asp Pro Leu Ser Leu Val Gly Cys Ser Gln Gly Arg Ser
                165                 170                 175

Pro Ser Tyr Glu Ser
            180

<210> SEQ ID NO 137
<211> LENGTH: 181
<212> TYPE: PRT
<213> ORGANISM: Artificial Sequence
<220> FEATURE:
<223> OTHER INFORMATION: Synthetic

<400> SEQUENCE: 137

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Cys Arg Ser
                165                 170                 175

Pro Ser Tyr Glu Ser
            180

<210> SEQ ID NO 138
<211> LENGTH: 181
<212> TYPE: PRT
<213> ORGANISM: Artificial Sequence
<220> FEATURE:
<223> OTHER INFORMATION: Synthetic

<400> SEQUENCE: 138

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Cys Ser
            180

<210> SEQ ID NO 139
<211> LENGTH: 181
<212> TYPE: PRT
<213> ORGANISM: Artificial Sequence
<220> FEATURE:
<223> OTHER INFORMATION: Synthetic

<400> SEQUENCE: 139

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Glu Ser
            180

<210> SEQ ID NO 140
<211> LENGTH: 182
<212> TYPE: PRT
<213> ORGANISM: Artificial Sequence
<220> FEATURE:
<223> OTHER INFORMATION: Synthetic
```

<400> SEQUENCE: 140

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gln Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Glu Ser Cys
            180

<210> SEQ ID NO 141
<211> LENGTH: 24
<212> TYPE: PRT
<213> ORGANISM: Artificial Sequence
<220> FEATURE:
<223> OTHER INFORMATION: Synthetic

<400> SEQUENCE: 141

Gly Ala Gln Pro Gly Ala Gln Pro Gly Ala Gln Pro Gly Ala Gln Pro
1               5                   10                  15

Gly Ala Gln Pro Gly Ala Gln Pro
            20

<210> SEQ ID NO 142
<211> LENGTH: 28
<212> TYPE: PRT
<213> ORGANISM: Artificial Sequence
<220> FEATURE:
<223> OTHER INFORMATION: Synthetic

<400> SEQUENCE: 142

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro
            20                  25

<210> SEQ ID NO 143
<211> LENGTH: 20
<212> TYPE: PRT
<213> ORGANISM: Artificial Sequence
<220> FEATURE:
<223> OTHER INFORMATION: Synthetic

<400> SEQUENCE: 143

Gly Ser Ala Pro Gly Ser Pro Ala Gly Ser Pro Thr Gly Ser Ala Pro
1               5                   10                  15

Gly Ser Pro Ala
            20

<210> SEQ ID NO 144
<211> LENGTH: 30
<212> TYPE: PRT
<213> ORGANISM: Artificial Sequence
<220> FEATURE:
<223> OTHER INFORMATION: Synthetic

<400> SEQUENCE: 144

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 145
<211> LENGTH: 80
<212> TYPE: PRT
<213> ORGANISM: Artificial Sequence
<220> FEATURE:
<223> OTHER INFORMATION: Synthetic

<400> SEQUENCE: 145

Gly Ala Gln Pro Gly Ala Gln Pro Gly Ala Gln Pro Gly Ala Gln Pro
1               5                   10                  15

Gly Ala Gln Pro Gly Gln Ala Pro Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 146
<211> LENGTH: 80
<212> TYPE: PRT
<213> ORGANISM: Artificial Sequence
<220> FEATURE:
<223> OTHER INFORMATION: Synthetic

<400> SEQUENCE: 146

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Ala Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 147
<211> LENGTH: 80
<212> TYPE: PRT
<213> ORGANISM: Artificial Sequence

```
<220> FEATURE:
<223> OTHER INFORMATION: Synthetic

<400> SEQUENCE: 147

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 148
<211> LENGTH: 232
<212> TYPE: PRT
<213> ORGANISM: Artificial Sequence
<220> FEATURE:
<223> OTHER INFORMATION: Synthetic

<400> SEQUENCE: 148

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Gly Ser Gly Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Cys Ser Gln
    210                 215                 220

Gly Arg Ser Pro Ser Tyr Glu Ser
225                 230
```

```
<210> SEQ ID NO 149
<211> LENGTH: 232
<212> TYPE: PRT
<213> ORGANISM: Artificial Sequence
<220> FEATURE:
<223> OTHER INFORMATION: Synthetic

<400> SEQUENCE: 149
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Gly Ser Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Cys Arg Ser Pro Ser Tyr Glu Ser
225                 230

```
<210> SEQ ID NO 150
<211> LENGTH: 233
<212> TYPE: PRT
<213> ORGANISM: Artificial Sequence
<220> FEATURE:
<223> OTHER INFORMATION: Synthetic

<400> SEQUENCE: 150
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Gly Ser Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

```
Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
        210                 215                 220

Gly Arg Ser Pro Ser Tyr Glu Ser Cys
225                 230

<210> SEQ ID NO 151
<211> LENGTH: 232
<212> TYPE: PRT
<213> ORGANISM: Artificial Sequence
<220> FEATURE:
<223> OTHER INFORMATION: Synthetic

<400> SEQUENCE: 151

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gly Gly Gly Ser Gly Gly Gly Gly Ser Gly Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205
```

Pro Asp Val Gly Ser Ser Asp Pro Leu Ser Leu Val Gly Gly Ser Gln
    210                 215                 220

Gly Arg Ser Pro Ser Tyr Cys Ser
225                 230

<210> SEQ ID NO 152
<211> LENGTH: 232
<212> TYPE: PRT
<213> ORGANISM: Artificial Sequence
<220> FEATURE:
<223> OTHER INFORMATION: Synthetic

<400> SEQUENCE: 152

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Gly Ile Leu Ala Pro Gln Pro
        195                 200                 205

Pro Asp Val Gly Ser Ser Asp Pro Leu Ser Leu Val Gly Cys Ser Gln
    210                 215                 220

Gly Arg Ser Pro Ser Tyr Glu Ser
225                 230

<210> SEQ ID NO 153
<211> LENGTH: 232
<212> TYPE: PRT
<213> ORGANISM: Artificial Sequence
<220> FEATURE:
<223> OTHER INFORMATION: Synthetic

<400> SEQUENCE: 153

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

```
Ala Gln Cys His Pro Ile Pro Asp Ser Ser Pro Leu Leu Gln Phe Gly
 50                  55                  60

Gly Gln Val Arg Gln Arg Tyr Leu Tyr Thr Asp Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Lys Ala Leu Lys Pro Gly
                100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Gly Ser Gln
210                 215                 220

Cys Arg Ser Pro Ser Tyr Glu Ser
225                 230

<210> SEQ ID NO 154
<211> LENGTH: 232
<212> TYPE: PRT
<213> ORGANISM: Artificial Sequence
<220> FEATURE:
<223> OTHER INFORMATION: Synthetic

<400> SEQUENCE: 154

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Gly
             20                  25                  30

Ala Gln Pro Gly Ala Gln Pro Gly Ala Gln Pro Gly Ala Gln Pro Gly
         35                  40                  45

Ala Gln Cys His Pro Ile Pro Asp Ser Ser Pro Leu Leu Gln Phe Gly
 50                  55                  60

Gly Gln Val Arg Gln Arg Tyr Leu Tyr Thr Asp Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Lys Ala Leu Lys Pro Gly
                100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175
```

-continued

Arg Asp Pro Ala Pro Arg Gly Pro Ala Arg Phe Leu Pro Leu Pro Gly
        180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
        210                 215                 220

Gly Arg Ser Pro Ser Tyr Cys Ser
225                 230

<210> SEQ ID NO 155
<211> LENGTH: 236
<212> TYPE: PRT
<213> ORGANISM: Artificial Sequence
<220> FEATURE:
<223> OTHER INFORMATION: Synthetic

<400> SEQUENCE: 155

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Cys His Pro Ile Pro Asp Ser Ser Pro Leu
    50                  55                  60

Leu Gln Phe Gly Gly Gln Val Arg Gln Arg Tyr Leu Tyr Thr Asp Asp
65                  70                  75                  80

Ala Gln Gln Thr Glu Ala His Leu Glu Ile Arg Glu Asp Gly Thr Val
                85                  90                  95

Gly Gly Ala Ala Asp Gln Ser Pro Glu Ser Leu Leu Gln Leu Lys Ala
            100                 105                 110

Leu Lys Pro Gly Val Ile Gln Ile Leu Gly Val Lys Thr Ser Arg Phe
        115                 120                 125

Leu Cys Gln Arg Pro Asp Gly Ala Leu Tyr Gly Ser Leu His Phe Asp
    130                 135                 140

Pro Glu Ala Cys Ser Phe Arg Glu Leu Leu Leu Glu Asp Gly Tyr Asn
145                 150                 155                 160

Val Tyr Gln Ser Glu Ala His Gly Leu Pro Leu His Leu Pro Gly Gln
                165                 170                 175

Lys Ser Pro His Arg Asp Pro Ala Pro Arg Gly Pro Ala Arg Phe Leu
            180                 185                 190

Pro Leu Pro Gly Leu Pro Pro Ala Leu Pro Glu Pro Pro Gly Ile Leu
        195                 200                 205

Ala Pro Gln Pro Pro Asp Val Gly Ser Ser Asp Pro Leu Ser Leu Val
    210                 215                 220

Gly Gly Ser Gln Cys Arg Ser Pro Ser Tyr Glu Ser
225                 230                 235

<210> SEQ ID NO 156
<211> LENGTH: 240
<212> TYPE: PRT
<213> ORGANISM: Artificial Sequence
<220> FEATURE:
<223> OTHER INFORMATION: Synthetic

<400> SEQUENCE: 156

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Cys His Pro Ile Pro Asp
        50                  55                  60

Ser Ser Pro Leu Leu Gln Phe Gly Gly Gln Val Arg Gln Arg Tyr Leu
65                  70                  75                  80

Tyr Thr Asp Asp Ala Gln Gln Thr Glu Ala His Leu Glu Ile Arg Glu
                85                  90                  95

Asp Gly Thr Val Gly Gly Ala Ala Asp Gln Ser Pro Glu Ser Leu Leu
            100                 105                 110

Gln Leu Lys Ala Leu Lys Pro Gly Val Ile Gln Ile Leu Gly Val Lys
        115                 120                 125

Thr Ser Arg Phe Leu Cys Gln Arg Pro Asp Gly Ala Leu Tyr Gly Ser
130                 135                 140

Leu His Phe Asp Pro Glu Ala Cys Ser Phe Arg Glu Leu Leu Leu Glu
145                 150                 155                 160

Asp Gly Tyr Asn Val Tyr Gln Ser Glu Ala His Gly Leu Pro Leu His
                165                 170                 175

Leu Pro Gly Gln Lys Ser Pro His Arg Asp Pro Ala Pro Arg Gly Pro
            180                 185                 190

Ala Arg Phe Leu Pro Leu Pro Gly Leu Pro Pro Ala Leu Pro Glu Pro
        195                 200                 205

Pro Gly Ile Leu Ala Pro Gln Pro Pro Asp Val Gly Ser Ser Asp Pro
    210                 215                 220

Leu Ser Leu Val Gly Gly Ser Gln Cys Arg Ser Pro Ser Tyr Glu Ser
225                 230                 235                 240

<210> SEQ ID NO 157
<211> LENGTH: 232
<212> TYPE: PRT
<213> ORGANISM: Artificial Sequence
<220> FEATURE:
<223> OTHER INFORMATION: Synthetic

<400> SEQUENCE: 157

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Ser Gly Gly Gly Ser Gly Gly
            35                  40                  45

Gly Gly Cys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

```
Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Cys Arg Ser Pro Ser Tyr Glu Ser
225                 230
```

<210> SEQ ID NO 158
<211> LENGTH: 232
<212> TYPE: PRT
<213> ORGANISM: Artificial Sequence
<220> FEATURE:
<223> OTHER INFORMATION: Synthetic

<400> SEQUENCE: 158

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Cys Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
        130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Cys Arg Ser Pro Ser Tyr Glu Ser
225                 230
```

```
<210> SEQ ID NO 159
<211> LENGTH: 232
<212> TYPE: PRT
<213> ORGANISM: Artificial Sequence
<220> FEATURE:
<223> OTHER INFORMATION: Synthetic

<400> SEQUENCE: 159
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Cys Gly Gly Gly Ser Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
    210                 215                 220

Cys Arg Ser Pro Ser Tyr Glu Ser
225                 230

```
<210> SEQ ID NO 160
<211> LENGTH: 232
<212> TYPE: PRT
<213> ORGANISM: Artificial Sequence
<220> FEATURE:
<223> OTHER INFORMATION: Synthetic

<400> SEQUENCE: 160
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Ser Gly Gly
            35                  40                  45

Gly Gly Cys His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                    85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                    165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Cys Ser Gln
            210                 215                 220

Gly Arg Ser Pro Ser Tyr Glu Ser
225                 230

<210> SEQ ID NO 161
<211> LENGTH: 232
<212> TYPE: PRT
<213> ORGANISM: Artificial Sequence
<220> FEATURE:
<223> OTHER INFORMATION: Synthetic

<400> SEQUENCE: 161

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Ser Gly Gly Gly Cys Gly Gly
            35                  40                  45

Gly Gly Ser His Pro Ile Pro Asp Ser Ser Pro Leu Leu Gln Phe Gly
        50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                    85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                    165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Leu Val Gly Cys Ser Gln
    210                 215                 220

Gly Arg Ser Pro Ser Tyr Glu Ser
225                 230

<210> SEQ ID NO 162
<211> LENGTH: 232
<212> TYPE: PRT
<213> ORGANISM: Artificial Sequence
<220> FEATURE:
<223> OTHER INFORMATION: Synthetic

<400> SEQUENCE: 162

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Cys Gly Gly Gly Ser Gly Gly
        35                  40                  45

Gly Gly Ser His Pro Ile Pro Asp Ser Ser Pro Leu Leu Gln Phe Gly
    50                  55                  60

Gly Gln Val Arg Gln Arg Tyr Leu Tyr Thr Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Gly Ile Leu Ala Pro Gln Pro
        195                 200                 205

Pro Asp Val Gly Ser Ser Asp Pro Leu Ser Leu Val Gly Cys Ser Gln
    210                 215                 220

Gly Arg Ser Pro Ser Tyr Glu Ser
225                 230

<210> SEQ ID NO 163
<211> LENGTH: 232
<212> TYPE: PRT
<213> ORGANISM: Artificial Sequence
<220> FEATURE:
<223> OTHER INFORMATION: Synthetic

<400> SEQUENCE: 163

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Ala Pro Gly Ser Pro Ala Gly Ser Pro Thr Gly Ser Ala Pro Gly
        35                  40                  45

-continued

```
Ser Pro Cys His Pro Ile Pro Asp Ser Ser Pro Leu Leu Gln Phe Gly
 50                  55                  60

Gly Gln Val Arg Gln Arg Tyr Leu Tyr Thr Asp Asp Ala Gln Gln Thr
 65                  70                  75                  80

Glu Ala His Leu Glu Ile Arg Glu Asp Gly Thr Val Gly Gly Ala Ala
                 85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Gly Ser Gln
210                 215                 220

Cys Arg Ser Pro Ser Tyr Glu Ser
225                 230

<210> SEQ ID NO 164
<211> LENGTH: 242
<212> TYPE: PRT
<213> ORGANISM: Artificial Sequence
<220> FEATURE:
<223> OTHER INFORMATION: Synthetic

<400> SEQUENCE: 164

His Gly Glu Gly Thr Phe Thr Ser Asp Val Ser Ser Tyr Leu Glu Glu
 1                   5                  10                  15

Gln Ala Ala Lys Glu Phe Ile Ala Trp Leu Val Lys Gly Gly Gly Gly
                 20                  25                  30

Gly Gly Ser Gly Gly Gly Gly Ser Gly Gly Gly Gly Cys Gly Gly Gly
             35                  40                  45

Gly Gly Ser Gly Gly Gly Ser Gly Gly Gly Ser His Pro Ile
         50                  55                  60

Pro Asp Ser Ser Pro Leu Leu Gln Phe Gly Gln Val Arg Gln Arg
 65                  70                  75                  80

Tyr Leu Tyr Thr Asp Asp Ala Gln Gln Thr Glu Ala His Leu Glu Ile
                 85                  90                  95

Arg Glu Asp Gly Thr Val Gly Gly Ala Ala Asp Gln Ser Pro Glu Ser
            100                 105                 110

Leu Leu Gln Leu Lys Ala Leu Lys Pro Gly Val Ile Gln Ile Leu Gly
        115                 120                 125

Val Lys Thr Ser Arg Phe Leu Cys Gln Arg Pro Asp Gly Ala Leu Tyr
130                 135                 140

Gly Ser Leu His Phe Asp Pro Glu Ala Cys Ser Phe Arg Glu Leu Leu
145                 150                 155                 160

Leu Glu Asp Gly Tyr Asn Val Tyr Gln Ser Glu Ala His Gly Leu Pro
                165                 170                 175
```

-continued

Leu His Leu Pro Gly Gln Lys Ser Pro His Arg Asp Pro Ala Pro Arg
            180                 185                 190

Gly Pro Ala Arg Phe Leu Pro Leu Pro Gly Leu Pro Pro Ala Leu Pro
        195                 200                 205

Glu Pro Pro Gly Ile Leu Ala Pro Gln Pro Pro Asp Val Gly Ser Ser
210                 215                 220

Asp Pro Leu Ser Leu Val Gly Ser Gln Cys Arg Ser Pro Ser Tyr
225                 230                 235                 240

Glu Ser

<210> SEQ ID NO 165
<211> LENGTH: 232
<212> TYPE: PRT
<213> ORGANISM: Artificial Sequence
<220> FEATURE:
<223> OTHER INFORMATION: Synthetic

<400> SEQUENCE: 165

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Ala Pro Gly Ser Pro Ala Gly Ser Pro Thr Gly Ser Ala Pro Gly
        35                  40                  45

Ser Pro Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
            100                 105                 110

Val Ile Gln Ile Leu Gly Val Lys Thr Ser Arg Phe Leu Cys Gln Arg
        115                 120                 125

Pro Asp Gly Ala Leu Tyr Gly Ser Leu His Phe Asp Pro Glu Ala Cys
    130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
        195                 200                 205

Pro Asp Val Gly Ser Ser Asp Pro Leu Ser Leu Val Gly Cys Ser Gln
    210                 215                 220

Gly Arg Ser Pro Ser Tyr Glu Ser
225                 230

<210> SEQ ID NO 166
<211> LENGTH: 230
<212> TYPE: PRT
<213> ORGANISM: Artificial Sequence
<220> FEATURE:
<223> OTHER INFORMATION: Synthetic

<400> SEQUENCE: 166

```
Glu Gly Thr Phe Thr Ser Asp Val Ser Ser Tyr Leu Glu Gln Ala
1               5                   10                  15

Ala Lys Glu Phe Ile Ala Trp Leu Val Lys Gly Gly Gly Gly Gly
            20                  25                  30

Gly Ser Gly Gly Gly Ser Gly Gly Gly Ser Gly Gly Gly
        35                  40                  45

Cys His Pro Ile Pro Asp Ser Ser Pro Leu Leu Gln Phe Gly Gly Gln
    50                  55                  60

Val Arg Gln Arg Tyr Leu Tyr Thr Asp Asp Ala Gln Gln Thr Glu Ala
65                  70                  75                  80

His Leu Glu Ile Arg Glu Asp Gly Thr Val Gly Gly Ala Ala Asp Gln
                85                  90                  95

Ser Pro Glu Ser Leu Leu Gln Leu Lys Ala Leu Lys Pro Gly Val Ile
                100                 105                 110

Gln Ile Leu Gly Val Lys Thr Ser Arg Phe Leu Cys Gln Arg Pro Asp
            115                 120                 125

Gly Ala Leu Tyr Gly Ser Leu His Phe Asp Pro Glu Ala Cys Ser Phe
130                 135                 140

Arg Glu Leu Leu Leu Glu Asp Gly Tyr Asn Val Tyr Gln Ser Glu Ala
145                 150                 155                 160

His Gly Leu Pro Leu His Leu Pro Gly Gln Lys Ser Pro His Arg Asp
                165                 170                 175

Pro Ala Pro Arg Gly Pro Ala Arg Phe Leu Pro Leu Pro Gly Leu Pro
            180                 185                 190

Pro Ala Leu Pro Glu Pro Gly Ile Leu Ala Pro Gln Pro Pro Asp
            195                 200                 205

Val Gly Ser Ser Asp Pro Leu Ser Leu Val Gly Cys Ser Gln Gly Arg
    210                 215                 220

Ser Pro Ser Tyr Glu Ser
225                 230
```

<210> SEQ ID NO 167
<211> LENGTH: 219
<212> TYPE: PRT
<213> ORGANISM: Artificial Sequence
<220> FEATURE:
<223> OTHER INFORMATION: Synthetic

<400> SEQUENCE: 167

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
        35                  40                  45

Gly Gly Cys His Pro Ile Pro Asp Ser Ser Pro Leu Leu Gln Phe Gly
    50                  55                  60

Gly Gln Val Arg Gln Arg Tyr Leu Tyr Thr Asp Asp Ala Gln Gln Thr
65                  70                  75                  80

Glu Ala His Leu Glu Ile Arg Glu Asp Gly Thr Val Gly Gly Ala Ala
                85                  90                  95

Asp Gln Ser Pro Glu Ser Leu Leu Gln Leu Lys Ala Leu Lys Pro Gly
                100                 105                 110
```

Val Ile Gln Ile Leu Gly Val Lys Thr Ser Arg Phe Leu Cys Gln Arg
            115                 120                 125

Pro Asp Gly Ala Leu Tyr Gly Ser Leu His Phe Asp Pro Glu Ala Cys
            130                 135                 140

Ser Phe Arg Glu Leu Leu Leu Glu Asp Gly Tyr Asn Val Tyr Gln Ser
145                 150                 155                 160

Glu Ala His Gly Leu Pro Leu His Leu Pro Gly Gln Lys Ser Pro His
                165                 170                 175

Arg Asp Pro Ala Pro Arg Gly Pro Ala Arg Phe Leu Pro Leu Pro Gly
            180                 185                 190

Leu Pro Pro Ala Leu Pro Glu Pro Pro Gly Ile Leu Ala Pro Gln Pro
            195                 200                 205

Pro Asp Val Gly Ser Ser Asp Pro Leu Ser Cys
            210                 215

<210> SEQ ID NO 168
<211> LENGTH: 292
<212> TYPE: PRT
<213> ORGANISM: Artificial Sequence
<220> FEATURE:
<223> OTHER INFORMATION: Synthetic

<400> SEQUENCE: 168

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ala Gln Pro Gly Ala Gln Pro Gly Ala Gln Pro Gly Ala Gln Pro Gly
            35                  40                  45

Ala Gln Pro Cys Gln Ala Pro Gly Ala Gln Pro Gly Ala Gln Pro Gly
        50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro His
            100                 105                 110

Pro Ile Pro Asp Ser Ser Pro Leu Leu Gln Phe Gly Gly Gln Val Arg
            115                 120                 125

Gln Arg Tyr Leu Tyr Thr Asp Asp Ala Gln Gln Thr Glu Ala His Leu
            130                 135                 140

Glu Ile Arg Glu Asp Gly Thr Val Gly Gly Ala Ala Asp Gln Ser Pro
145                 150                 155                 160

Glu Ser Leu Leu Gln Leu Lys Ala Leu Lys Pro Gly Val Ile Gln Ile
                165                 170                 175

Leu Gly Val Lys Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
            195                 200                 205

Leu Leu Leu Glu Asp Gly Tyr Asn Val Tyr Gln Ser Glu Ala His Gly
        210                 215                 220

Leu Pro Leu His Leu Pro Gly Gln Lys Ser Pro His Arg Asp Pro Ala
225                 230                 235                 240

Pro Arg Gly Pro Ala Arg Phe Leu Pro Leu Pro Gly Leu Pro Pro Ala
                245                 250                 255

```
Leu Pro Glu Pro Pro Gly Ile Leu Ala Pro Gln Pro Asp Val Gly
            260                 265                 270

Ser Ser Asp Pro Leu Ser Leu Val Gly Cys Ser Gln Gly Arg Ser Pro
        275                 280                 285

Ser Tyr Glu Ser
        290

<210> SEQ ID NO 169
<211> LENGTH: 292
<212> TYPE: PRT
<213> ORGANISM: Artificial Sequence
<220> FEATURE:
<223> OTHER INFORMATION: Synthetic

<400> SEQUENCE: 169

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro His
            100                 105                 110

Pro Ile Pro Asp Ser Ser Pro Leu Leu Gln Phe Gly Gly Gln Val Arg
        115                 120                 125

Gln Arg Tyr Leu Tyr Thr Asp Asp Ala Gln Gln Thr Glu Ala His Leu
    130                 135                 140

Glu Ile Arg Glu Asp Gly Thr Val Gly Gly Ala Ala Asp Gln Ser Pro
145                 150                 155                 160

Glu Ser Leu Leu Gln Leu Lys Ala Leu Lys Pro Gly Val Ile Gln Ile
                165                 170                 175

Leu Gly Val Lys Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
    210                 215                 220

Leu Pro Leu His Leu Pro Gly Gln Lys Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Asp Val Gly
            260                 265                 270

Ser Ser Asp Pro Leu Ser Leu Val Gly Cys Ser Gln Gly Arg Ser Pro
        275                 280                 285

Ser Tyr Glu Ser
        290
```

```
<210> SEQ ID NO 170
<211> LENGTH: 292
<212> TYPE: PRT
<213> ORGANISM: Artificial Sequence
<220> FEATURE:
<223> OTHER INFORMATION: Synthetic

<400> SEQUENCE: 170

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ala Gln Pro Gly Ala Gln Pro Gly Gln Cys Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro His
            100                 105                 110

Pro Ile Pro Asp Ser Ser Pro Leu Leu Gln Phe Gly Gly Gln Val Arg
        115                 120                 125

Gln Arg Tyr Leu Tyr Thr Asp Asp Ala Gln Gln Thr Glu Ala His Leu
    130                 135                 140

Glu Ile Arg Glu Asp Gly Thr Val Gly Gly Ala Ala Asp Gln Ser Pro
145                 150                 155                 160

Glu Ser Leu Leu Gln Leu Lys Ala Leu Lys Pro Gly Val Ile Gln Ile
                165                 170                 175

Leu Gly Val Lys Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
    210                 215                 220

Leu Pro Leu His Leu Pro Gly Gln Lys Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Pro Asp Val Gly
            260                 265                 270

Ser Ser Asp Pro Leu Ser Leu Val Gly Cys Ser Gln Gly Arg Ser Pro
        275                 280                 285

Ser Tyr Glu Ser
    290

<210> SEQ ID NO 171
<211> LENGTH: 181
<212> TYPE: PRT
<213> ORGANISM: Artificial Sequence
<220> FEATURE:
<223> OTHER INFORMATION: Synthetic
```

<400> SEQUENCE: 171

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Cys Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Gln Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Gly Gly Ser Gln Gly Arg Ser
                165                 170                 175

Pro Ser Tyr Glu Ser
                180
```

CONJUGATES OF FUSION PROTEINS OF GLP-1 AND FGF21

FIELD OF THE INVENTION

The present invention relates to conjugates of fusion proteins, pharmaceutical compositions thereof, and methods of using such to prevent and/or treat diseases.

BACKGROUND

Major biologically active fragment of Glucagon-Like Peptide-1 (GLP-1) is a 30 or 31 amino acid peptide fragment (amino acid 7-36 or 7-37 of GLP-1) deriving from the posttranslational processing of the proglucagon peptide. The initial GLP-1 product GLP-1 stimulates insulin synthesis and secretion and has been shown to prevent hyperglycemia in diabetics, especially type 2 diabetes. However, endogenous GLP-1 only has a half-life of approximately 2 minutes, which results in fasting plasma levels of GLP-1 of only 0-15 pmol/L.

Fibroblast growth factor 21 (FGF 21), a member of the fibroblast growth factor (FGF) family, is a hormone synthesized in several metabolically active organs and regulates glucose and lipid homeostasis. The biology of FGF21 is intrinsically complicated owing to its diverse metabolic functions in multiple target organs. FGF21 has been reported to function in organs such as liver, adipocytes, pancreas, hypothalamus and muscles tissues (Fisher FM, Annu Rev Physiol, 2016, 78:223).

Metabolic disorders are commonly associated with insulin resistance, visceral adiposity, atherogenic dyslipidemia, etc., which pose major and escalating public health and clinical challenge worldwide. However, existing treatment for metabolic diseases faces problems such as short half-life and/or low efficacy.

Therefore, there is a need for an improved therapeutic solution for treating metabolic diseases.

SUMMARY OF THE INVENTION

Provided herein are conjugates of fusion proteins, and pharmaceutical compositions and methods of use for treating/preventing metabolic disorders.

In one aspect, the present disclosure provides a polypeptide conjugate comprising a fusion polypeptide conjugated to at least one clearance reducing moiety (CRM), wherein the fusion polypeptide comprises or consists essentially of, from N-terminus to C terminus, a GLP-1, a polypeptide linker and a FGF21;

wherein the fusion polypeptide further comprises at least one conjugatable residue to which the CRM is conjugated, and wherein the first conjugatable residue is in the FGF21; and wherein the polypeptide linker has a length of at least 0-120 amino acid residues.

In certain embodiments, the polypeptide linker has a length of at least 4, 5, 8, 10, 20, 30, 40, 48, 50, 60, 70, 80, 90, 100, 110, or 120 amino acid resides.

In certain embodiments, the polypeptide conjugate does not comprise an antibody fragment (e.g. Fc).

In certain embodiments, the fusion polypeptide further comprises a second conjugatable residue.

In certain embodiments, the fusion polypeptide comprises up to one conjugatable residue or up to two conjugatable residues.

In certain embodiments, the second conjugatable residue is present in the GLP-1 or in the polypeptide linker.

In certain embodiments, the FGF21 comprises an amino acid sequence having at least 90% sequence identity to SEQ ID NO: 36 while retaining substantial biological activity of SEQ ID NO: 36, and/or the GLP-1 comprises an amino acid sequence having at least 70% sequence identity to SEQ ID NO: 50 while retaining substantial biological activity of SEQ ID NO: 50.

In certain embodiments, the GLP-1 comprises no more than 9, 8, 7, 6, 5, 4, 3 mutations substitutions relative to SEQ ID NO: 50 while retaining substantial biological activity of SEQ ID NO: 50, and/or the FGF21 comprises no more than 12, 11, 10, 9, 8, 7 mutations substitutions relative to SEQ ID NO: 36 while retaining substantial biological activity of SEQ ID NO: 36.

In certain embodiments, the first conjugatable residue in the FGF21 is at a position selected from positions 170, 171, 172, 173, 174, 180, 181 and 182 relative to SEQ ID NO: 36.

In certain embodiments, the first conjugatable residue in the FGF21 comprises an introduced residue, optionally by substitution or by insertion.

In certain embodiments, the conjugatable residue is selected from the group consisting of lysine, cysteine and non-natural amino acid.

In certain embodiments, the first conjugatable residue in the FGF21 is lysine.

In certain embodiments, the conjugatable residue in the FGF21 comprises a substitution selected from the group consisting of: G170K, P171K, S172K, Q173K, G174K, A180K, S181K and ins182K relative to SEQ ID NO: 36.

In certain embodiments, the FGF21 further comprises one or more mutations at positions selected from K56, K59, K69, and K122 relative to SEQ ID NO: 36, to a non-conjugatable residue.

In certain embodiments, the non-conjugatable residue is selected from the group consisting of: Arginine (R), Glutamine (Q), Alanine (A), Glycine (G), Histidine (H), Serine (S), and Threonine (T).

In certain embodiments, the FGF21 comprises mutations of K56R, K59R, K69R, and K122R.

In certain embodiments, the FGF21 further comprises one or more additional mutations at a position selected from positions 121, 168, 171, 180, and 181 relative to SEQ ID NO: 36, provided that the first conjugatable residue is not further mutated.

In certain embodiments, the one or more additional mutations in FGF21 are selected from N121Q, M168L, P171G, A180E, and del181S.

In certain embodiments, the FGF21 comprises up to one conjugatable residue.

In certain embodiments, the FGF21 comprises or consists of a combination of mutations relative to SEQ ID NO: 36 selected from the group consisting of:

1) 121Q, 168L, 180K, 171G, 56R, 59R, 69R, and 122R;
2) 121Q, 168L, 171K, 56R, 59R, 69R, and 122R;
3) 121Q, 168L, 174K, 171G, 56R, 59R, 69R, and 122R;
4) 121Q, 168L, 171K, 56R, 59R, 69R, 122R, and 180E;
5) 121Q, 168L, 174K, 171G, 56R, 59R, 69R, 122R, and 180E;
6) 121Q, 168L, 180K, 56R, 59R, 69R, and 122R;
7) 121Q, 168L, 180K, 171G, 56R, 59R, 69R, 122R, and del181S;
8) 121Q, 168L, 170K, 56R, 59R, 69R, and 122R;
9) 121Q, 168L, 170K, 56R, 59R, 69R, 122R, and 180E;
10) 121Q, 168L, 170K, 171G, 56R, 59R, 69R, 122R and 180E;

11) 121Q, 168L, 180E, 171G, 56R, 59R, 69R, 122R and 181K; and
12) 121Q, 168L, 180E, 171G, 56R, 59R, 69R, 122R, and ins182K.

In certain embodiments, the FGF21 comprises an amino acid sequence selected from SEQ ID NO: 37-46 and 118-119.

In certain embodiments, the GLP-1 comprises no conjugatable residue or up to one conjugatable residue.

In certain embodiments, the second conjugatable residue is in the GLP-1.

In certain embodiments, the second conjugatable residue in the GLP-1 is lysine.

In certain embodiments, the conjugatable residue in the GLP-1 comprises or consists of K26 or K34, relative to SEQ ID NO: 50.

In certain embodiments, the conjugatable residue in the GLP-1 comprises an introduced residue, optionally by substitution or by insertion.

In certain embodiments, the conjugatable residue in the GLP-1 is introduced by a substitution selected from the group consisting of: E27K, and R36K, relative to SEQ ID NO: 50.

In certain embodiments, the GLP-1 further comprises substitution of K26 and/or K34 to a non-conjugatable residue, provided that if K26 or K34 is the conjugatable residue, then it is not substituted.

In certain embodiments, the non-conjugatable residue is selected from the group consisting of Arginine (R), Glutamine (Q), Alanine (A), Glycine (G), Histidine (H), Serine (S), and Threonine (T).

In certain embodiments, the substitution of K26 is selected from K26R and K26Q, and/or the substitution at K34 is selected from K34R and K34Q.

In certain embodiments, the conjugatable residue in the GLP-1 comprises or consists of cysteine or a non-natural amino acid.

In certain embodiments, the conjugatable residue in the GLP-1 is introduced by a substitution at a position selected from the group consisting of: K26, K34, E27 and R36, relative to SEQ ID NO: 50.

In certain embodiments, the GLP-1 further comprises one or more additional mutations at a position selected from the group consisting of: A8, G22, K34, R36, and H7, or any combination thereof, relative to SEQ ID NO: 50, provided that if K34 is the conjugatable residue, then it is not further mutated.

In certain embodiments, the one or more additional mutations in GLP-1 are selected from the group consisting of: H7IA, H7IPA, A8G, G22E, K34R, and R36G, or any combination thereof.

In certain embodiments, the GLP-1 comprises an amino acid sequence of $X_7X_8$EGTFTSDVSSYLEX$_{22}$QAAX$_{26}$X$_{27}$FIAWLVX$_{34}$GX$_{36}$G (SEQ ID NO: 51),
wherein: $X_7$ is H, imidazole-4-acetate (IA), or imidazole-propionic acid (IPA); $X_8$ is A, G, S, V, Aib, T, I or L; $X_{22}$ is G, or E; $X_{26}$ is K, R or C; $X_{27}$ is E, K, or C; $X_{34}$ is R, K, or C, and $X_{36}$ is K, R, G, or C, provided that the GLP-1 comprises up to one conjugatable residue or no conjugatable residue.

In certain embodiments, $X_7$ is H, $X_8$ is G, $X_{22}$ is E; $X_{26}$ is K or R; $X_{27}$ is E; $X_{34}$ is R, and $X_{36}$ is G.

In certain embodiments, the GLP-1 comprises an amino acid sequence selected from the group consisting of: SEQ ID NOs: 52, 53 and 115.

In certain embodiments, the polypeptide linker comprises one or more units of a repeating sequence.

In certain embodiments, the repeating sequence consists of no more than 4, 5 or 6 types of amino acid residues selected from the group consisting of: G, Q, A, E, P, and S.

In certain embodiments, the repeating sequence comprises or consists of an amino acid sequences selected from $G_aS_b$, SEQ ID NO: 65 (GAQP), SEQ ID NO:92 (GQEP), SEQ ID NO:93 (GEQP), SEQ ID NO: 94 (GPQE), SEQ ID NO: 95 (GPEQ), SEQ ID NO: 96 (GSEP), SEQ ID NO: 97 (GESP), SEQ ID NO: 98 (GPSE), SEQ ID NO: 99 (GPES), SEQ ID NO: 100 (GQAP), SEQ ID NO: 101 (GPAQ), SEQ ID NO: 102 (GPQA), SEQ ID NO: 103 (GSQP), SEQ ID NO: 104 (GASP), SEQ ID NO: 105 (GPAS), SEQ ID NO: 106 (GPSA), SEQ ID NO: 107 (GGGS), SEQ ID NO: 108 (GSGS), SEQ ID NO: 57 (GGGGS), and GS, wherein a and b are independently an integer selected from 1 to 5.

In certain embodiments, the polypeptide linker comprises no conjugatable residue or up to one conjugatable residue.

In certain embodiments, the polypeptide linker comprises an amino acid sequence selected from SEQ ID NO: 54-65, 109-113, 3 and 47-49.

In certain embodiments, the second conjugatable residue is in the polypeptide linker.

In certain embodiments, the conjugatable residue in the polypeptide linker comprises an introduced residue, optionally by substitution or by insertion.

In certain embodiments, the conjugatable residue in the polypeptide linker is the most C-terminal residue of the polypeptide linker, or is at least 2, 3, 4, 5, 6, 7, 8, 9, 10, 11, 12, 13, 14, 15 residue away (inclusive of conjugatable residue) from the most N terminal residue of the FGF21.

In certain embodiments, the polypeptide linker comprising the second conjugatable residue comprises an amino acid sequence selected from the group consisting of SEQ ID NO: 66-75 and 89-91.

In certain embodiments, the fusion polypeptide comprises an amino acid sequence selected from the group consisting of: SEQ ID NO: 2, 4-22, 24, 26-35, 77-88 and 116-117.

In another aspect, the present disclosure provides a polypeptide conjugate comprising a fusion polypeptide conjugated to at least one clearance reducing moiety (CRM), wherein the fusion polypeptide comprises or consists essentially of, from N-terminus to C terminus, a GLP-1, a polypeptide linker and a FGF21;
wherein the at least one CRM is conjugated to at least one conjugatable residue in the fusion polypeptide; and
wherein the polypeptide linker has a length of at least 0-120 amino acid residues.

In certain embodiments, the polypeptide linker has a length of at least 4, 5, 8, 10, 20, 24, 28, 30, 40, 48, 50, 60, 70, 80, 90, 100, 110, or 120 amino acid resides.

In certain embodiments, the polypeptide conjugate does not comprise an antibody fragment (e.g. Fc).

In certain embodiments, the fusion polypeptide comprises up to one conjugatable residue or up to two conjugatable residues.

In certain embodiments, the fusion polypeptide comprises a first conjugatable residue to which a CRM is conjugated, and wherein the first conjugatable residue is in the FGF21, in the polypeptide linker, or in the GLP-1. In certain embodiments, the first conjugatable residue is in the FGF21.

In certain embodiments, the fusion polypeptide comprises a first conjugatable residue and a second conjugatable residue, wherein:
1) both conjugatable residues are present in the polypeptide linker,
2) both conjugatable residues are present in the FGF21,
3) both conjugatable residues are present in the GLP-1, 4) the first conjugatable residue is present in the FGF21 and the second conjugatable residue is present in the polypeptide linker,
5) the first conjugatable residue is present in the GLP-1 and the second conjugatable residue is present in the FGF21, or
6) the first conjugatable residue is present in the GLP-1 and the second conjugatable residue is present in the polypeptide linker.

In certain embodiments, the first conjugatable residue is lysine, cysteine, or non-natural amino acid residue, or both the first and the second conjugatable residues are lysine, cysteine, or non-natural amino acid residue.

In certain embodiments, the FGF21 comprises an amino acid sequence having at least 90% sequence identity to SEQ ID NO: 36 while retaining substantial biological activity of SEQ ID NO: 36, and/or the GLP-1 comprises an amino acid sequence having at least 70% sequence identity to SEQ ID NO: 50 while retaining substantial biological activity of SEQ ID NO: 50.

In certain embodiments, the GLP-1 comprises no more than 9, 8, 7, 6, 5, 4, 3 mutations substitutions relative to SEQ ID NO: 50 while retaining substantial biological activity of SEQ ID NO: 50, and/or the FGF21 comprises no more than 12, 11, 10, 9, 8, 7 mutations substitutions relative to SEQ ID NO: 36 while retaining substantial biological activity of SEQ ID NO: 36.

In certain embodiments, the FGF21 comprises one or more mutations at a position selected from positions 121, 168, 171, 180, and 181 relative to SEQ ID NO: 36.

In certain embodiments, the one or more mutations in FGF21 are selected from N121Q, M168L, P171G, A180E, and del181S, or any combination thereof.

In certain embodiments, the FGF21 comprises no conjugatable residue or up to one conjugatable residue.

In certain embodiments, the conjugatable residue in the FGF21 is at a position selected from position 71, 170, 171, 172, 173, 174, 180, 181 and 182 relative to SEQ ID NO: 36.

In certain embodiments, the conjugatable residue in the FGF21 comprises an introduced residue, optionally by substitution or by insertion.

In certain embodiments, the conjugatable residue in the FGF21 is lysine.

In certain embodiments, the conjugatable residue in the FGF21 comprises a substitution selected from the group consisting of: G170K, P171K, S172K, Q173K, G174K, A180K, S181K, S71K and ins182K relative to SEQ ID NO: 36.

In certain embodiments, the FGF21 further comprises one or more mutations at positions selected from K56, K59, K69, and K122 relative to SEQ ID NO: 36, to a non-conjugatable residue.

In certain embodiments, the non-conjugatable residue is selected from the group consisting of: Arginine (R), Glutamine (Q), Alanine (A), Glycine (G), Histidine (H), Serine (S), and Threonine (T).

In certain embodiments, the FGF21 comprises mutations of K56R, K59R, K69R, and K122R.

In certain embodiments, the FGF21 comprises or consists of a combination of mutations relative to SEQ ID NO: 36 selected from the group consisting of:
1) 121Q, 168L, 180K, 171G, 56R, 59R, 69R, and 122R;
2) 121Q, 168L, 171K, 56R, 59R, 69R, and 122R;
3) 121Q, 168L, 174K, 171G, 56R, 59R, 69R, and 122R;
4) 121Q, 168L, 171K, 56R, 59R, 69R, 122R, and 180E;
5) 121Q, 168L, 174K, 171G, 56R, 59R, 69R, 122R, and 180E;
6) 121Q, 168L, 180K, 56R, 59R, 69R, and 122R;
7) 121Q, 168L, 180K, 171G, 56R, 59R, 69R, 122R, and del181S;
8) 121Q, 168L, 170K, 56R, 59R, 69R, and 122R;
9) 121Q, 168L, 170K, 56R, 59R, 69R, 122R, and 180E;
10) 121Q, 168L, 170K, 171G, 56R, 59R, 69R, 122R and 180E;
11) 121Q, 168L, 180E, 171G, 56R, 59R, 69R, 122R and 181K;
12) 121Q, 168L, 180E, 171G, 56R, 59R, 69R, 122R, and ins182K;
13) 71K, 121Q, 168L, 56R, 59R, 69R, and 122R;
14) 71K, 121Q, 168L, 171G, 56R, 59R, 69R, and 122R; and
15) 71K, 121Q, 168L, 171G, 56R, 59R, 69R, 122R, 180E.

In certain embodiments, the FGF21 comprises an amino acid sequence selected from SEQ ID NO: 37-46 and 118-119.

In certain embodiments, the conjugatable residue in FGF21 is a cysteine.

In certain embodiments, the conjugatable residue in the FGF21 comprises a substitution selected from the group consisting of: G170C, P171C, S172C, Q173C, G174C, A180C, S181C, S71C and ins182C relative to SEQ ID NO: 36.

In certain embodiments, the FGF21 comprises or consists of a combination of mutations relative to SEQ ID NO: 36 selected from the group consisting of:
1) 121Q, 168L, 171C, 180E;
2) 121Q, 168L, 171G, 174C, 180E;
3) 121Q, 168L, 171G, 180C;
4) 121Q, 168L, 171G, 180E;
5) 71C, 121Q, 168L, 171G, 180E and
6) 121Q, 168L, 180E, 171G, ins 182C.

In certain embodiments, the FGF21 comprises an amino acid sequence selected from SEQ ID NO: 136-140 and 171.

In certain embodiments, the GLP-1 comprises one or more mutations at a position selected from the group consisting of: A8, G22, K34, R36, and H7, or any combination thereof, relative to SEQ ID NO: 50.

In certain embodiments, the one or more mutations are selected from the group consisting of: H7IA, H7IPA, A8G, G22E, K34R, and R36G, or any combination thereof.

In certain embodiments, the GLP-1 comprises no conjugatable residue or up to one conjugatable residue.

In certain embodiments, the conjugatable residue in the GLP-1 is lysine.

In certain embodiments, the conjugatable residue in the GLP-1 comprises or consists of K26 or K34, relative to SEQ ID NO: 50.

In certain embodiments, the conjugatable residue in the GLP-1 comprises an introduced residue, optionally by substitution or by insertion.

In certain embodiments, the conjugatable residue in the GLP-1 is introduced by a substitution selected from the group consisting of: E27K, and R36K, relative to SEQ ID NO: 50. In such embodiments, the GLP-1 further comprises substitution of K26 and/or K34 to a non-conjugatable residue.

In certain embodiments, the non-conjugatable residue is selected from the group consisting of Arginine (R), Glutamine (Q), Alanine (A), Glycine (G), Histidine (H), Serine (S), and Threonine (T).

In certain embodiments, the substitution of K26 is selected from K26R and K26Q, and/or the substitution at K34 is selected from K34R and K34Q.

In certain embodiments, the conjugatable residue in the GLP-1 comprises or consists of cysteine or a non-natural amino acid.

In certain embodiments, the conjugatable residue in the GLP-1 is introduced by a substitution at a position selected from the group consisting of: K26, K34, E27 and R36, relative to SEQ ID NO: 50.

In certain embodiments, the conjugatable residue(s) in the GLP-1 comprises or consists of cysteine and is introduced by a substitution at a position selected from the group consisting of: K26C, K34C, E27C and R36C, relative to SEQ ID NO: 50.

In certain embodiments, the GLP-1 comprises an amino acid sequence of $X_7X_8EGTFTSDVSSYLEX_{22}QAAX_{26}X_{27}FIAWLVX_{34}GX_{36}G$ (SEQ ID NO: 51), wherein: $X_7$ is H, imidazole-4-acetate (IA), or imidazole-propionic acid (IPA); $X_8$ is A, G, S, V, Aib, T, I or L; $X_{22}$ is G, or E; $X_{26}$ is K, R or C; $X_{27}$ is E, K, or C; $X_{34}$ is R, K, or C, and $X_{36}$ is K, R, G, or C.

In certain embodiments, $X_7$ is H, $X_8$ is G, $X_{22}$ is E; $X_{26}$ is K or R; $X_{27}$ is E; $X_{34}$ is R, and $X_{36}$ is G.

In certain embodiments, the GLP-1 comprises an amino acid sequence selected from the group consisting of: SEQ ID NOs: 52, 53, and 115.

In certain embodiments, the GLP-1 comprises an amino acid sequence of SEQ ID NO: 120 or 52.

In certain embodiments, the polypeptide linker comprises one or more units (e.g. 3, 4, 5, 6, 7, 8, 9, 10, or more) of a repeating sequence. In certain embodiments, the polypeptide linker comprises two or more different repeating sequences.

In certain embodiments, the repeating sequence consists of no more than 4, 5, or 6 types of amino acid residues selected from the group consisting of: G, Q, A, E, P, T and S.

In certain embodiments, the repeating sequence comprises or consists of an amino acid sequences selected from GaSb, SEQ ID NO: 65 (GAQP), SEQ ID NO:92 (GQEP), SEQ ID NO:93 (GEQP), SEQ ID NO: 94 (GPQE), SEQ ID NO: 95 (GPEQ), SEQ ID NO: 96 (GSEP), SEQ ID NO: 97 (GESP), SEQ ID NO: 98 (GPSE), SEQ ID NO: 99 (GPES), SEQ ID NO: 100 (GQAP), SEQ ID NO: 101 (GPAQ), SEQ ID NO: 102 (GPQA), SEQ ID NO: 103 (GSQP), SEQ ID NO: 104 (GASP), SEQ ID NO: 105 (GPAS), SEQ ID NO: 106 (GPSA), SEQ ID NO: 107 (GGGS), SEQ ID NO: 108 (GSGS), SEQ ID NO: 57 (GGGGS), SEQ ID NO: 143 (GSAPGSPAGSPTGSAPGSPA) and GS, wherein a and b are independently an integer selected from 1 to 5.

In certain embodiments, the polypeptide linker comprises an amino acid sequence selected from SEQ ID NO: 54-65, 109-113, 3, 47-49 and 141-147.

In certain embodiments, the polypeptide linker comprises no conjugatable residue or up to one conjugatable residue, or up to two conjugatable residues.

In certain embodiments, the conjugatable residue in the polypeptide linker comprises an introduced residue, optionally by substitution or by insertion.

In certain embodiments, the conjugatable residue in the polypeptide linker is the most C-terminal residue of the polypeptide linker, or is at least 2, 3, 4, 5, 6, 7, 8, 9, 10, 11, 12, 13, 14, 15, 16, 17, 18, 19, 20, 21, 22, 23, 24, 25, 30, 40, 50, 60, 70 residues away (inclusive of conjugatable residue) from the most N terminal residue of the FGF21.

In certain embodiments, the conjugatable residue in the polypeptide linker is lysine and the polypeptide linker comprises an amino acid sequence selected from the group consisting of SEQ ID NO: 66-75 and 89-91.

In certain embodiments, the conjugatable residue in the polypeptide linker is cysteine and the polypeptide linker comprises an amino acid sequence selected from the group consisting of SEQ ID NO: 122-132.

In certain embodiments, the polypeptide linker comprises two conjugatable residues and comprises an amino acid sequence of SEQ ID NO: 133 or 134.

In certain embodiments, the conjugatable residue is lysine, and the fusion polypeptide comprises an amino acid sequence selected from the group consisting of: SEQ ID NO: 2, 4-22, 24, 26-35, 77-88, and 116-117.

In certain embodiments, the conjugatable residue is cysteine, and the fusion polypeptide comprises an amino acid sequence selected from the group consisting of: 148-165, 168-170, 1, 23, 25 and 76.

In certain embodiments of any of the aspects disclosed herein, the CRM comprises a structure of *-A-B-C-D-E, wherein A, B, C, D and E are interconnected via amide bonds, and the * end of A is connected to the conjugatable residue on the polypeptide complex, and wherein:

A is selected from a bond,

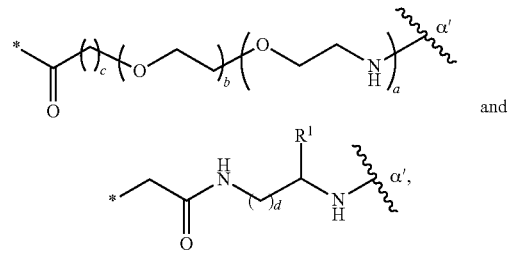

and a, b, c and d are independently an integer from 0 to 4, $R^1$ is hydrogen or —COOH;

B is selected from a bond,

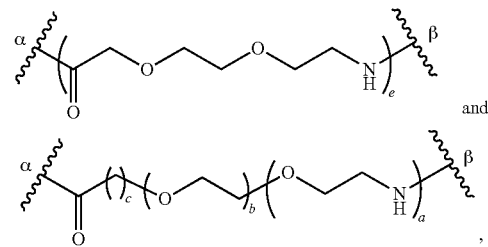

, e is an integer from 1 to 4, wherein position α is linked to the position α',

C is a bond or

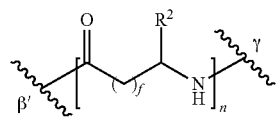

, $R^2$ is —CH$_2$SO$_3$H or —COOH, f is an integer from 1 to 4, n is an integer from 1 to 25, wherein when B is not bond, then position β' is linked to position β, or when B is bond, then position β' is linked to position α';

D is selected from a bond,

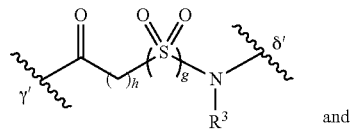

and

-continued

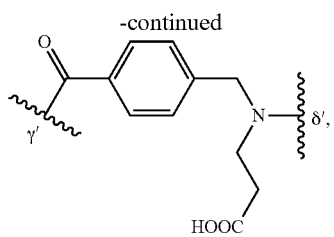

g and h are independently 0 or 1, and R³ is H or —CH₂COOH, wherein:
  when B is not a bond and C is a bond, then position γ' is linked to position β;
  when C is not a bond, then position γ' is linked to position γ; and
  when B is a bond and C is a bond, then position γ' is linked to position α';
E is an acidic group having a formula:

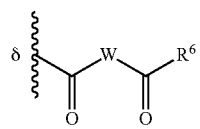
(I)

wherein W represents —(CR⁴R⁵)$_f$—,
R⁴ and R⁵ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide,
R⁶ is selected from hydroxyl or NR⁷R⁸;
R⁷ and R⁸ are independently selected from the group consisting of hydrogen, alkyl, hydroxyl, and

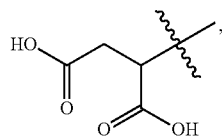

and
l is an integer from 10 to 20,
and wherein:
  when D is not a bond, then position δ is linked to position δ',
  when C is not a bond and D is a bond, then position δ is linked to position γ,
  when B is not a bond, C is a bond and D is a bond, then position δ is linked to position β,
  when A is not a bond, and all of B, C, and D are bond, then position δ is linked to position α',
or a pharmaceutically acceptable salt thereof.

In certain embodiments, the CRM is conjugated to at least one lysine residue in the fusion polypeptide.

In certain embodiments, A is a bond, B is a bond, and C is a bond.

In certain embodiments, A is

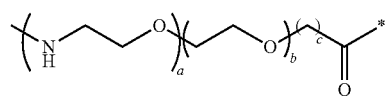

and B is

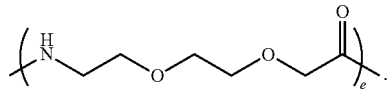

In certain embodiments, A is

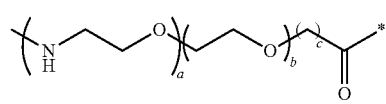

and B is a bond.

In certain embodiments, the CRM comprises the structure of below formula:

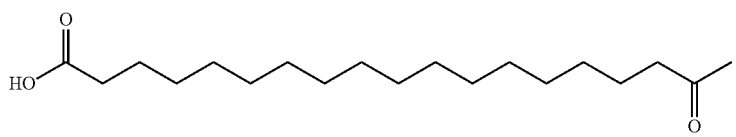

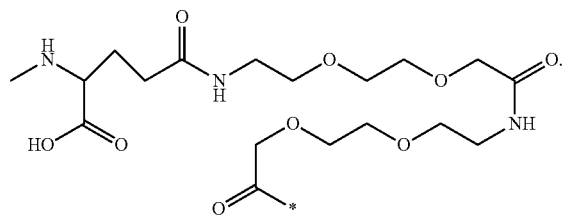

In certain embodiments, the CRM is conjugated to at least one cysteine residue in the fusion polypeptide.

In certain embodiments, A is

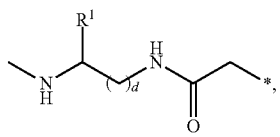

and B is

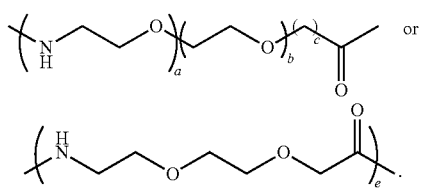

In certain embodiments, the CRM comprises the structure of below formula:

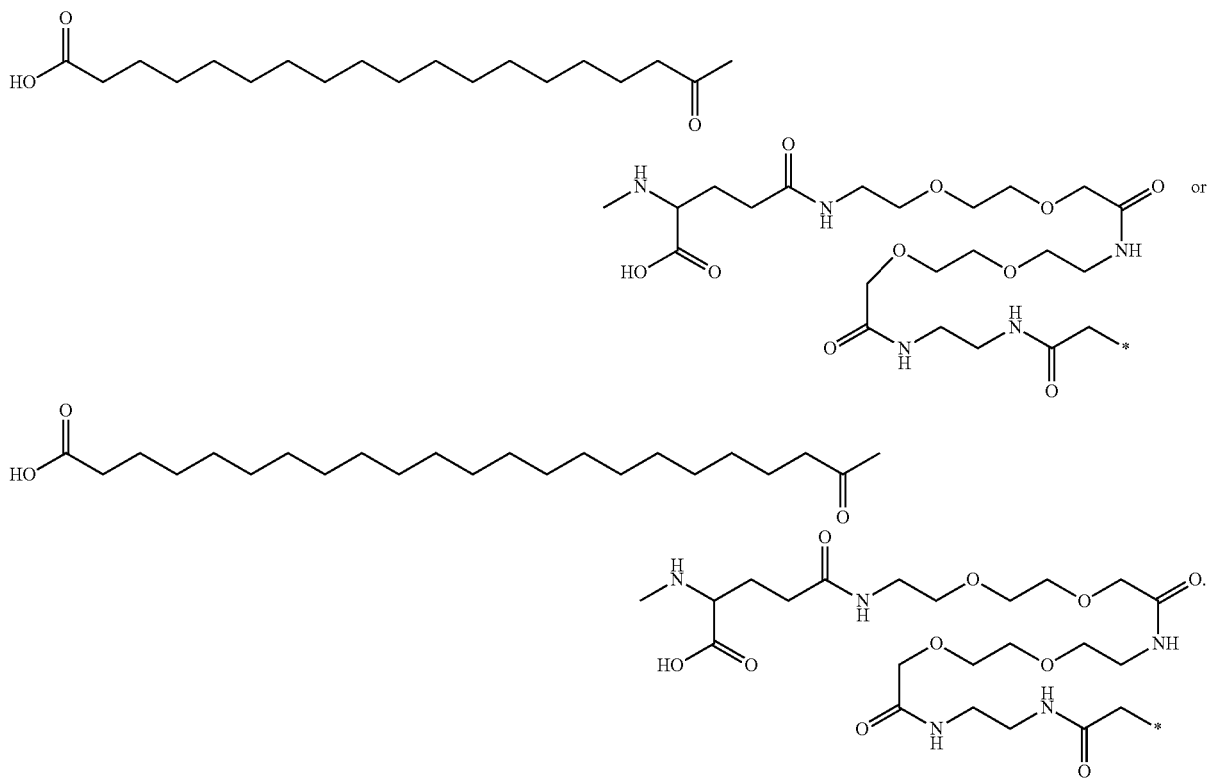

In another aspect, the present disclosure provides a pharmaceutical composition comprising the polypeptide conjugate disclosed herein and a pharmaceutically acceptable carrier.

In another aspect, the present disclosure provides a method of preventing or treating a metabolic disorder in a subject in need thereof, comprising administering a therapeutically effective amount of the polypeptide conjugate disclosed herein or the pharmaceutical composition disclosed herein.

In some embodiments, the metabolic disorder is diabetes, obesity, non-alcoholic steatohepatitis (NASH), cardiovascular like dyslipidaemia, arteriosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

In another aspect, the present disclosure provides a polynucleotide that encodes the fusion polypeptide as described herein.

In another aspect, the present disclosure provides a vector comprising the polynucleotide disclosed herein.

In another aspect, the present disclosure provides a host cell comprising the vector disclosed herein.

In another aspect, the present disclosure provides a process for producing fusion polypeptide as described herein, comprising, culturing the host cell disclosed herein under a condition that allows expression of the polynucleotide disclosed herein.

In another aspect, the present disclosure provides a process for producing a polypeptide conjugate disclosed herein, comprising, conjugating a clearance-reducing moiety to the fusion polypeptide as described herein.

Throughout the present disclosure, the articles "a," "an," and "the" are used herein to refer to one or to more than one (i.e., to at least one) of the grammatical object of the article. By way of example, "a fusion polypeptide" means one fusion polypeptide or more than one fusion polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

The term such as "comprising" are to be construed as open-ended terms (i.e., meaning "including, but not limited to,") unless otherwise noted.

The term "consist essentially of" implies the exclusion of all, most or all but a negligible amount of other elements, or it allows for elements not explicitly recited, but excludes elements that are found in the prior art or that affect a basic or novel property. When a polypeptide is said to "consist essentially of" an amino acid sequence, this means that the polypeptide is composed mostly of the amino acid sequence, with no more than 10 (for example, no more than 6, 5, 4, 3, 2, or 1) additional amino acid residues at one end or both ends of the polypeptide.

BRIEF DESCRIPTION OF THE FIGURES

FIG. 1A shows body weight loss upon treatments from Day 1 to Day 11. FIG. 1B shows body weight loss on Day 11. Compared to Vehicle control: *, $p<0.05$; *, $p<0.001$; Compared to Semaglutide (JP51144): ##, $p<0.01$; ###, $p<0.001$. FIG. 1C shows body weight loss upon protein treatments from Day 1 to Day 15. FIG. 1D shows body weight loss on Day 15. Compared to Vehicle control: *, $p<0.001$; ns, non-statistically significant; Compared to Semaglutide (JP51144): #, $p<0.05$; ##, $p<0.01$; ###, $p<0.001$. FIG. 1E shows body weight loss upon protein treatments from Day 1 to Day 11. FIG. 1F shows body weight loss on Day 11. Compared to Vehicle control: ***, $p<0.001$. All data are expressed as mean values and standard error (SEM).

FIG. 3A shows body weight reduction at 10 nmol/kg. FIG. 3B shows body weight effect at 30 nmol/kg. Data are expressed as mean values and standard error (SEM). n=5 for each treatment group.

FIG. 4A shows body weight loss upon protein treatments. Compared to Vehicle control: *, $p<0.05$, , $p<0.01$ *, $p<0.001$, ****, $p<0.0001$; Compared to Semaglutide (JP51144): #, $p<0.05$. FIG. 4B shows body weight change on Day 22. FIG. 4C shows fasting glucose change upon treatment. FIG. 4D shows insulin concentrations in the terminal plasma on Day 22. FIG. 4E shows plasma triglyceride concentrations in the terminal plasma on Day 22. FIG. 4F shows liver triglyceride levels on Day 22. Data are expressed as mean values and standard error (SEM). n=5 for each treatment group.

FIGS. 5A-5Q shows all the sequences disclosed in the present disclosure. FIGS. 5A, 5B, 5C, 5D, 5E, 5F, 5G, 5H, 5I show amino acid sequences of fusion polypeptides provided herein. FIGS. 5J, 5K, 5L, 5M, 5N, 5O show amino acid sequences of amino acid sequence of FGF21. FIG. 5P shows amino acid sequences of repeating sequence of polypeptide linker. FIG. 5Q shows amino acid sequences of albumin binding peptide.

DETAILED DESCRIPTION

Figure 1A:
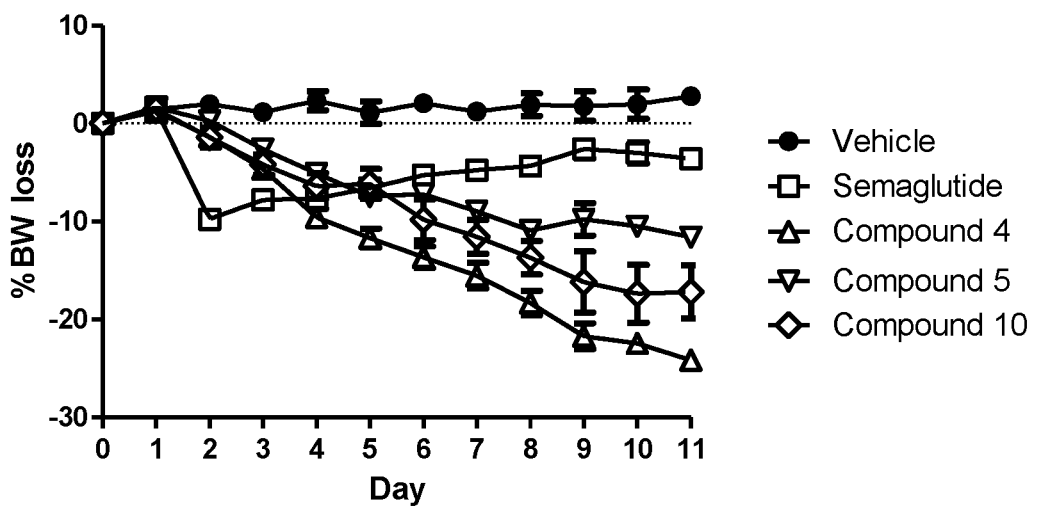
FIGS. 1A-1F show in vivo activities of fusion protein conjugates. To evaluate the body weight effects of the fusion protein conjugates, 10 week old male C57BL/6J mice were dosed everyday subcutaneously with 30 nmol/kg fusion protein conjugates (as shown in the figure legend), Semaglutide or vehicle control for 6, 10 or 14 days. Body weight was measured daily.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional form" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide and retain at least partial function of the parent polypeptide. A variant may differ from the parent polypeptide by one or more amino acid residues. For example, a variant may have substitutions, additions, deletions, insertions, or truncations of one more amino acid residue of the parent polypeptide.

The term "fragment" as used herein refers to partial sequence of the parent polypeptide of any length. A fragment can still retain at least partial function of the parent polypeptide.

The term "derivative" as used herein refers to a chemically modified polypeptide or fusion polypeptide, in which one or more well-defined substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

In one aspect, the present disclosure provides a polypeptide conjugate comprising a fusion polypeptide conjugated to at least one clearance reducing moiety (CRM), wherein the fusion polypeptide comprises or consists essentially of, from N-terminus to C terminus, a GLP-1, a polypeptide linker and a FGF21, wherein the at least one CRM is conjugated to at least one conjugatable residue in the fusion polypeptide. In certain embodiments, the polypeptide linker has a length of at least 0-120 amino acid residues.

In another aspect, the present disclosure provides a polypeptide conjugate comprising a fusion polypeptide conjugated to at least one clearance reducing moiety (CRM), wherein the fusion polypeptide comprises or consists essentially of, from N-terminus to C terminus, a GLP-1, a polypeptide linker and a FGF21; wherein the fusion polypeptide further comprises at least one conjugatable residue to which the CRM is conjugated, and wherein the first conjugatable residue is in the FGF21; and wherein the polypeptide linker has a length of at least 0-120 amino acid residues.

Fusion Polypeptides

The term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence may be produced by genetic recombination of two encoding polynucleotide sequences, and can be expressed by a method of introducing a construct containing the recombinant polynucleotides into a host cell.

The term "protein", "peptide" and "polypeptide" are used interchangeably herein and refer a polymer of amino acid residues linked by covalent bonds such as peptide bonds. A protein or polypeptide as provided herein can comprise naturally occurring or non-natural amino acid residues, or both. Polypeptides, peptides and proteins provided herein can comprise any suitable length of amino acid residues, for example, from at least 3, 4, 5, 10, 20, 30, 40, 50, 60, 70, 80, 90, 100, 200, 300, 400, 500, 600, 700, 800, 900, 1000, or more amino acid residues in length.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Trp or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, γ-carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups {e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofarnesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (Tle), 3-aminomethyl benzoic acid, anthranilic acid, des-amino-histidine (abbreviated DesaminoHis, alternative name imidazopropionic acid, abbreviated lmpr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl) carboxylic acid, and (1-aminocyclooctyl)carboxylic acid.

Introduction of non-natural amino acids into a fusion polypeptide, polypeptide fragment, and/or polypeptide complex may be realized by the technology described in Wang et al., Science 292:498-500, 2001; Deiters et al., J Am Chem Soc 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons, such as a four-base codon (e.g. AGGA, AGGU, CGGU, CGCU, CGAU, CCCU, CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice.

GLP-1

The term "Glucagon-like peptide-1" or "GLP-1" as used herein is intended to broadly encompasses native GLP-1 peptide and all its functional forms such as its functional variants, fragments, fusions, derivatives and mimetics.

The term "native GLP-1 peptide" as used herein refers to the native human Glucagon-Like Peptide-1 (GLP-1 (7-37)), the sequence of which is set forth in SEQ ID NO: 50. The numbering of the residues in GLP-1 is referred to the sequence of SEQ ID NO: 50, which begins with His at position 7 and ends with Gly at position 37.

A functional form of the native GLP-1 peptide is capable of activating the GLP-1 receptor at a level comparable to, or no less than about 20% (or no less than 30%, 40%, 50%, 60%, 70%, 80%, 90%) of, that of the native GLP-1 peptide. Activation of the GLP-1 receptor typically initiates signal transduction pathway resulting in insulinotropic action or other physiological effects as is known in the art. Many functional forms of GLP-1 peptide are known in the art, for example, without limitation, liraglutide, semaglutide, dulaglutide, albiglutide, and those disclosed in WO2000055203A1, WO 98/08871, WO 2006/097537, WO2007139589A1, WO1998019698A1, WO2001098331A2, WO2003040309A2, WO2005000892A2, WO2015000942A1, WO2016083499A1 the disclosure of which is incorporated herein to its entirety.

In certain embodiments, the GLP-1 provided herein comprises an amino acid sequence having at least 70% (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to SEQ ID NO: 50 while retaining substantial biological activity of SEQ ID NO: 50.

In certain embodiments, the GLP-1 comprises no more than 9, 8, 7, 6, 5, 4, 3, or 2 substitutions relative to SEQ ID NO: 50 while retaining substantial biological activity of SEQ ID NO: 50. In certain embodiments, the GLP-1 comprises at least 2, 3, 4, 5, 6, 7, 8, or 9 substitutions relative to SEQ ID NO: 50 while retaining substantial biological activity of SEQ ID NO: 50.

In certain embodiments, the GLP-1 further comprises one or more mutations. One of ordinary skill in the art will appreciate that various amino acid substitutions, e.g., conservative amino acid substitutions, may be made in the sequence of any of the polypeptide described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

Various substitutions have been introduced to native GLP-1 peptide, and have been shown to be capable of retaining or even improving its biological activities. In certain embodiments, the GLP-1 comprises one or more mutations at a position selected from the group consisting of: A8, G22, K34, R36, and H7, and or any combination thereof, relative to SEQ ID NO: 50. For example, it is believed that substitution at A8 is useful to prevent DPP4 enzymatic cleavage at the residue, substitution at G22 is desirable to improve activity and solubility, and substitution at R36 is useful to reduce immunogenicity. Examples of substitutions at these positions include, without limitation, H7IA, H71IPA, A8G, A8S, A8V, A8Aib, A8T, A8I, A8L, G22E, K34R, R36G, or any combination thereof, as well as the substitutions described in U.S. Pat. No. 8,273,854, which are incorporated herein by its entirety. In certain embodiments, the one or more additional substitutions comprises a conservative substitution.

In certain embodiments, the GLP-1 comprises an substitution of A8 which is selected from the group consisting of: A8G, A8S, A8V, A8Aib, A8T, and A8L. In certain embodiments, the GLP-1 comprises an substitution of G22E. In certain embodiments, the GLP-1 comprises an substitution of R36G. In certain embodiments, the GLP-1 comprises an substitution of H7 is H7IA or H7IPA. In certain embodiments, the GLP-1 comprises a substitution of K34 which is K34R.

In certain embodiments, the GLP-1 comprises or consists of one or more substitutions selected from the group consisting of A8G, K26R, K34R, G22E, and R36G. In certain embodiments, the GLP-1 comprises or consists of one or more substitutions selected from the group consisting of A8G, K34R, G22E, and R36G.

FGF21

The term "Fibroblast Growth Factor 21" or "FGF21" as used herein is intended to broadly encompasses the native human FGF21 as well as functional variants, fragments, fusions, derivatives or mimetics thereof. The native human FGF21 consists of 209 amino acid residues (Uniprot database with access no. Q9NSA1), with amino acid residues 1-28 being a signal polypeptide and amino acid residues 29-209 being a mature polypeptide of 181 residues. The FGF21 provided in the present disclosure can be the mature polypeptide, or functional variants, fragments, fusions, derivatives or mimetics thereof. The mature polypeptide of FGF21 is included herein as SEQ ID NO: 36. As used herein, the numbering of the residues in FGF21 is referred to the sequence of SEQ ID NO: 36, which begins with His at position 1 and Ser at position 181.

A functional form of the mature polypeptide of FGF21 is capable of activating the FGF21 receptor at a level comparable to, or no less than about 20% (or no less than 30%, 40%, 50%, 60%, 70%, 80%, 90%) of, that of the mature polypeptide of the native human FGF21. Activation of the FGF21 receptor can lead to biological activities such as, for example, the ability to activate glucose uptake in adipocytes, the ability to lower blood glucose and triglyceride levels, or the ability to lower bodyweight (Tezze C et al, Front Physiol. 2019, 10:419). Many functional forms of the mature polypeptide of FGF21 are known in the art, for example, without limitation, those disclosed in, WO2019043457A2, WO2018088838A1, WO2018039081A1, WO2017220706A1, WO2017180988A2, WO2017116207A1, WO2017093465, WO2017059371A1, WO2016102562A1, WO2016065326A, WO2013173158A1, WO2013052311A1, WO2013033452A2, WO2012066075A1, WO2012059873A2, WO2012010553A1, WO2011140086A2, WO2010084169A2, WO2010065439A1, WO2008121563A2, WO2006028595A2, WO2006028714A1, WO2005113606A2, WO2016102562A, disclosure of which are incorporated herein by their entirety.

In certain embodiments, the FGF21 provided herein comprises an amino acid sequence having at least 90% sequence identity to SEQ ID NO: 36 while retaining substantial biological activity of SEQ ID NO: 36.

In certain embodiments, the FGF21 comprises no more than 12, 11, 10, 9, 8, 7, 6, 5, 4, 3 or 2 substitutions relative to SEQ ID NO: 36 while retaining substantial biological activity of SEQ ID NO: 36. In certain embodiments, the FGF21 comprises at least 2, 3, 4, 5, 6, 7, 8, 9, 10, 11 or 12 substitutions relative to SEQ ID NO: 36 while retaining substantial biological activity of SEQ ID NO: 36.

In certain embodiments, the FGF21 comprises one or more mutations. In certain embodiments, the one or more mutations comprise a conservative substitution. In certain embodiments, the one or more mutations is at a position selected from positions 121, 168, 171, 180, and 181 relative to SEQ ID NO: 36. In certain embodiments, the one or more mutations in FGF21 are selected from N121Q, M168L, P171G, A180E, and del181S. "del181S" as used herein refers to deletion of Serine at the 181 position of the FGF21.

Linker

The term "polypeptide linker" as used herein can be any suitable polypeptide capable of reacting with at least two entities (e.g. polypeptides) to be linked, thereby bonding the entities to form one molecule or maintaining association of the entities in sufficiently close proximity. The polypeptide linker can be integrated in the resulting linked molecule or structure. In certain embodiments, the polypeptide linker separates the GLP-1 and FGF21, without substantial interference to the respective biological activities of the GLP-1 and FGF21. The polypeptide linker can be made up of amino acid residues linked together by peptide bonds. The polypeptide linker can further comprise one or more non-natural amino acids.

In certain embodiments, the polypeptide linker has a length of at least 4, 8, 10, 20, 24, 28, 30, 40, 48, 50, 60, 70, 80, 90, 100, 110, 120 or more amino acid resides. In certain embodiments, the polypeptide linker has a length of at most 4, 8, 10, 20, 24, 28, 30, 40, 48, 50, 60, 70, 80, 90, 100, 110, or 120 amino acid resides. In certain embodiments, the polypeptide linker has a length of 0-120, 1-120, 4-120, 8-120, 10-120, 20-120, 20-110, 20-100, 20-90, or 20-80 amino acid resides. Without wishing to be bound by any theory, it is believed that a suitable length of the polypeptide linker can further improve the biological activity or stability or pharmacokinetic parameters of the linked polypeptide molecule.

Any suitable polypeptide linkers can be used. For example, the polypeptide linker may comprise or consist of amino acid residues selected from the amino acids glycine (G), serine(S), alanine (A), methionine (M), asparagine (N), glutamine (Q), cysteine (C), Proline (P), Glutamate (E), Threonine (T) and lysine (K). In some embodiments, the polypeptide linker can be made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)).

In certain embodiments, the polypeptide linker comprises or consists of one or more repeats of a repeating sequence. In certain embodiments, the polypeptide linker comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 repeats of a repeating sequence, or within any numerical range defined by any two numbers listed above.

In certain embodiments, the repeating sequence comprises or consists of no more than 4, 5 or 6 types of amino acid residues selected from the group consisting of: G, Q, A, E, P, T and S. In certain embodiments, the repeating sequence comprises Q. In certain embodiments, the repeating sequence consists no more than 3, 4 or 5 types of amino acid residues selected from the group consisting of: G, A, S, Q and P. In certain embodiments, the repeating sequence consists of G, A, Q and P. In certain embodiments, the repeat sequence consists of G, A, E, and P. In certain embodiments, the repeat sequence consists of G, A, S, and P. In certain embodiments, the repeating sequence comprises no negatively charges amino acid residues.

In certain embodiments, the repeating sequence comprises or essentially consist of amino acid residue G and S.

In certain embodiments, the repeating sequence comprises of essentially consist of an amino acid sequence selected from GS, GGSG, $G_aS_b$, $S_aG_b$ with a and b independently selected from an integer of 1 to 5. In certain embodiments, the polypeptide linker comprises of essentially consist of (GS)n, (GGSG)n, $(G_aS_b)$n, $(S_aG_b)$n, with a and b independently selected from an integer of 1 to 5, and n selected from an integer of 1 to 60.

In certain embodiments, the repeating sequence comprises or consists of an amino acid sequences selected from $G_aS_b$, SEQ ID NO: 65 (GAQP), SEQ ID NO:92 (GQEP), SEQ ID NO:93 (GEQP), SEQ ID NO: 94 (GPQE), SEQ ID NO: 95 (GPEQ), SEQ ID NO: 96 (GSEP), SEQ ID NO: 97 (GESP), SEQ ID NO: 98 (GPSE), SEQ ID NO: 99 (GPES), SEQ ID NO: 100 (GQAP), SEQ ID NO: 101 (GPAQ), SEQ ID NO: 102 (GPQA), SEQ ID NO: 103 (GSQP), SEQ ID NO: 104 (GASP), SEQ ID NO: 105 (GPAS), SEQ ID NO: 106 (GPSA), SEQ ID NO: 107 (GGGS), SEQ ID NO: 108 (GSGS), SEQ ID NO: 57 (GGGGS), SEQ ID NO: 143 (GSAPGSPAGSPTGSAPGSPA) and GS, wherein a and b are independently an integer selected from 1 to 5.

In certain embodiments, the polypeptide linker comprises or consists of a sequence selected from the group consisting of: SEQ ID NOs: 54-65, 109-113, 3, 47-49 and 141-147.

In certain embodiments, the polypeptide linker comprises or consists of more than one repeating sequence. For example, the polypeptide linker comprises or consists of 2, 3, or 4 different repeating sequences. In certain embodiments, the polypeptide linker comprises or consists of sequential or tandem repeats of the different repeating sequences. The number of repeats of each repeating sequence more be independently selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more.

In certain embodiments, the fusion polypeptide comprises, from N terminus to C terminus, GLP-1, a polypeptide linker and FGF21. In certain embodiments, the fusion polypeptide is a single chain polypeptide. A single chain polypeptide can still have intrachain bonds within the molecule but does not include complexes formed by one or more interchain bonds.

In certain embodiments, the fusion polypeptide consists essentially of, from N-terminus to C terminus, a GLP-1, a polypeptide linker and a FGF21.

In certain embodiments, the polypeptide conjugate does not comprise an antibody fragment (e.g. Fc). An antibody is an immunoglobulin molecular having the ability to specifically bind to a particular antigen. An antibody comprises two functionally independent parts, a variable domain known as "Fab", which binds antigen, and a constant domain known as "Fc", which comprises a non-antigen-binding fragment and links to such effector functions as complement activation and attack by phagocytic cells. An Fc domain has a long serum half-life.

Conjugatable Residues

The fusion polypeptide provided herein further comprises at least one conjugatable residue to which the CRM is conjugated.

The term "conjugatable residue" as used herein, refers to an amino acid residue at a particular position within the fusion polypeptide, which not only has a functional group capable of being chemically or enzymatically conjugated to a chemical moiety, but its position in the fusion polypeptide allows it to be prone to such conjugation in a conjugating reaction for that particular functional group. "Conjugation" as used herein refers to a reaction that joins two molecules together to form one physical entity. For example, a covalent bond linking the two molecules can be formed in conjugation.

A skilled person would understand that, whether a residue is conjugatable residue would depend on the given conjugating reaction, and/or the functional group to be conjugated. If the functional group to be conjugated is an amino group and/or the conjugation reaction is specific or selective for an amino group, then a cysteine residue (i.e. having no functional amino group in its side chain) would not be a conjugatable group regardless of its position in the polypeptide, whereas a lysine residue at a particular position could be. Similarly, if the function group to be conjugated is a thiol group and/or the conjugation reaction is specific or selective for a thiol group, then lysine (i.e. having no functional thiol group in its side chain) would not be the conjugatable residue regardless of its position, whereas an unpaired cysteine residue that does not form a disulfide bond (whether intrachain bond or interchain bond), could be a conjugatable residue.

In certain embodiments, the fusion polypeptide comprises a conjugatable residue for a conjugation reaction specific or selective for an amino group or amine (for example, an acylation reaction). In certain embodiments, the fusion polypeptide comprises a conjugatable residue for a conjugation reaction specific or selective for thiol group (for example, a maleimide reaction, or a reaction for disulfide bond formation).

The expression "conjugatable" when referred to an amino acid residue is intended to mean that, the residue at a particular position in the fusion polypeptide is sufficiently accessible for conjugation. For example, a cysteine residue as part of a disulfide bridge is not a conjugatable residue in the present disclosure.

A conjugatable residue can be a natural amino acid residue, a non-natural amino acid residue, modified amino acid residue or an amino acid mimetic. Examples of conjugatable residues include, without limitation, lysine, cysteine, or a non-natural amino acid residue.

The fusion polypeptide provided herein comprises at least one conjugatable residue to which the CRM is conjugated. In certain embodiments, the fusion polypeptide comprises up to one conjugatable residue. In certain embodiments, the fusion polypeptide comprises up to two conjugatable residues.

In certain embodiments, the fusion polypeptide comprises a first conjugatable residue to which the CRM is conjugated. In certain embodiments, the first conjugatable residue is in the FGF21, in the polypeptide linker or in the GLP-1. In certain embodiments, the first conjugatable residue is in the FGF21.

In certain embodiments, the fusion polypeptide comprises a first conjugatable residue and a second conjugatable residue. In certain embodiments, both the first and the second conjugatable residues are present in the same constituent component of the fusion polypeptide. For example, both the first and the second conjugatable residues are present in the FGF21, in the polypeptide linker or in the GLP-1. In certain embodiments, the first and the second conjugatable residues are present in the different constituent components of the fusion polypeptide. For example, the first conjugatable residue is present in the FGF21 whereas the second in the polypeptide linker, the first in the GLP-1 whereas the second in the FGF21, or the first in the GLP-1 whereas the second in the polypeptide linker. The terms "first" and "second" used herein are solely for the designation of one of the two conjugatable residues, and it is by no means to imply the conjugation is performed in any order between the first and the second conjugatable residues.

In certain embodiments, the conjugatable residue can be a naturally occurring residue found in the native FGF21 sequence, or a naturally occurring residue found in the native GLP-1 sequence. In certain embodiments, such a naturally occurring residue is a naturally occurring lysine residue.

In certain embodiments, when the native GLP-1 or native FGF21 has more than one naturally occurring conjugatable residue, one or more of such naturally occurring conjugatable residue can be removed for example by mutation. For example, native GLP-1 has two naturally occurring lysine residues, and native FGF21 has four naturally occurring lysine residues, and at least some of them, or all of them can be mutated, without significantly reducing the biological activity of the fusion polypeptide.

In certain embodiments, the conjugatable residue can alternatively be an introduced residue, for example, by substitution of a non-conjugatable residue to a conjugatable residue, or by insertion of a conjugatable residue. The term "non-conjugatable residue" refers to an amino acid residue in the fusion polypeptide that is not a conjugatable residue for a given functional group to be conjugated and/or for the given conjugation reaction. For example, when lysine is the conjugatable residue, any amino acid residue can be considered as a non-conjugatable residue if it does not contain an amino group and/or does not react in the conjugation reaction specific or selective for an amino group.

In certain embodiments, such an introduced conjugatable residue is lysine residue. In certain embodiments, such an introduced conjugatable residue is cysteine residue.

In certain embodiments, both the first and the second conjugatable residues are of the same chemical identity. For examples, the first and the second conjugatable residues are both lysine, both cysteine or both non-natural amino acid residue.

Conjugatable Residues in FGF21

In certain embodiments, the FGF21 comprises the first conjugatable residue. In certain embodiments, the FGF21 comprises no or up to one conjugatable residue.

In certain embodiments, the conjugatable residue in FGF21 is an introduced residue, optionally by substitution or insertion. Such introduced conjugatable residue can be introduced to a position that does not significantly reduce the biological activity of FGF21. In certain embodiments, the introduced conjugatable residue in FGF21 is the C-terminal region of the FGF21, e.g. at a position that is no more than 15, 14, 13, 12, 11, 10, 9, 8, 7, 6, 5, 4, 3, 2 or 1 amino acid residue from the most C-terminal residue, or at the position of the most C-terminal residue relative to SEQ ID NO: 36, or at the position that is extended from the most C-terminal residue relative to SEQ ID NO: 36. A C-terminal extension of FGF21 can be described by reference to SEQ ID NO: 36 by continued numbering from the 181' residue which is the most C-terminal residue in SEQ ID NO: 36. Position 182 relative to SEQ ID NO: 36 means the first residue extended from the 181' residue of SEQ ID NO: 36, i.e. from the C terminus. Similarly, position 183 means the second residue extended from the C terminus, and so on. As an example, "ins182K" relative to SEQ ID NO: 36 refers to the lysine residue attached to or inserted at the position 182 relative to SEQ ID NO: 36. In certain embodiments, the introduced conjugatable residue in FGF21 is selected from positions 170, 171, 172, 173, 174, 180, 181, 71 and 182 relative to SEQ ID NO: 36.

In certain embodiments, the conjugatable residue in FGF21 comprises or consists of lysine. In certain embodiments, the conjugatable residue in the FGF21 comprises a substitution selected from the group consisting of: G170K, P171K, S172K, Q173K, G174K, A180K, S181K, S71K and ins182K relative to SEQ ID NO: 36.

In certain embodiments, the naturally occurring lysine residues in FGF21 have been removed, by e.g. substitution of a naturally occurring lysine residue with a non-conjugatable residue or deletion of the naturally occurring lysine residues or any other means that prevents the side chain of the naturally occurring lysine residues from reacting in a given conjugation reaction.

In certain embodiments, the FGF21 comprises one or more mutations at positions selected from K56, K59, K69, and K122 relative to SEQ ID NO: 36, to a non-conjugatable residue. In certain embodiments, the non-conjugatable residue is selected from the group consisting of: Arginine (R), Glutamine (Q), Alanine (A), Glycine (G), Histidine (H), Serine (S), and Threonine (T). In certain embodiments, the FGF21 comprises substitution of K56 which is selected from the group consisting of K56R, K56Q, K56A, K56G, K56H, K56S, and K56T. In certain embodiments, the FGF21 comprises, or further comprises, substitution of K59 which selected from the group consisting of K59R, K59Q, K59A, K59G, K59H, K59S, and K59T. In certain embodiments, the FGF21 comprises, or further comprises, substitution of K69 which is selected from K69R, K69Q, K69A, K69G, K69H, K69S, and K69T. In certain embodiments, the FGF21 comprises, or further comprises, substitution of K122 which is selected from K122R, K122Q, K122A, K122G, K122H, K122S, and K122T. In certain embodiments, the FGF21 comprises mutations of K56R, K59R, K69R, and K122R.

In certain embodiments, the FGF21 comprises or consists of a combination of mutations relative to SEQ ID NO: 36 selected from the group consisting of:
1) N121Q, M168L, A180K, P171G, K56R, K59R, K69R, and K122R;
2) N121Q, M168L, P171K, K56R, K59R, K69R, and K122R;
3) N121Q, M168L, G174K, P171G, K56R, K59R, K69R, and K122R;
4) N121Q, M168L, P171K, K56R, K59R, K69R, K122R, and A180E;
5) N121Q, M168L, G174K, P171G, K56R, K59R, K69R, K122R, and A180E;
6) N121Q, M168L, A180K, K56R, K59R, K69R, and K122R;
7) N121Q, M168L, A180K, P171G, K56R, K59R, K69R, K122R, and del181S;
8) N121Q, M168L, G170K, K56R, K59R, K69R, and K122R;
9) N121Q, M168L, G170K, K56R, K59R, K69R, K122R and A180E;
10) N121Q, M168L, G170K, P171G, K56R, K59R, K69R, K122R and A180E;
11) N121Q, M168L, A180E, P171G, K56R, K59R, K69R, K122R and S181K;
12) N121Q, M168L, A180E, P171G, K56R, K59R, K69R, K122R, and ins182K;
13) 71K, 121Q, 168L, 56R, 59R, 69R, and 122R;
14) 71K, 121Q, 168L, 171G, 56R, 59R, 69R, and 122R; and
15) 71K, 121Q, 168L, 171G, 56R, 59R, 69R, 122R, 180E.

In certain embodiments, the FGF21 comprises or consists of an amino acid sequence selected from the group consisting of: SEQ ID NO: 37-46 and 118-119.

In certain embodiments, the conjugatable residue in FGF21 comprises or consists of cysteine.

Without wishing to be bound by any theory, but it is believed that cysteine residues at position 75 and 93 in the FGF21 relative to SEQ ID NO: 36 are non-conjugatable residues. The two cysteine residues form an intramolecular disulfide bond in the mature FGF21 and are therefore not accessible for conjugating agents in a conjugation reaction. Accordingly, the FGF21 having cysteine residues only at positions 75 and 93 are considered as comprising no conjugatable residue for thiol group conjugation reaction.

In certain embodiments, the conjugatable residue in the FGF21 comprises a substitution selected from the group consisting of: G170C, P171C, S172C, Q173C, G174C, A180C, S181C, S71C and ins182C relative to SEQ ID NO: 36.

In certain embodiments, the conjugatable residue in FGF21 comprises or consists of a non-natural amino acid. Non-natural amino acid can contain a variety of functional groups or reactive groups, which can provide for additional functions and/or reactivity. Particular non-natural amino acids that are beneficial for purpose of conjugating moieties to the fusion polypeptides of the present disclosure include those with a side chain having azide, alkyne, alkene, cycloalkyne or halide.

In certain embodiments, the FGF21 comprises or consists of a combination of mutations relative to SEQ ID NO: 36 selected from the group consisting of:
1) 121Q, 168L, 171C, 180E;
2) 121Q, 168L, 171G, 174C, 180E;
3) 121Q, 168L, 171G, 180C;
4) 121Q, 168L, 171G, 180E;
5) S71C, 121Q, 168L, 171G, 180E; and
6) 121Q, 168L, 180E, 171G, ins 182C.

In certain embodiments, the FGF21 comprises no conjugatable residue. In certain embodiments, the FGF21 comprises mutations 121Q, 168L, 171G and 180E relative to SEQ ID NO: 36.

In certain embodiments, the FGF21 comprises or consists of an amino acid sequence selected from the group consisting of: SEQ ID NO:136-140 and 171.

Conjugatable Residues in GLP-1

In certain embodiments, the GLP-1 comprises no conjugatable residue or up to one conjugatable residue. In certain embodiments, the FGF21 comprises the first conjugatable residue, and the GLP-1 comprises the second conjugatable residue.

In certain embodiments, the conjugatable residue in GLP-1 is a naturally occurring amino acid residue. In certain embodiments, the conjugatable residue in GLP-1 comprises or consists of lysine.

The native GLP-1 peptide, as set forth in SEQ ID NO: 50, has two naturally occurring lysine (K) residues, namely K26 and K34. In certain embodiments, the conjugatable residue in the GLP-1 is a naturally occurring residue found in the native GLP-1 peptide, for example, K26 or K34.

In certain embodiments, the conjugatable residue in the GLP-1 comprises an introduced residue, for example, by substitution of a non-conjugatable residue to a conjugatable residue, or by insertion of a conjugatable residue (for example at the N terminus or C terminus of the GLP-1 or within the GLP-1 sequence). Any non-conjugatable residue in GLP-1 can be substituted with a conjugatable residue, as long as such substitution does not substantially diminish the biological activity of the GLP-1 or the fusion polypeptide.

In certain embodiments, the conjugatable residue in the GLP-1 is introduced by a substitution at E27 or R36 in the GLP-1, relative to SEQ ID NO: 50. In certain embodiments, the conjugatable residue in the GLP-1 is introduced by a substitution selected from the group consisting of: E27K and R36K. In such embodiments, the GLP-1 further comprises substitution of K26 and/or K34 to a non-conjugatable residue.

In certain embodiments, one of or both of the naturally occurring lysine residues in GLP-1 have been removed, by e.g. substitution of a naturally occurring lysine residue with a non-conjugatable residue or deletion of the naturally occurring lysine residues or any other means that prevents the side chain of the naturally occurring lysine residues from reacting in a given conjugation reaction.

In certain embodiments, the GLP-1 further comprises substitution of K26 and/or K34 to a non-conjugatable residue. In certain embodiments, for lysine conjugation reaction, the non-conjugatable residue is optionally selected from the group consisting of Arginine (R), Glutamine (Q), Alanine (A), Glycine (G), Histidine (H), Serine (S), and Threonine (T).

In certain embodiments, the GLP-1 comprises substitution of K26 which is selected from the group consisting of K26R, K26Q, K26A, K26G, K26H, K26S, and K26T. In certain embodiments, the GLP-1 comprises, or further comprises, substitution of K34 which selected from the group consisting of K34R, K34Q, K34A, K34G, K34H, K34S, and K34T. In certain embodiments, the substitution of K26 is selected from K26R and K26Q, and/or the substitution at K34 is selected from K34R and K34Q. In certain embodiments, the GLP-1 comprises K26R, and/or K34R, relative to SEQ ID NO: 50.

In certain embodiments, the conjugatable residue in the GLP-1 comprises a cysteine residue.

In certain embodiments, the conjugatable residue in the GLP-1 is a non-natural amino acid residue (NNAA).

In certain embodiments, the cysteine residue or the NNAA in the GLP-1 is introduced by a substitution at the position selected from the group consisting of: K26, K34, E27 and R36, relative to SEQ ID NO: 50. In certain embodiments, the cysteine residue or the NNAA in the GLP-1 is introduced by a substitution at the position selected from the group consisting of: K26, E27 and R36, relative to SEQ ID NO: 50.

In certain embodiments, the GLP-1 comprises an amino acid sequence of $X_7X_8$EGTFTSDVSSYLE$X_{22}$QAA$X_{26}X_{27}$FIAWLV$X_{34}$G$X_{36}$G (SEQ ID NO: 51), wherein: the $X_7$ is H, IA or IPA; $X_8$ is A, G, S, V, Aib, T, I or L; the $X_{22}$ is G, or E; the $X_{26}$ is K, R, or C; the $X_{27}$ is E, K, or C; the $X_{34}$ is R, K, or C, and the $X_{36}$ is K, R, G, or C, provided that the GLP-1 has up to one lysine residue (K) or up to one cysteine (C) in the amino acid sequence.

In certain embodiments, the $X_7$ is H, the $X_8$ is G, the $X_{22}$ is E; the $X_{26}$ is K, R or C; the $X_{27}$ is E, K or C; the $X_{34}$ is R, K or C, and the $X_{36}$ is K, R, C or G, provided that the GLP-1 has up to one lysine residue (K) or up to one cysteine residue (C) in the amino acid sequence.

In certain embodiments, the $X_7$ is H, the $X_8$ is G, the $X_{22}$ is E; the $X_{26}$ is K, or R; the $X_{27}$ is E; the $X_{34}$ is R, and the $X_{36}$ is K, or G, provided that the GLP-1 has up to one lysine residue (K) in the amino acid sequence.

In certain embodiments, the GLP-1 comprises an amino acid sequence selected from the group consisting of: SEQ ID NO: 52, 53 and 115.

In certain embodiments, the GLP-1 comprises an amino acid sequence selected from the group consisting of: SEQ ID NO: 120 or 52.

In certain embodiments, the GLP-1 comprises no conjugatable residue. In certain embodiments, the GLP-1 comprises no lysine, no cysteine, and/or no non-natural amino acid residue.

Conjugatable Residues in the Linker

In certain embodiments, the polypeptide linker comprises up to one or up to two conjugatable residues and the FGF21 or GLP-1 comprises no conjugatable residue. In certain embodiments, the FGF21 comprises the first conjugatable residue and the polypeptide linker comprises the second conjugatable residue.

The conjugatable residue can be introduced to the linker sequence by, for example, substitution or insertion. In certain embodiments, a non-conjugatable amino acid residue in the polypeptide linker is substituted with a conjugatable residue. In certain embodiments, a conjugatable residue is inserted into the polypeptide linker. For example, the second conjugatable residue can be inserted within one repeat of the repeating sequences, between two repeats of the repeating sequences, or inserted at the N terminal or C terminal of the polypeptide linker.

In certain embodiments, the conjugatable residue is introduced at any suitable position in the polypeptide linker. In certain embodiments, the conjugatable residue is introduced in the polypeptide linker at a position that is at least 2, 3, 4, 5, 6, 7, 8, 9, 10, 11, 12, 13, 14, 15, 16, 17, 18, 19, 20, 21, 22, 23, 24, 25, 30, 40, 50, 60, 70 residues away (inclusive of conjugatable residue) from the most N terminal residue of the FGF21. In certain embodiments, the conjugatable residue is introduced in the polypeptide linker at a position that is at most 2, 3, 4, 5, 6, 7, 8, 9, 10, 11, 12, 13, 14, 15, 16, 17, 18, 19, 20, 21, 22, 23, 24, 25, 30, 40, 50, 60, 70 residues away (inclusive of conjugatable residue) from the most N terminal residue of the FGF21. In certain embodiments, the conjugatable residue is introduced in the polypeptide linker at the position of the most C-terminal residue of the polypeptide linker. In certain embodiments, the conjugatable residue is introduced in the polypeptide linker at the position of that is at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 residues way (inclusive of the conjugatable residue) from the most C-terminal residue of GLP-1. In certain embodiments, the conjugatable residue is introduced in the polypeptide linker at the position of that is at most 2, 3, 4, 5, 6, 7, 8, 9, 10, 11, 12, 13, 14, 15, 16, 17, 18, 19, 20, 21, 22, 23, 24, 25, 26, 27, 28, 29 or 30 residues way (inclusive of the conjugatable residue) from the most C-terminal residue of GLP-1.

In one embodiments, the polypeptide linker comprises a substitution with a conjugatable residue which is lysine. Alternatively, the polypeptide linker comprises a substitution with a conjugatable residue which is cysteine, or a non-natural amino acid residue. In one embodiments, the conjugatable residue in the polypeptide linker is a lysine residue introduced by substation at the position of most C-terminal residue of the polypeptide linker.

In certain embodiments, the conjugatable residue in the polypeptide linker in lysine and the polypeptide linker comprises or consists of an amino acid sequence selected from the group consisting of: SEQ ID NO: 66-75 and 89-91. Alternatively, the lysine residue in each of these exemplary polypeptide linkers (i.e. SEQ ID NO: 66-75 and 89-91) can be substituted with cysteine, or a non-natural amino acid residue.

In certain embodiments, the conjugatable residue in the polypeptide linker in cysteine and the polypeptide linker comprises or consists of an amino acid sequence selected from the group consisting of: SEQ ID NO:121-134. In certain embodiments, the polypeptide linker comprises two conjugatable residues and the polypeptide linker comprises or consists of an amino acid sequence selected from the group consisting of: SEQ ID NO: 133 or 134. Alternatively, the cysteine residue in each of these exemplary polypeptide linkers (i.e. SEQ ID NO: 121-134) can be substituted with lysine, or a non-natural amino acid residue.

In certain embodiments, the fusion polypeptide comprises up to one conjugatable residue. In some embodiments, the single conjugatable residue is in the FGF21 at a position selected from positions 170, 171, 172, 173, 174, 180, 181, 71 and 182 relative to SEQ ID NO: 36. In some embodiments, the single conjugatable residue is in the polypeptide linker, e.g., at the position that is at least 5, 6, 7, 8, 9, 10, 11, 12, 13, 14, 15, 16, 17, 18, 19, or 20 residues (inclusive of the conjugatable residue) away from the most C-terminal residue of GLP-1.

In certain embodiments, the fusion polypeptide comprises up to two conjugatable residues. In such embodiments, the first conjugatable residue is in the FGF21 at a position selected from positions 170, 171, 172, 173, 174, 180, 181, 71 and 182 relative to SEQ ID NO: 36, and the second conjugatable residue is in the polypeptide linker at the position of the most C-terminal residue of the polypeptide linker or is at least 5, 6, 7, 8, 9, 10, 11, 12, 13, 14, 15, 16, 17, 18, 19, or 20 residues way (inclusive of the conjugatable residue) from the most C-terminal residue of the GLP-1, or in the GLP-1 at a position selected from positions 26, 34, 27, and 36, relative to SEQ ID NO: 50. In some embodiments, the first conjugatable residue is in the polypeptide linker and at the C-terminus of the polypeptide linker, and the second conjugatable residue is also in the polypeptide linker at a position that is at least 2, 3, 4, 5, 6, 7, 8, 9, 10, 11, 12, 13, 14, 15, 16, 17, 18, 19, 20, 21, 22, 23, 24, 25, 30, 40, 50, 60, 70 residues way (inclusive of the conjugatable residue) from the most N-terminal residue of the FGF21. In some embodiments, the first conjugatable residue is in the polypeptide linker and at the C-terminus of the polypeptide linker, and the second conjugatable residue is also in the polypeptide linker at a position that is at or closed to the center of the polypeptide linker. In some embodiments, both the first and second conjugatable residue are in the polypeptide linker, and independently at positions that are at least 5, 6, 7, 8, 9, 10, 11, 12, 13, 14, 15, 16, 17, 18, 19, 20 residues way (inclusive of the conjugatable residue) from the most C-terminal residue of GLP-1.

In certain embodiments, the fusion polypeptide provided herein comprises an amino acid sequence selected from the group consisting of: SEQ ID NO: 2, 4-22, 24, 26-35, 77-88 and 116-117, in which the conjugated residue is lysine. Table 1A below shows the SEQ ID NOs the exemplary fusion polypeptide sequences, and the SEQ ID NOs for the FGF21, polypeptide linker and GLP-1 sequences contained in the fusion polypeptides. Table 1A below also shows the mutations in the GLP-1 and in the FGF21, as well as the repeating sequences and number of repeats in the polypeptide linker sequences.

TABLE 1A

Exemplary fusion polypeptide sequences

| SEQ ID NO: | Mutations in GLP-1** | Polypeptide Linker | Mutations in FGF21# |
|---|---|---|---|
| 2 | 8G, 22E, 34R, 36G (SEQ ID NO: 52) | (G4S)4 (SEQ ID NO: 54) | 121Q, 168L, 180K, 171G, 56R, 59R, 69R, 122R (SEQ ID NO: 37) |
| 4 | 8G, 22E, 26R, 34R, 36G (SEQ ID NO: 53) | (G4S)3G4K (SEQ ID NO: 66) | 121Q, 168L, 180K, 171G, 56R, 59R, 69R, 122R (SEQ ID NO: 37) |
| 5 | 8G, 22E, 26R, 34R, 36G (SEQ ID NO: 53) | (G4S)3G4K (SEQ ID NO: 66) | 121Q, 168L, 171K, 56R, 59R, 69R, 122R (SEQ ID NO: 38) |
| 6 | 8G, 22E, 26R, 34R, 36G (SEQ ID NO: 53) | (G4S)4 (SEQ ID NO: 54) | 121Q, 168L, 171K, 56R, 59R, 69R, 122R (SEQ ID NO: 38) |
| 7 | 8G, 22E, 26R, 34R, 36G (SEQ ID NO: 53) | (G4S)4 (SEQ ID NO: 54) | 121Q, 168L, 170K, 56R, 59R, 69R, 122R (SEQ ID NO: 39) |
| 8 | 8G, 22E, 26R, 34R, 36G (SEQ ID NO: 53) | (G4S)4 (SEQ ID NO: 54) | 121Q, 168L, 174K, 171G, 56R, 59R, 69R, 122R (SEQ ID NO: 40) |
| 9 | 8G, 22E, 26R, 34R, 36G (SEQ ID NO: 53) | (G4S)4 (SEQ ID NO: 54) | 121Q, 168L, 180K, 171G, 56R, 59R, 69R, 122R (SEQ ID NO: 37) |
| 10 | 8G, 22E, 26R, 34R, 36G (SEQ ID NO: 53) | (G4S)4 (SEQ ID NO: 54) | 121Q, 168L, 171K, 56R, 59R, 69R, 122R, 180E (SEQ ID NO: 41) |
| 11 | 8G, 22E, 26R, 34R, 36G (SEQ ID NO: 53) | (G4S)4 (SEQ ID NO: 54) | 121Q, 168L, 170K, 56R, 59R, 69R, 122R, 180E (SEQ ID NO: 42) |
| 12 | 8G, 22E, 26R, 34R, 36G (SEQ ID NO: 53) | (G4S)4 (SEQ ID NO: 54) | 121Q, 168L, 174K, 171G, 56R, 59R, 69R, 122R, 180E (SEQ ID NO: 43) |
| 13 | 8G, 22E, 26R, 34R, 36G (SEQ ID NO: 53) | (GAQP)5 (SEQ ID NO: 55) | 121Q, 168L, 171K, 56R, 59R, 69R, 122R, 180E (SEQ ID NO: 41) |
| 14 | 8G, 22E, 26R, 34R, 36G (SEQ ID NO: 53) | (GQEP)5 (SEQ ID NO: 56) | 121Q, 168L, 171K, 56R, 59R, 69R, 122R, 180E (SEQ ID NO: 41) |

TABLE 1A-continued

Exemplary fusion polypeptide sequences

| SEQ ID NO: | Mutations in GLP-1** | Polypeptide Linker | Mutations in FGF21# |
|---|---|---|---|
| 15 | 8G, 22E, 26R, 34R, 36G (SEQ ID NO: 53) | (G4S)4 (SEQ ID NO: 54) | 121Q, 168L, 180K, 56R, 59R, 69R, 122R (SEQ ID NO: 44) |
| 16 | 8G, 22E, 34R, 36G (SEQ ID NO: 52) | (G4S)4 (SEQ ID NO: 54) | 121Q, 168L, 171K, 56R, 59R, 69R, 122R, 180E (SEQ ID NO: 41) |
| 17 | 8G, 22E, 34R, 36G (SEQ ID NO: 52) | (G4S)4 (SEQ ID NO: 54) | 121Q, 168L, 170K, 56R, 59R, 69R, 122R, 180E (SEQ ID NO: 42) |
| 18 | 8G, 22E, 34R, 36G (SEQ ID NO: 52) | (G4S)4 (SEQ ID NO: 54) | 121Q, 168L, 171G, 174K, 56R, 59R, 69R, 122R, 180E (SEQ ID NO: 43) |
| 19 | 8G, 22E, 26R, 34R, 36G (SEQ ID NO: 53) | (G4S)3G4K (SEQ ID NO: 66) | 121Q, 168L, 171K, 56R, 59R, 69R, 122R, 180E (SEQ ID NO: 41) |
| 20 | 8G, 22E, 26R, 34R, 36G (SEQ ID NO: 53) | (G4S)3G4K (SEQ ID NO: 66) | 121Q, 168L, 170K, 56R, 59R, 69R, 122R, 180E (SEQ ID NO: 42) |
| 21 | 8G, 22E, 26R, 34R, 36G (SEQ ID NO: 53) | (G4S)3G4K (SEQ ID NO: 66) | 121Q, 168L, 171G, 174K, 56R, 59R, 69R, 122R, 180E (SEQ ID NO: 43) |
| 22 | 8G, 22E, 26R, 34R, 36G (SEQ ID NO: 53) | (G4S)3G4K (SEQ ID NO: 66) | 121Q, 168L, 180K, 171G, 56R, 59R, 69R, 122R, del181S (SEQ ID NO: 45) |
| 24 | 8G, 22E, 26R, 34R, 36G (SEQ ID NO: 53) | (G4S)3G4K (SEQ ID NO: 66) | 121Q, 168L, 170K, 171G, 56R, 59R, 69R, 122R, 180E (SEQ ID NO: 46) |
| 26 | 8G, 22E, 26R, 34R, 36G (SEQ ID NO: 53) | G4K (SEQ ID NO: 67) | 121Q, 168L, 171G, 174K, 56R, 59R, 69R, 122R, 180E (SEQ ID NO: 43) |
| 27 | 8G, 22E, 26R, 34R, 36G (SEQ ID NO: 53) | (G4S)G4K (SEQ ID NO: 68) | 121Q, 168L, 171G, 174K, 56R, 59R, 69R, 122R, 180E (SEQ ID NO: 43) |
| 28 | 8G, 22E, 26R, 34R, 36G (SEQ ID NO: 53) | (G4S)7G4K (SEQ ID NO: 69) | 121Q, 168L, 171G, 174K, 56R, 59R, 69R, 122R, 180E (SEQ ID NO: 43) |
| 29 | 8G, 22E, 26R, 34R, 36G (SEQ ID NO: 53) | (GAQP)19GAQK (SEQ ID NO: 70) | 121Q, 168L, 171G, 174K, 56R, 59R, 69R, 122R, 180E (SEQ ID NO: 43) |
| 30 | 8G, 22E, 26R, 34R, 36G (SEQ ID NO: 53) | (GAQP)4GAQK (SEQ ID NO: 71) | 121Q, 168L, 171G, 174K, 56R, 59R, 69R, 122R, 180E (SEQ ID NO: 43) |
| 31 | 8G, 22E, 26R, 34R, 36G (SEQ ID NO: 53) | (GAQP)11GAQK (SEQ ID NO: 72) | 121Q, 168L, 171G, 174K, 56R, 59R, 69R, 122R, 180E (SEQ ID NO: 43) |
| 32 | 8G, 22E, 26R, 34R, 36G (SEQ ID NO: 53) | (GAQP)9GAQK (SEQ ID NO: 73) | 121Q, 168L, 171G, 174K, 56R, 59R, 69R, 122R, 180E (SEQ ID NO: 43) |
| 33 | 8G, 22E, 26R, 34R, 36G (SEQ ID NO: 53) | (GAQP)GAQK (SEQ ID NO: 74) | 121Q, 168L, 171G, 174K, 56R, 59R, 69R, 122R, 180E (SEQ ID NO: 43) |
| 34 | 8G, 22E, 26R, 34R, 36G (SEQ ID NO: 53) | GAQK (SEQ ID NO: 75) | 121Q, 168L, 171G, 174K, 56R, 59R, 69R, 122R, 180E (SEQ ID NO: 43) |
| 35 | 8G, 22E, 34R, 36G (SEQ ID NO: 52) | (G4S)4 (SEQ ID NO: 54) | 121Q, 168L, 170K, 171G, 56R, 59R, 69R, 122R, 180E (SEQ ID NO: 46) |
| 77 | 8G, 22E, 26R, 34R, 36G (SEQ ID NO: 53) | G4K (SEQ ID NO: 67) | 121Q, 168L, 171K, 56R, 59R, 69R, 122R, 180E (SEQ ID NO; 41) |
| 78 | 8G, 22E, 26R, 34R, 36G (SEQ ID NO: 53) | (G4S)G4K (SEQ ID NO: 68) | 121Q, 168L, 171K, 56R, 59R, 69R, 122R, 180E (SEQ ID NO; 41) |
| 79 | 8G, 22E, 26R, 34R, 36G (SEQ ID NO: 53) | (G4S)7G4K (SEQ ID NO: 69) | 121Q, 168L, 171K, 56R, 59R, 69R, 122R, 180E (SEQ ID NO; 41) |
| 80 | 8G, 22E, 26R, 34R, 36G (SEQ ID NO: 53) | (GAQP)19GAQK (SEQ ID NO: 70) | 121Q, 168L, 171K, 56R, 59R, 69R, 122R, 180E (SEQ ID NO; 41) |
| 81 | 8G, 22E, 26R, 34R, 36G (SEQ ID NO: 53) | (GAQP)11GAQK (SEQ ID NO: 72) | 121Q, 168L, 171K, 56R, 59R, 69R, 122R, 180E (SEQ ID NO; 41) |
| 82 | 8G, 22E, 26R, 34R, 36G (SEQ ID NO: 53) | (GAQP)9GAQK (SEQ ID NO: 73) | 121Q, 168L, 171K, 56R, 59R, 69R, 122R, 180E (SEQ ID NO; 41) |

TABLE 1A-continued

Exemplary fusion polypeptide sequences

| SEQ ID NO: | Mutations in GLP-1** | Polypeptide Linker | Mutations in FGF21# |
|---|---|---|---|
| 83 | 8G, 22E, 26R, 34R, 36G (SEQ ID NO: 53) | (GAQP)GAQK (SEQ ID NO: 74) | 121Q, 168L, 171K, 56R, 59R, 69R, 122R, 180E (SEQ ID NO; 41) |
| 84 | 8G, 22E, 26R, 34R, 36G (SEQ ID NO: 53) | GAQK (SEQ ID NO: 75) | 121Q, 168L, 171K, 56R, 59R, 69R, 122R, 180E (SEQ ID NO; 41) |
| 85 | 8G, 22E, 26R, 34R, 36G (SEQ ID NO: 53) | (G4S)2(G4K)(G4S) (SEQ ID NO: 89) | 121Q, 168L, 171K, 56R, 59R, 69R, 122R, 180E (SEQ ID NO; 41) |
| 86 | 8G, 22E, 26R, 34R, 36G (SEQ ID NO: 53) | (G4S)(G4K)(G4S)2 (SEQ ID NO: 90) | 121Q, 168L, 171K, 56R, 59R, 69R, 122R, 180E (SEQ ID NO; 41) |
| 87 | 8G, 22E, 26R, 34R, 36G (SEQ ID NO: 53) | (G4K)(G4S)3 (SEQ ID NO: 91) | 121Q, 168L, 171K, 56R, 59R, 69R, 122R, 180E (SEQ ID NO; 41) |
| 88 | 8G, 22E, 26R, 34R, 36G (SEQ ID NO: 53) | (GAQP)4GAQK (SEQ ID NO: 71) | 121Q, 168L, 171K, 56R, 59R, 69R, 122R, 180E (SEQ ID NO; 41) |
| 116 | 8G, 22E, 26R, 34R, 36G (SEQ ID NO: 53) | (G4S)3G4K (SEQ ID NO: 66) | 121Q, 168L, 180E, 171G, 56R, 59R, 69R, 122R, 181K (SEQ ID NO: 118) |
| 117 | 8G, 22E, 26R, 34R, 36G (SEQ ID NO: 53) | (G4S)3G4K (SEQ ID NO: 66) | 121Q, 168L, 180E, 171G, 56R, 59R, 69R, 122R, ins182K (SEQ ID NO: 119) |

**Mutations in GLP-1 means mutations relative to SEQ ID NO: 50;
Mutations in FGF21 means mutations relative to SEQ ID NO: 36;

In certain embodiments, the fusion polypeptide provided herein comprises an amino acid sequence selected from the group consisting of: SEQ ID NO: 148-165, 168-170, 1, 23, 25, and 76, in which the conjugatable residue is cysteine. Table 1B below shows the SEQ ID NOs the exemplary fusion polypeptide sequences, and the SEQ ID NOs for the FGF21, polypeptide linker and GLP-1 sequences contained in the fusion polypeptides. Table 1B below also shows the mutations in the GLP-1 and in the FGF21, as well as the repeating sequences and number of repeats in the polypeptide linker sequences.

TABLE 1B

Exemplary fusion polypeptide sequences

| SEQ ID NO: | Mutations in GLP-1** | Polypeptide Linker | Mutations in FGF21# |
|---|---|---|---|
| 148 | 8G, 22E, 34R,36 G (SEQ ID NO: 52) | (G4S)3G4C (SEQ ID NO: 122) | 121Q, 168L, 171C, 180E (SEQ ID NO: 136) |
| 149 | 8G, 22E, 34R, 36G (SEQ ID NO: 52) | (G4S)3G4C (SEQ ID NO: 122) | 121Q, 168L, 171G, 174C, 180E (SEQ ID NO: 137) |
| 150 | 8G, 22E, 34R, 36G (SEQ ID NO: 52) | (G4S)3G4C (SEQ ID NO: 122) | 121Q, 168L, 180E, 171G, ins182C (SEQ ID NO: 140) |
| 151 | 8G, 22E, 34R, 36G (SEQ ID NO: 52) | (G4S)3G4C (SEQ ID NO: 122) | 121Q, 168L, 171G, 180C (SEQ ID NO: 138) |
| 152 | 8G, 22E, 34R, 36G (SEQ ID NO: 52) | (GAQP)4GAQC (SEQ ID NO: 123) | 121Q, 168L, 171C, 180E (SEQ ID NO: 136) |
| 153 | 8G, 22E, 34R, 36G (SEQ ID NO: 52) | (GAQP)4GAQC (SEQ ID NO: 123) | 121Q, 168L, 171G, 174C, 180E (SEQ ID NO: 137) |
| 154 | 8G, 22E, 34R, 36G (SEQ ID NO: 52) | (GAQP)4GAQC (SEQ ID NO: 123) | 121Q, 168L, 171G, 180C (SEQ ID NO: 138) |
| 155 | 8G, 22E, 34R, 36G (SEQ ID NO: 52) | (GAQP)5GAQC (SEQ ID NO: 124) | 121Q, 168L, 171G, 174C, 180E (SEQ ID NO: 137) |
| 156 | 8G, 22E, 34R, 36G (SEQ ID NO: 52) | (GAQP)6GAQC (SEQ ID NO: 125) | 121Q, 168L, 171G, 174C, 180E (SEQ ID NO: 137) |
| 157 | 8G, 22E, 36G (SEQ ID NO: 120) | (G4S)3G4C (SEQ ID NO: 122) | 121Q, 168L, 171G, 174C, 180E (SEQ ID NO: 137) |
| 158 | 8G, 22E, 36G (SEQ ID NO: 120) | (G4S)2G4CG4S (SEQ ID NO: 126) | 121Q, 168L, 171G, 174C, 180E (SEQ ID NO: 137) |
| 159 | 8G, 22E, 36G (SEQ ID NO: 120) | (G4S)G4C(G4S)2 (SEQ ID NO: 127) | 121Q, 168L, 171G, 174C, 180E (SEQ ID NO: 137) |
| 160 | 8G, 22E, 36G (SEQ ID NO: 120) | (G4S)3G4C (SEQ ID NO: 122) | 121Q, 168L, 171C, 180E (SEQ ID NO: 136) |
| 161 | 8G, 22E, 36G (SEQ ID NO: 120) | (G4S)2G4CG4S (SEQ ID NO: 126) | 121Q, 168L, 171C, 180E (SEQ ID NO: 136) |

TABLE 1B-continued

Exemplary fusion polypeptide sequences

| SEQ ID NO: | Mutations in GLP-1** | Polypeptide Linker | Mutations in FGF21# |
|---|---|---|---|
| 162 | 8G, 22E, 36G (SEQ ID NO: 120) | (G4S)G4C(G4S)2 (SEQ ID NO: 127) | 121Q, 168L, 171C, 180E (SEQ ID NO: 136) |
| 163 | 8G, 22E, 36G (SEQ ID NO: 120) | GSAPGSPAGSPTGSAPGSPC (SEQ ID NO: 128) | 121Q, 168L, 171G, 174C, 180E (SEQ ID NO: 137) |
| 164 | 8G, 22E, 36G (SEQ ID NO: 120) | (G4S)2G4C(G4S)3 (SEQ ID NO: 129) | 121Q, 168L, 171G, 174C, 180E (SEQ ID NO: 137) |
| 165 | 8G, 22E, 36G (SEQ ID NO: 120) | GSAPGSPAGSPTGSAPGSPC (SEQ ID NO: 128) | 121Q, 168L, 171C, 180E (SEQ ID NO: 136) |
| 166§ | 22E, 36G, del7-8 (SEQ ID NO: 121) | (G4S)3G4C (SEQ ID NO: 122) | 121Q, 168L, 171C, 180E (SEQ ID NO: 136) |
| 167§ | 8G, 22E, 36G (SEQ ID NO: 120) | (G4S)3G4C (SEQ ID NO: 122) | 121Q, 168C, del169-181 (SEQ ID NO: 135) |
| 168 | 8G, 22E, 36G (SEQ ID NO: 120) | (GAQP)5CQAP(GAQP)14 (SEQ ID NO: 130) | 121Q, 168L, 171C, 180E (SEQ ID NO: 136) |
| 169 | 8G, 22E, 36G (SEQ ID NO: 120) | (GAQP)7GQCP(GAQP)12 (SEQ ID NO: 131) | 121Q, 168L, 171C, 180E (SEQ ID NO: 136) |
| 170 | 8G, 22E, 36G (SEQ ID NO: 120) | (GAQP)2GQCP(GAQP)17 (SEQ ID NO: 132) | 121Q, 168L, 171C, 180E (SEQ ID NO: 136) |
| 1 | 8G, 22E, 36G (SEQ ID NO: 120) | (G4S)3G4C (SEQ ID NO: 122) | S71C, 121Q, 168L, 171G, 180E (SEQ ID NO: 171) |
| 23 | 8G, 22E, 36G (SEQ ID NO: 120) | G4S(GGGCS)G4SGGGGC (SEQ ID NO: 133) | 121Q, 168L, 171G, 180E (SEQ ID NO: 139) |
| 25 | 8G, 22E, 36G (SEQ ID NO: 120) | (G4S)3G4C (SEQ ID NO: 122) | 121Q, 168L, 171G, 180E (SEQ ID NO: 139) |
| 76 | 8G, 22E, 36G (SEQ ID NO: 120) | (G4S)3GGGCS(G4S)3G4C (SEQ ID NO: 134) | 121Q, 168L, 171G, 180E (SEQ ID NO: 139) |

**Mutations in GLP-1 means mutations relative to SEQ ID NO: 50;
Mutations in FGF21 means mutations relative to SEQ ID NO: 36;
§Fusion polypeptides having an amino acid sequence of SEQ ID NOs: 166 and 167 comprise inactive GLP-1 or inactive FGF21, and serve as negative control.

Clearance-Modifying Moiety

The present disclosure provides a polypeptide conjugate comprising a fusion polypeptide provided herein conjugated to at least one clearance reducing moiety (CRM).

The term "conjugate" as used herein refers to a compound as a result of two or more molecules joined together to form one physical entity. For example, the polypeptide conjugate of the present disclosure means a compound as a result of the fusion polypeptide and one or more clearance-modifying moieties joined together. The molecules may attach together by covalent bonds, non-covalent bonds, linkers, chemical modification, or protein fusion or by any means known to one skilled in the art. Preferably, the molecules may attach together by covalent bonds. The attachment may be permanent or reversible. In some embodiments, certain cleavable or non-cleavable linkers may be included.

The term "clearance-modifying moiety" or "CRM" as used herein refers to moiety that can alter one or more pharmacokinetic (PK) properties (for example, to increase the half-life in vivo). Examples of CRMs can include, without limitation, polyethylene glycol (PEG), glucuronic acid or other sugar based groups, polar, positively or negatively charged groups that can increase the rates of hydrolysis of a succinimidyl ring and reduce or minimize the rate of reverse Michael reaction, and therefore reduce or minimize the rate of loss of fusion polypeptide.

In certain embodiments, the CRM comprises a plasma protein-binding moiety, a polymer, human serum albumin (HSA) and functional fragments thereof, Xten sequence, or PAS sequence. In certain embodiments, the Xten sequence is an extended recombinant polypeptide sequence with an amino acid sequence described in WO2007103515, WO2009023270, WO2010091122, WO2011123813, WO2013130683, WO2017146979, WO2011084808, WO2013040093, WO2013122617, WO2014011819, WO2013184216, WO2014164568, WO2015023891, WO2016077505 and WO2017040344, disclosures of which have been incorporated by their entirety. In certain embodiments, the term "PAS", which can also be used interchangeable with the term "APS", refers to an amino acid repeats consisting of Ala, Ser, and Pro residues, as described in U.S. Pat. No. 8,563,521B2, disclosure of which has been incorporated by its entirety.

In certain embodiments, the CRM comprises an albumin-binding moiety. The term "albumin-binding moiety" refers to any functional moiety that is capable of binding albumin (e.g. human serum albumin) or any functional fragment thereof with sufficient specificity, preferably non-covalently. The albumin-binding moiety attached to a therapeutic fusion polypeptide, polypeptide, or polypeptide complex typically has an affinity below 10 μM to human serum albumin and preferably below 1 pM. The albumin-binding moiety can include, without limitation, an albumin-binding domain, an albumin-binding sequences from synthetic peptides, and an albumin-binding chemical moiety. For example, the albumin-binding moiety is selected from an albumin-binding domain from streptococcal protein G, an albumin-binding domain from *Peptostreptococcus magnus* protein PAB, an albumin-binding peptide having the core sequence DICL-PRWGCLW (SEQ ID NO: 114). A number of small peptides which are albumin binding moieties have been described in J. Biol Chem. 277, 38 (2002) 35035-35043. For another example, the albumin-binding moiety is selected from linear and branched lipohophillic moieties containing 4-40 carbon atoms, compounds with a cyclopentanophenanthrene skeleton etc. For example, the albumin-binding moiety is a group of the formula $CH_3$ $(CH_2)_v CO-NHCH(COOH)$ $(CH_2)_2 CO-$, wherein v is an integer of from 10 to 24.

In certain embodiments, the albumin-binding moiety comprises a structure of: *-A-B-C-D-E, wherein A, B, C, D and E are interconnected via amide bonds, and the * end of A is connected to the conjugatable residue on the polypeptide complex, and wherein:
A is selected from a bond,

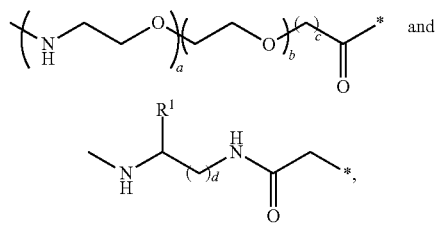

a, b, c and d are independently an integer from 0 to 4, $R^1$ is hydrogen or —COOH;
B is selected from a bond,

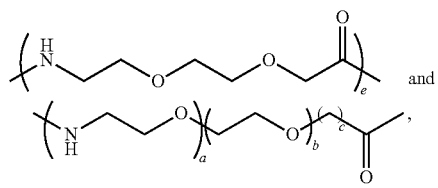

e is an integer from 1 to 4,
C is a bond or

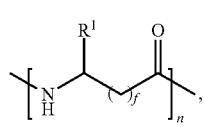

$R^2$ is —CH$_2$SO$_3$H or —COOH, f is an integer from 1 to 4, n is an integer from 1 to 25;
D is selected from a bond,

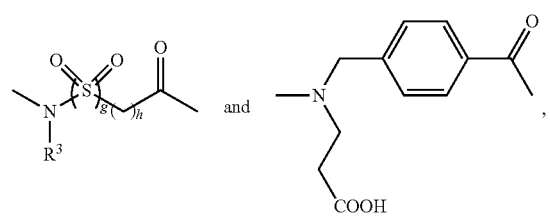

g and h are independently 0 or 1, and $R^3$ is H or —CH$_2$COOH;
E is an acidic group having a formula:

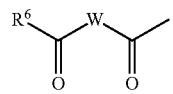

(I)

wherein W represents —(CR$^4$R$^5$)$_l$—,
$R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide,
$R^6$ is selected from hydroxyl or NR$^7$R$^8$;
$R^7$ and $R^8$ are independently selected from the group consisting of hydrogen, alkyl, hydroxyl, and

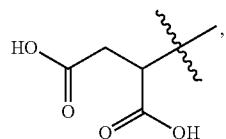

and l is an integer from 10 to 20.
In certain embodiments, the CRM is conjugated to a lysine residue, optionally the lysine residue is in the polypeptide linker or in the GLP-1 or in the FGF21.
In certain embodiments, A is a bond.
In certain embodiments, A is a bond, and B is a bond or

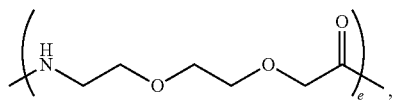

wherein e is 1, 2 or 3.
In certain embodiments, A is a bond, B is

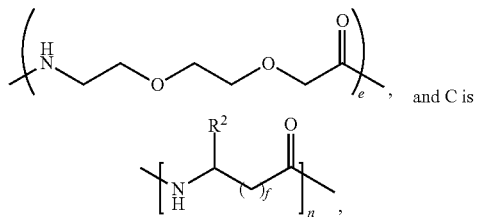

, and C is wherein e is 1, 2 or 3, f is 1, 2, or 3, and n is 1 or 2. In certain embodiments, D is a bond, and E is an acidic group having a formula:

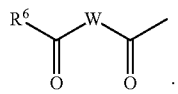

In certain embodiments, $R^2$ is —COOH, and $R^6$ is hydroxyl.
In certain embodiments, W represents —(CR$^4$R$^5$)$_l$—, $R^4$ and $R^5$ are independently hydrogen, l is an integer from 10 to 20.
In certain embodiments, A is a bond, B is a bond, and C is a bond.
In certain embodiments, A is a bond, B is a bond, and C is

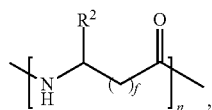

wherein f is 1, 2, or 3, and n is 1 or 2.

In certain embodiments, A is

wherein a is 1, 2 or 3, b is 1, 2 or 3, and c is 1 or 2.

In certain embodiments, A is

and B is

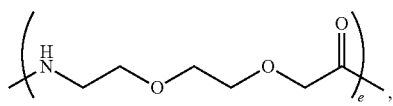

wherein a is 1, 2 or 3, b is 1, 2 or 3, c is 1 or 2, and e is 1, 2 or 3.

In certain embodiments, A is

B is

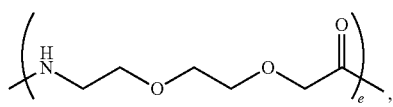

and C

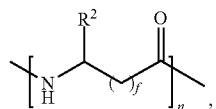

is wherein a is 1, 2 or 3, b is 1, 2 or 3, c is 1 or 2, e is 1, 2 or 3, f is 1, 2, or 3, and n is 1 or 2.

In certain embodiments, A is

B is

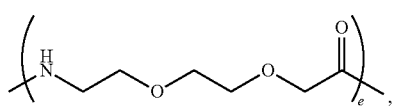

and C is bond, wherein a is 1, 2 or 3, b is 1, 2 or 3, c is 1 or 2, and e is 1, 2 or 3.

In certain embodiments, A is

and B is a bond, wherein a is 1, 2 or 3, b is 1, 2 or 3, and c is 1 or 2.

In certain embodiments, A is

B is a bond, and C is

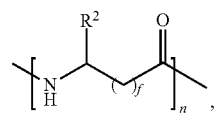

wherein a is 1, 2 or 3, b is 1, 2 or 3, c is 1 or 2, f is 1, 2, or 3, and n is 1 or 2.

In certain embodiments, A is

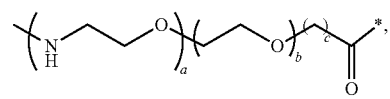

B is a bond, and C is a bond, wherein a is 1, 2 or 3, b is 1, 2 or 3, and c is 1 or 2.

In certain embodiments, D is a bond.

In certain embodiments, A is

B is

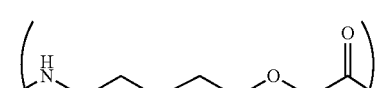

C is

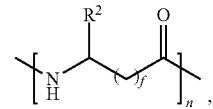

and D is a bond, wherein a is 1, 2 or 3, b is 1, 2 or 3, c is 1 or 2, e is 1, 2 or 3, f is 1, 2, or 3, and n is 1 or 2.

In certain embodiments, D is

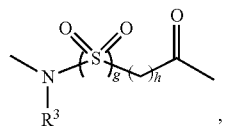

wherein g is 0 or 1, and h is 0 or 1.

In certain embodiments, A is

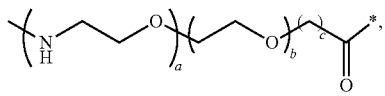

B is

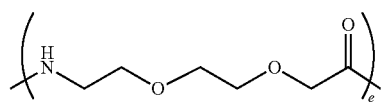

or a bond, C is a bond, and D is

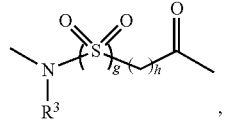

wherein a is 1, 2 or 3, b is 1, 2 or 3, c is 1 or 2, e is 1, 2 or 3, g is 0 or 1, and h is 0 or 1.

In certain embodiments, D is

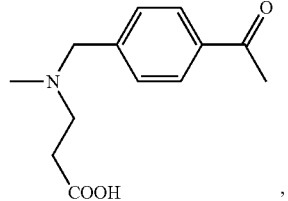 [SMILES: CC(=O)c1ccc(CN(C)CCC(=O)O)cc1]

In certain embodiments, A is

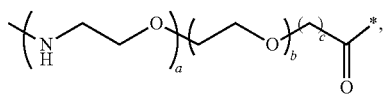

B is

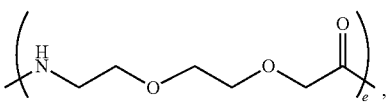

C is a bond or

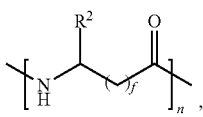

and D is

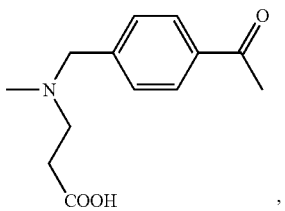

wherein a is 1, 2 or 3, b is 1, 2 or 3, c is 1 or 2, e is 1, 2 or 3, f is 1, 2, or 3, and n is 1 or 2.

In certain embodiments, the CRM comprises the structure of below formula (also referred to as —OOC—(CH2)16-CO-gGlu-2XADO, where 2XADO means two consecutive ADO moieties, and ADO is short for 8-amino-3,6-dioxaoctanoic acid):

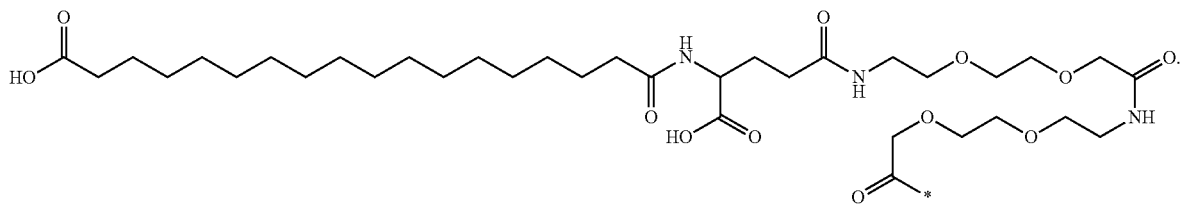 [SMILES: *C(=O)COCCOCCNC(=O)COCCOCCNC(=O)CCC(NC(=O)CCCCCCCCCCCCCCCCC(=O)O)C(=O)O]

In certain embodiments, the CRM is conjugated to at least one cysteine residue in the fusion polypeptide.

In certain embodiments, A is

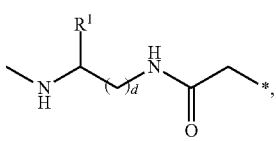

and B is

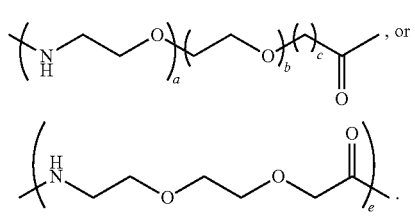

In certain embodiments, A is

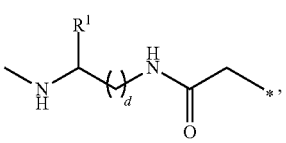

B is

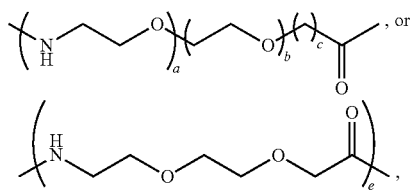

and C is

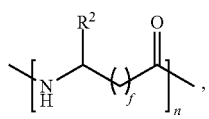

wherein a is 1, 2 or 3, b is 1, 2 or 3, c is 1 or 2, d is 1, 2, or 3, f is 1, 2, or 3, and n is 1 or 2. In certain embodiments, D is a bond, and E is an acidic group having a formula:

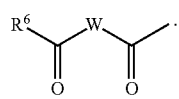

In certain embodiments, $R^2$ is —COOH, and $R^6$ is hydroxyl. In certain embodiments, W represents —$(CR^4R^5)_l$—, $R^4$ and $R^5$ are independently hydrogen, l is an integer from 10 to 20.

In certain embodiments, A is

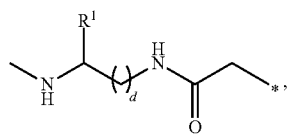

B is

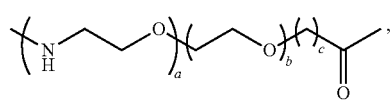

C is

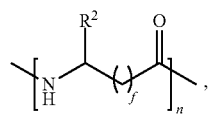

and D is a bond, wherein a is 1, 2 or 3, b is 1, 2 or 3, c is 1 or 2, d is 1, 2, or 3, f is 1, 2, or 3, and n is 1 or 2.

In certain embodiments, A is

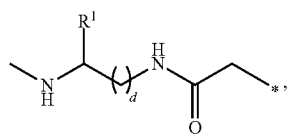

and B is

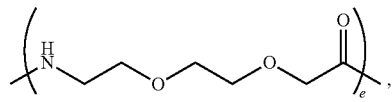

wherein d is 1, 2, or 3, and e is 1, 2 or 3.

In certain embodiments, A is

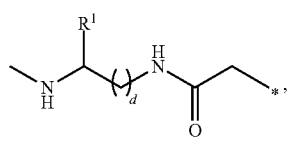

B is

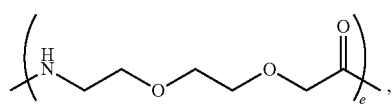

and C is a bond, wherein d is 1, 2, or 3, and e is 1, 2 or 3.

In certain embodiments, A is

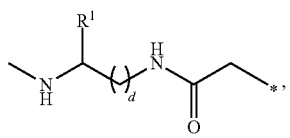

B is

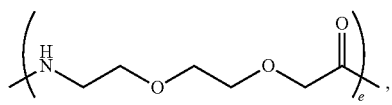

C is a bond, and D is

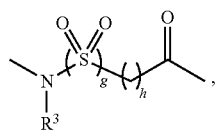

wherein d is 1, 2, or 3, e is 1, 2 or 3, g is 0 or 1, and h is 0 or 1.

In certain embodiments, the CRM comprises the structure of below formula:

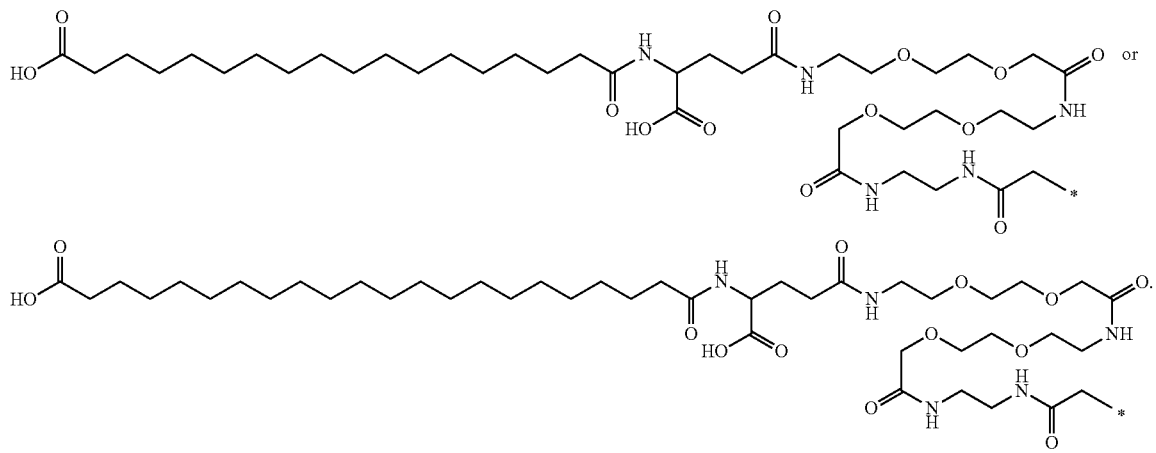

Exemplary fusion polypeptide conjugates via lysine residue are shown in Table 2A and Table 2B below

TABLE 2A

Exemplary fusion polypeptide conjugates

| Compound Code | Fusion Polypeptide SEQ ID NO: | Conjugation site | Moiety |
|---|---|---|---|
| 2 | 2 | 26K of GLP-1, 180K of FGF21 (20K, and 231K of fusion polypeptide) | Moiety A** |
| 4 | 4 | 20K of linker, 180K of FGF21 (51K, and 231K of fusion polypeptide) | Moiety A** |
| 5 | 5 | 20K of linker, 171K of FGF21 (51K, and 222K of fusion polypeptide) | Moiety A** |
| 6 | 6 | 171K of FGF21 (222K of fusion polypeptide) | Moiety A** |
| 7 | 7 | 170K of FGF21 (221K of fusion polypeptide) | Moiety A** |
| 8 | 8 | 174K of FGF21 (225K of fusion polypeptide) | Moiety A** |
| 9 | 9 | 180K of FGF21 (231K of fusion polypeptide) | Moiety A** |
| 10 | 10 | 171K of FGF21 (222K of fusion polypeptide) | Moiety A** |
| 11 | 11 | 170K of FGF21 (221K of fusion polypeptide) | Moiety A** |
| 12 | 12 | 174K of FGF21 (225K of fusion polypeptide) | Moiety A** |
| 13 | 13 | 171K of FGF21 (222K of fusion polypeptide) | Moiety A** |
| 14 | 14 | 171K of FGF21 (222K of fusion polypeptide) | Moiety A** |
| 15 | 15 | 180K of FGF21 (231K of fusion polypeptide) | Moiety A** |

TABLE 2A-continued

Exemplary fusion polypeptide conjugates

| Compound Code | Fusion Polypeptide SEQ ID NO: | Conjugation site | Moiety |
|---|---|---|---|
| 16 | 16 | 26K of GLP-1, 171K of FGF21 (20K, and 222K of fusion polypeptide) | Moiety A** |
| 17 | 17 | 26K of GLP-1, 170K of FGF21 (20K, and 221K of fusion polypeptide) | Moiety A** |
| 18 | 18 | 26K of GLP-1, 174K of FGF21 (20K, and 225K of fusion polypeptide) | Moiety A** |
| 19 | 19 | 20K of linker, 171K of FGF21 (51K, and 222K of fusion polypeptide) | Moiety A** |
| 20 | 20 | 20K of linker, 170K of FGF21 (51K, and 221K of fusion polypeptide) | Moiety A** |
| 21 | 21 | 20K of linker, 174K of FGF21 (51K, and 225K of fusion polypeptide) | Moiety A** |
| 22 | 22 | 20K of linker, 180K of FGF21 (51K, and 231K of fusion polypeptide) | Moiety A** |
| 24 | 24 | 20K of linker, 170K of FGF21 (51K, and 221K of fusion polypeptide) | Moiety A** |
| 26 | 26 | 5K of linker, 174K of FGF21 (36K, and 210K of fusion polypeptide) | Moiety A** |
| 27 | 27 | 10K of linker, 174K of FGF21 (41K, and 215K of fusion polypeptide) | Moiety A** |
| 28 | 28 | 40K of linker, 174K of FGF21 (71K, and 245K of fusion polypeptide) | Moiety A** |
| 29 | 29 | 80K of linker, 174K of FGF21 (111K, and 285K of fusion polypeptide) | Moiety A** |
| 30 | 30 | 20K of linker, 174K of FGF21 (51K, and 225K of fusion polypeptide) | Moiety A** |
| 31 | 31 | 48K of linker, 174K of FGF21 (79K, and 253K of fusion polypeptide) | Moiety A** |
| 32 | 32 | 40K of linker, 174K of FGF21 (71K, and 245K of fusion polypeptide) | Moiety A** |
| 33 | 33 | 8K of linker, 174K of FGF21 (39K, and 213K of fusion polypeptide) | Moiety A** |
| 34 | 34 | 4K of linker, 174K of FGF21 (35K, and 209K of fusion polypeptide) | Moiety A** |
| 35 | 35 | 26K of GLP-1, 170K of FGF21 (20K, and 221K of fusion polypeptide) | Moiety A** |
| 37 | 77 | 5K of linker, 171K of FGF21 (36K, and 207K of fusion polypeptide) | Moiety A** |
| 38 | 78 | 10K of linker, 171K of FGF21 (41K, and 212K of fusion polypeptide) | Moiety A** |
| 39 | 79 | 40K of linker, 171K of FGF21 (71K, and 242K of fusion polypeptide) | Moiety A** |
| 40 | 80 | 80K of linker, 171K of FGF21 (111K, and 282K of fusion polypeptide) | Moiety A** |
| 41 | 81 | 48K of linker, 171K of FGF21 (79K, and 250K of fusion polypeptide) | Moiety A** |
| 42 | 82 | 40K of linker, 171K of FGF21 (71K, and 242K of fusion polypeptide) | Moiety A** |
| 43 | 83 | 8K of linker, 171K of FGF21 (39K, and 210K of fusion polypeptide) | Moiety A** |
| 44 | 84 | 4K of linker, 171K of FGF21 (35K, and 206K of fusion polypeptide) | Moiety A** |
| 45 | 85 | 15K of linker, 171K of FGF21 (46K, and 222K of fusion polypeptide) | Moiety A** |
| 46 | 86 | 10K of linker, 171K of FGF21 (41K, and 222K of fusion polypeptide) | Moiety A** |
| 47 | 87 | 5K of linker, 171K of FGF21 (36K, and 222K of fusion polypeptide) | Moiety A** |
| 48 | 88 | 20K of linker, 171K of FGF21 (51K, and 222K of fusion polypeptide) | Moiety A** |
| 49 | 116 | 20K of linker, 181K of FGF21 (51K, and 232K of fusion polypeptide) | Moiety A** |
| 50 | 117 | 20K of linker, 182K of FGF21 (51K, and 233K of fusion polypeptide) | Moiety A** |

**Moiety A refers to HOOC—(CH2)16—CO-gGlu-2XADO or

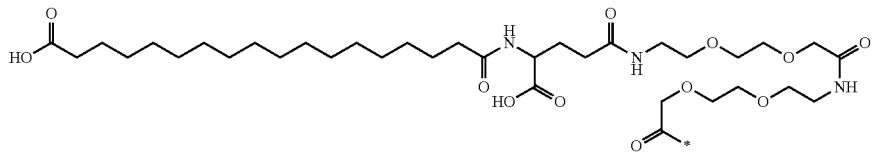 [SMILES: *C(=O)COCCOCCNC(=O)COCCOCCNC(=O)CCC(NC(=O)CCCCCCCCCCCCCCCCC(=O)O)C(=O)O]

TABLE 2B

Exemplary fusion polypeptide conjugates

| Compound Code | Fusion Polypeptide SEQ ID NO: | Conjugation site | Moiety |
|---|---|---|---|
| 51 | 148 | 20 C of linker, 171 C of FGF21 (51 C, and 222 C of fusion polypeptide) | Moiety B** |
| 52 | 149 | 20 C of linker, 174 C of FGF21 (51 C, and 225 C of fusion polypeptide) | Moiety B** |
| 53 | 150 | 20 C of linker, 182 C of FGF21 (51 C, and 233 C of fusion polypeptide) | Moiety B** |
| 54 | 151 | 20 C of linker, 180 C of FGF21 (51 C, and 231 C of fusion polypeptide) | Moiety B** |
| 55 | 152 | 20 C of linker, 171 C of FGF21 (51 C, and 222 C of fusion polypeptide) | Moiety B** |
| 56 | 153 | 20 C of linker, 174 C of FGF21 (51 C, and 225 C of fusion polypeptide) | Moiety B** |
| 57 | 154 | 20 C of linker, 180 C of FGF21 (51 C, and 231 C of fusion polypeptide) | Moiety B** |
| 58 | 155 | 24 C of linker, 174 C of FGF21 (55 C, and 229 C of fusion polypeptide) | Moiety B** |
| 59 | 156 | 28 C of linker, 174 C of FGF21 (59 C, and 233 C of fusion polypeptide) | Moiety B** |
| 60 | 157 | 20 C of linker, 174 C of FGF21 (51 C, and 225 C of fusion polypeptide) | Moiety B** |
| 61 | 158 | 15 C of linker, 174 C of FGF21 (46 C, and 225 C of fusion polypeptide) | Moiety B** |
| 62 | 159 | 10 C of linker, 174 C of FGF21 (41 C, and 225 C of fusion polypeptide) | Moiety B** |
| 63 | 160 | 20 C of linker, 171 C of FGF21 (51 C, and 222 C of fusion polypeptide) | Moiety B** |
| 64 | 161 | 15 C of linker, 171 C of FGF21 (46 C, and 222 C of fusion polypeptide) | Moiety B** |
| 65 | 162 | 10 C of linker, 171 C of FGF21 (41 C, and 222 C of fusion polypeptide) | Moiety B** |
| 66 | 163 | 20 C of linker, 174 C of FGF21 (51 C, and 225 C of fusion polypeptide) | Moiety B** |
| 67 | 164 | 15 C of linker, 174 C of FGF21 (46 C, and 235 C of fusion polypeptide) | Moiety B** |
| 68 | 165 | 20 C of linker, 171 C of FGF21 (51 C, and 222 C of fusion polypeptide) | Moiety B** |
| 69 | 166§ | 20 C of linker, 171 C of FGF21 (49 C, and 220 C of fusion polypeptide) | Moiety B** |
| 70 | 167§ | 20 C of linker, 168 C of FGF21 (51 C, and 219 C of fusion polypeptide) | Moiety B** |
| 71 | 168 | 21 C of linker, 171 C of FGF21 (52 C, and 282 C of fusion polypeptide) | Moiety B** |
| 72 | 169 | 31 C of linker, 171 C of FGF21 (62 C, and 282 C of fusion polypeptide) | Moiety B** |
| 73 | 170 | 11 C of linker, 171 C of FGF21 (42 C, and 282 C of fusion polypeptide) | Moiety B** |
| 74 | 1 | 20 C of linker, 71 C of FGF21 (51 C, and 122 C of fusion polypeptide) | Moiety B** |
| 75 | 23 | 9 C and 20 C of linker (40 C, and 51 C of fusion polypeptide) | Moiety B** |
| 76 | 25 | 20 C of linker (51 C of fusion polypeptide) | Moiety B** |
| 77 | 76 | 19 C and 40 C of linker (50 C, and 71 C of fusion polypeptide) | Moiety B** |

**Moiety B refers to HOOC—(CH2)20—CO-gGlu-2XADO-EDA-CO—CH2 or

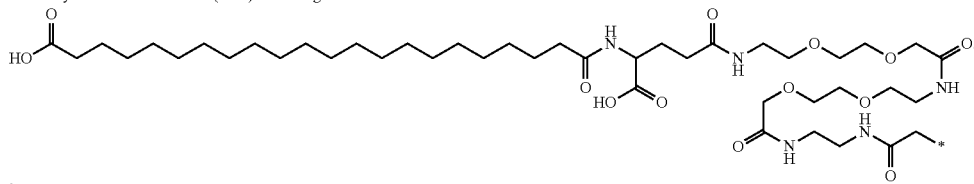

§Fusion polypeptides having an amino acid sequence of SEQ ID NOs: 166 and 167 comprising inactive GLP-1 or inactive FGF21 serves as negative control.

In certain embodiments, the conjugate provided herein comprises a fusion polypeptide comprising an amino acid sequence selected from SEQ ID NOs: 6-15, and one CRM is attached to the conjugatable lysine residue in the fusion polypeptide. Alternatively, the conjugatable lysine residue in the fusion polypeptide selected from SEQ ID NOs: 6-15 can be substituted with a cysteine or a non-natural amino acid, and the CRM is conjugated to such cysteine or non-natural amino acid.

In certain embodiments, the conjugate provided herein comprises a fusion polypeptide comprising an amino acid sequence selected from SEQ ID NOs: 25, and one CRM is attached to the conjugatable cysteine residue in the fusion polypeptide.

In certain embodiments, the conjugate provided herein comprises a fusion polypeptide comprising an amino acid sequence selected from SEQ ID NOs: 2, 4-5, 16-22, 24, 26-35, 77-88 and 116-117, two CRMs which are respectively attached to the conjugatable lysine residues in the fusion polypeptide. Alternatively, the conjugatable lysine residue in the fusion polypeptide selected from SEQ ID NOs: 2, 4-5, 16-22, 24, 26-35, 77-88 and 116-117, can be substituted with a cysteine or a non-natural amino acid, and the two CRM are conjugated to such cysteine or non-natural amino acid residues respectively.

In certain embodiments, the conjugate provided herein comprises a fusion polypeptide comprising an amino acid sequence selected from SEQ ID NOs: 2, 4-5, 16-22, 24, 26-35, 77-88 and 116-117, and two CRMs each of which attached to one of the conjugatable lysine residues in the fusion polypeptide. In certain embodiments, the first CRMs is conjugated to the conjugatable lysine residue in the FGF21, and the second CRM is conjugated to the conjugatable lysine residue in the GLP-1 or the polypeptide linker.

4) N is 9, m is 231, mK is 231K (such a conjugate molecule is also referred to as Compound 9), 5) N is 10, m is 222, mK is 222K (such a conjugate molecule is also referred to as Compound 10), 6) N is 11, m is 221, mK is 221K (such a conjugate molecule is also referred to as Compound 11), 7) N is 12, m is 225, mK is 225K (such a conjugate molecule is also referred to as Compound 12), 8) N is 13, m is 222, mK is 222K (such a conjugate molecule is also referred to as Compound 13), 9) N is 14, m is 222, mK is 222K (such a conjugate molecule is also referred to as Compound 14), or 10) N is 15, m is 231, mK is 231K (such a conjugate molecule is also referred to as Compound 15), and wherein the CRM has the structure of below formula:

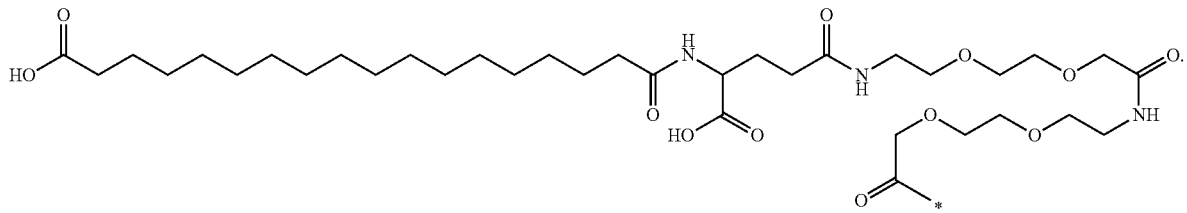 [SMILES: CC(=O)COCCOCCNC(=O)COCCOCCNC(=O)CCC(NC(=O)CCCCCCCCCCCCCCCCC(=O)O)C(=O)O]

In certain embodiments, the conjugate provided herein comprises a fusion polypeptide comprising an amino acid sequence selected from SEQ ID NOs: 148-165, 168-170, 1, 23 and 76, two CRMs which are respectively attached to the conjugatable cysteine residues in the fusion polypeptide. In certain embodiments, the first CRMs is conjugated to the conjugatable cysteine residue in the FGF21, and the second CRM is conjugated to the conjugatable cysteine residue in the polypeptide linker. In certain embodiments, the first and the second CRM are both conjugated to the conjugatable cysteine residues in the polypeptide linker.

In certain embodiments, the present disclosure provides a polypeptide conjugate comprising a fusion polypeptide conjugated to a CRM, or a pharmaceutically acceptable salt thereof, wherein the fusion polypeptide comprising an amino acid sequence of SEQ ID NO: N, and the CRM which is covalently attached to the $m^{th}$ residue (which is Cysteine, i.e. mC) counting in a direction from N terminus to C terminus in the fusion polypeptide, and wherein: 1) N is 25, m is 51, mC is 51C (such a conjugate molecule is also referred to as Compound 76), wherein the CRM has the structure of below formula:

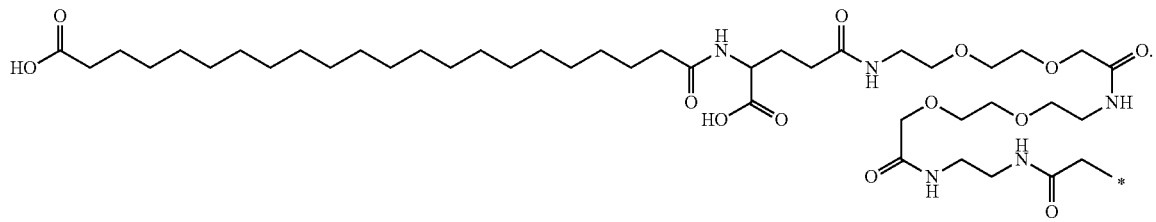 [SMILES: CCC(=O)NCCNC(=O)COCCOCCNC(=O)COCCOCCNC(=O)CCC(NC(=O)CCCCCCCCCCCCCCCCCCCCC(=O)O)C(=O)O]

In certain embodiments, the present disclosure provides a polypeptide conjugate comprising a fusion polypeptide conjugated to a CRM, or a pharmaceutically acceptable salt thereof, wherein the fusion polypeptide comprising an amino acid sequence of SEQ ID NO: N, and the CRM which is covalently attached to the $m^{th}$ residue (which is lysine, i.e. mK) counting in a direction from N terminus to C terminus in the fusion polypeptide, wherein:

1) N is 6, m is 222, mK is 222K (such a conjugate molecule is also referred to as Compound 6), 2) N is 7, m is 221, mK is 221K (such a conjugate molecule is also referred to as Compound 7), 3) N is 8, m is 225, mK is 225K (such a conjugate molecule is also referred to as Compound 8), or a pharmaceutically acceptable salt thereof.

In certain embodiments, the present disclosure provides a polypeptide conjugate comprising a fusion polypeptide conjugated to a first CRM and a second CRM, or a pharmaceutically acceptable salt thereof, wherein the fusion polypeptide comprising an amino acid sequence of SEQ ID NO: X, and the first and the second CRMs that are covalently attached respectively to the $p^{th}$ and the $q^{th}$ residues (both of which are lysine, i.e. pK or qK) counting in a direction from N terminus to C terminus in the fusion polypeptide, with one CRM attached to one residue, wherein:

1) X is 2, p is 20, pK is 20K, q is 231, qK is 231K (such a conjugate molecule is also referred to as Compound 2), 2) X is 4, p is 51, pK is 51K, q is 231, qK is 231K (such a conjugate molecule is also referred to as Compound 4),
3) X is 5, p is 51, pK is 51K, q is 222, qK is 222K (such a conjugate molecule is also referred to as Compound 5),
4) X is 16, p is 20, pK is 20K, q is 222, qK is 222K (such a conjugate molecule is also referred to as Compound 16),
5) X is 17, p is 20, pK is 20K, q is 221, qK is 221K (such a conjugate molecule is also referred to as Compound 17),
6) X is 18, p is 20, pK is 20K, q is 225, qK is 225K (such a conjugate molecule is also referred to as Compound 18),
7) X is 19, p is 51, pK is 51K, q is 222, qK is 222K (such a conjugate molecule is also referred to as Compound 19),
8) X is 20, p is 51, pK is 51K, q is 221, qK is 221K (such a conjugate molecule is also referred to as Compound 20),
9) X is 21, p is 51, pK is 51K, q is 225, qK is 225K (such a conjugate molecule is also referred to as Compound 21),
10) X is 22, p is 51, pK is 51K, q is 231, qK is 231K (such a conjugate molecule is also referred to as Compound 22),
11) X is 24, p is 51, pK is 51K, q is 221, qK is 221K (such a conjugate molecule is also referred to as Compound 24),
12) X is 26, p is 36, pK is 36K, q is 210, qK is 210K (such a conjugate molecule is also referred to as Compound 26),
13) X is 27, p is 41, pK is 41K, q is 215, qK is 215K (such a conjugate molecule is also referred to as Compound 27),
14) X is 28, p is 71, pK is 71K, q is 245, qK is 245K (such a conjugate molecule is also referred to as Compound 28),
15) X is 29, p is 111, pK is 111K, q is 285, qK is 285K (such a conjugate molecule is also referred to as Compound 29),
16) X is 30, p is 51, pK is 51K, q is 225, qK is 225K (such a conjugate molecule is also referred to as Compound 30),
17) X is 31, p is 79, pK is 79K, q is 253, qK is 253K (such a conjugate molecule is also referred to as Compound 31),
18) X is 32, p is 71, pK is 71K, q is 245, qK is 245K (such a conjugate molecule is also referred to as Compound 32),
19) X is 33, p is 39, pK is 39K, q is 213, qK is 213K (such a conjugate molecule is also referred to as Compound 33),
20) X is 34, p is 35, pK is 35K, q is 209, qK is 209K (such a conjugate molecule is also referred to as Compound 34),
21) X is 35, p is 20, pK is 20K, q is 221, qK is 221K (such a conjugate molecule is also referred to as Compound 35),
22) X is 77, p is 36, pK is 36K, q is 207, qK is 207K (such a conjugate molecule is also referred to as Compound 37),
23) X is 78, p is 41, pK is 41K, q is 212, qK is 212K (such a conjugate molecule is also referred to as Compound 38),
24) X is 79, p is 71, pK is 71K, q is 242, qK is 242K (such a conjugate molecule is also referred to as Compound 39),
25) X is 80, p is 111, pK is 111K, q is 282, qK is 282K (such a conjugate molecule is also referred to as Compound 40),
26) X is 81, p is 79, pK is 79K, q is 250, qK is 250K (such a conjugate molecule is also referred to as Compound 41),
27) X is 82, p is 71, pK is 71K, q is 242, qK is 242K (such a conjugate molecule is also referred to as Compound 42),
28) X is 83, p is 39, pK is 39K, q is 210, qK is 210K (such a conjugate molecule is also referred to as Compound 43),
29) X is 84, p is 35, pK is 35K, q is 206, qK is 206K (such a conjugate molecule is also referred to as Compound 44),
30) X is 85, p is 46, pK is 46K, q is 222, qK is 222K (such a conjugate molecule is also referred to as Compound 45,
31) X is 86, p is 41, pK is 41K, q is 222, qK is 222K (such a conjugate molecule is also referred to as Compound 46),
32) X is 87, p is 36, pK is 36K, q is 222, qK is 222K (such a conjugate molecule is also referred to as Compound 47),
33) X is 88, p is 51, pK is 51K, q is 222, qK is 222K (such a conjugate molecule is also referred to as Compound 48),
34) X is 116, p is 51, pK is 51K, q is 232, qK is 232K (such a conjugate molecule is also referred to as Compound 49), or
35) X is 117, p is 51, pK is 51K, q is 233, qK is 233K (such a conjugate molecule is also referred to as Compound 50), and
wherein the CRM has the structure of below formula:

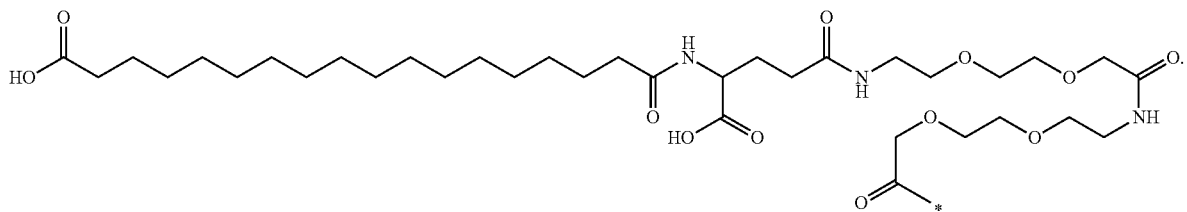 [SMILES: CC(=O)COCCOCCNC(=O)COCCOCCNC(=O)CCC(NC(=O)CCCCCCCCCCCCCCCCC(=O)O)C(=O)O]

In certain embodiments, the present disclosure provides a polypeptide conjugate comprising a fusion polypeptide conjugated to a first CRM and a second CRM, or a pharmaceutically acceptable salt thereof,
wherein the fusion polypeptide comprising an amino acid sequence of SEQ ID NO: X, and the first and the second CRMs that are covalently attached respectively to the $p^{th}$ and the $q^{th}$ residues (both of which are cysteine, i.e. pC or qC) counting in a direction from N terminus to C terminus in the fusion polypeptide, with one CRM attached to one residue, wherein:

1) X is 148, p is 51, pC is 51C, q is 222, qC is 222C (such a conjugate molecule is also referred to as Compound 51),
2) X is 149, p is 51, pC is 51C, q is 225, qC is 225C (such a conjugate molecule is also referred to as Compound 52),
3) X is 150, p is 51, pC is 51C, q is 233, qC is 233C (such a conjugate molecule is also referred to as Compound 53),
4) X is 151, p is 51, pC is 51C, q is 231, qC is 231C (such a conjugate molecule is also referred to as Compound 54),
5) X is 152, p is 51, pC is 51C, q is 222, qC is 222C (such a conjugate molecule is also referred to as Compound 55),
6) X is 153, p is 51, pC is 51C, q is 225, qC is 225C (such a conjugate molecule is also referred to as Compound 56),
7) X is 154, p is 51, pC is 51C, q is 231, qC is 231C (such a conjugate molecule is also referred to as Compound 57),
8) X is 155, p is 55, pC is 55C, q is 229, qC is 229C (such a conjugate molecule is also referred to as Compound 58),
9) X is 156, p is 59, pC is 59C, q is 233, qC is 233C (such a conjugate molecule is also referred to as Compound 59),
10) X is 157, p is 51, pC is 51C, q is 225, qC is 225C (such a conjugate molecule is also referred to as Compound 60),
11) X is 158, p is 46, pC is 46C, q is 225, qC is 225C (such a conjugate molecule is also referred to as Compound 61),
12) X is 159, p is 41, pC is 41C, q is 225, qC is 225C (such a conjugate molecule is also referred to as Compound 62),
13) X is 160, p is 51, pC is 51C, q is 222, qC is 222C (such a conjugate molecule is also referred to as Compound 63),
14) X is 161, p is 46, pC is 46C, q is 222, qC is 222C (such a conjugate molecule is also referred to as Compound 64),
15) X is 162, p is 41, pC is 41C, q is 222, qC is 222C (such a conjugate molecule is also referred to as Compound 65),
16) X is 163, p is 51, pC is 51C, q is 225, qC is 225C (such a conjugate molecule is also referred to as Compound 66),
17) X is 164, p is 46, pC is 46C, q is 235, qC is 235C (such a conjugate molecule is also referred to as Compound 67),
18) X is 165, p is 51, pC is 51C, q is 222, qC is 222C (such a conjugate molecule is also referred to as Compound 68),
19) X is 168, p is 52, pC is 52C, q is 282, qC is 282C (such a conjugate molecule is also referred to as Compound 71),
20) X is 169, p is 62, pC is 62C, q is 282, qC is 282C (such a conjugate molecule is also referred to as Compound 72),
21) X is 170, p is 42, pC is 42C, q is 282, qC is 282C (such a conjugate molecule is also referred to as Compound 73),
22) X is 1, p is 51, pC is 51C, q is 122, qC is 122C (such a conjugate molecule is also referred to as Compound 74),
23) X is 23, p is 40, pC is 40C, q is 51, qC is 51C (such a conjugate molecule is also referred to as Compound 75), or
24) X is 76, p is 50, pC is 50C, q is 71, qC is 71C (such a conjugate molecule is also referred to as Compound 77), and wherein the CRM has the structure of below formula:

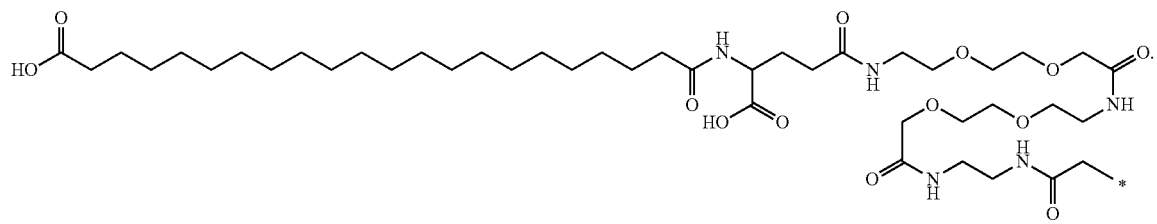 [SMILES: CCC(=O)NCCNC(=O)COCCOCCNC(=O)COCCOCCNC(=O)CCC(NC(=O)CCCCCCCCCCCCCCCCCCCCC(=O)O)C(=O)O]

or a pharmaceutically acceptable salt thereof.

In another aspect, the present disclosure provides a method of producing the conjugate provided herein, comprising conjugating a clearance-reducing moiety to the fusion polypeptide provided herein.

CRMs may be linked to the fusion polypeptide or the polypeptide complex by covalent binding, affinity binding, intercalation, coordinate binding, complexation, association, blending, or addition, among other methods.

In certain embodiments, the fusion polypeptide may be linked to a CRM directly, or indirectly for example through another moiety or through a coupling agent.

The fusion polypeptide can be conjugated at, for example, the lysine residue, the cysteine residue, or the non-natural amino acid by a suitable conjugation reaction.

For example, the fusion polypeptide having a conjugatable residue such as lysine may be reacted with an amino-reactive agent. In certain embodiments, the CRM is conjugated to the conjugatable lysine residue via an acyl group in an acylation reaction. Exemplary methods of acylation reaction is described in, for example, WO2009083549 and WO2010029159, the content of which is incorporated herein to its entirety. The CRM to be conjugated in an acylation reaction may contain a carboxylic acid group, an $\alpha,\omega$-fatty diacid residue, an activated ester, or an activated N-hydroxy imide ester, among others. Examples of activated esters include, 0-succinimide reagents like N-hydroxysuccinimidyl (NHS) or sulfo-NHS esters and imido ester compounds like Traut's reagent, which can react with the $\epsilon$-amino group of a conjugatable lysine residue to form amide or amidine bonds. Additional examples of suitable amino-reactive agent include, O-acylisourea, N-hydroxy trialzole esters, anhydride, phenyl active esters, P-hydroxamic active esters, acylimidazoles, acylbenzotriazoles, acyl azides, acid hylides, phophonium salts, aminium/uronium salts.

For another example, the fusion polypeptide having a conjugatable residue such as cysteine may be linked to a thiol-reactive agent. In certain embodiments, the CRM is conjugated to the conjugatable cysteine residue via a maleimide or an iodoacetamide to form a carbon-sulfur bond. In certain embodiments, the CRM is conjugated to the conjugatable cysteine residue via a disulphide to form a disulfide bond. Additional examples of suitable thiol-reactive group include include, dienyl sulfone, $\alpha$-haloacyl, or other thiol-reactive conjugation partner. See, for details, Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671.

For example, the fusion polypeptide having a conjugatable residue such as NNAA can be conjugated to a CRM such that a stable linkage can be formed between the NNAA of the fusion polypeptide and the CRM. For example, NNAAs containing keto group or aldehyde or β-diketomoieties can react with a hydrazide- or O-alkylhydroxylamine-, hydroxylamine-containing agents to form a hydrazone or an O-alkylated oxime linkage. For another example, NNAAs containing an azide group can react with an alkyne derivative to form a stable triazole linker by copper (I) catalyzed [3+2] cycloaddition (and vice versa). For another example, NNAAs containing an azide group can be ligated with an appropriate water soluble phosphine-containing agent to form an amide linkage by a Staudinger ligation. Further, a thioester moiety in an NNAA can react with an amine-containing agent to form amide linkage. The fusion polypeptides provided herein incorporated with an NNAA can be conjugated with an agent via cycloaddition reactions, such as (4+2) cycloaddtion between diene and dienophile (Diels-Alder reaction), (3+2) cycloaddtion via 1, 3-dipolar Huisgen cycloaddition, and (3+2) cycloaddtion via Nitrone-olefin cycloaddition. Cycloaddition methods suitable for antibody conjugation have been described in, for example, WO05003294, US20120004183, WO06009901, WO07130453 and U.S. Pat. No. 6,737,236.

For another example, the fusion polypeptide may be conjugated to biotin, then indirectly conjugated to CRM that is conjugated to avidin. For still another example, the fusion polypeptide may be linked to a coupling agent which further links to the CRM. Examples of the coupling agents include bifunctional moieties such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suherate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulphide linkage.

Additional methods for the conjugation of CRM to fusion polypeptides are found, for example, in U.S. Pat. Nos. 5,208,020; 64,411,163; WO2005037992; WO2005081711; and WO2006/034488, which are incorporated herein by reference to the entirety. Specific examples of methods of preparing the conjugates of the present disclosure are also included in the experimental part of the present disclosure.

The fusion polypeptide, and conjugates thereof provided herein have combined benefits of two mechanisms of action and have a synergistic effects with anti-diabetes/NASH and additional benefits. The fusion polypeptide and the conjugates thereof provided herein provided better efficacy than Semaglutide and FGF21 individually with much less systematic exposure, indicating a potentially better safety profile and potentially improved therapeutic index.

Pharmaceutical Composition

In another aspect, the present disclosure also provides a pharmaceutical composition comprising the fusion polypeptide conjugate provided herein and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the fusion polypeptide, the polypeptide complex or the conjugate disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the fusion polypeptide, the polypeptide complex or the conjugate as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the fusion polypeptide, the polypeptide complex, or the conjugate provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Administration of the pharmaceutical composition as described herein may be via any route known to be effective by the physician of ordinary skill. One example is peripheral parenteral administration by a sterile syringe or some other mechanical device such as an infusion pump. In certain embodiments, peripheral parenteral route is intravenous, intramuscular, subcutaneous, or intraperitoneal routes of administration.

In certain embodiments, the fusion polypeptide, the polypeptide complex, or the conjugate described herein is formulated in a form suitable for non-parenteral routes administration, such as oral, rectal, nasal, or lower respiratory routes administration.

In certain embodiments, the fusion polypeptide, the polypeptide complex, or the conjugate described herein is formulated in a solid formulation such as lyophilization or spray drying, which is then reconstituted in a suitable diluent solution prior to administration. Standard pharmaceutical formulation techniques, such as those described in Remington: The Science and Practice of Pharmacy (D. B. Troy, Editor, 21st Edition, Lippincott, Williams & Wilkins, 2006), may be employed. Alternatively, the fusion polypeptide, the polypeptide complex, or the conjugate described herein can be formulated for administration through the lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, transdermal, or pulmonary route. As a still further option, the fusion polypeptide, the polypeptide complex, or the conjugate described herein can be formulated for administration through transdermal administration, for example, by needle-free injection or from a patch, optionally an iontophoretic patch, or transmucosal, for example, buccal, administration.

Method of Treatment

In another aspect, the present disclosure provides a method of preventing or treating a metabolic disorder in a subject in need thereof, comprising administering a therapeutically effective amount of the polypeptide conjugate or the pharmaceutical composition provided herein.

Therapeutic methods are also provided, comprising: administering a therapeutically effective amount of the polypeptide conjugate or the pharmaceutical composition provided herein to a subject in need thereof, thereby treating or preventing a condition or a disorder. In certain embodiments, the subject has been identified as having a disorder or condition likely to respond to the polypeptide conjugate or the pharmaceutical composition provided herein.

In certain embodiments, the metabolic disorder is diabetes, obesity, non-alcoholic steatohepatitis (NASH), cardiovascular like dyslipidaemia, artheroscelerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

For example, a metabolic condition or disorder that can be treated or ameliorated using the polypeptide conjugate or the pharmaceutical composition provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL.

The therapeutically effective amount of the polypeptide conjugate or the pharmaceutical composition provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the polypeptide conjugate or the pharmaceutical composition provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the polypeptide conjugate or the pharmaceutical composition provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the polypeptide conjugate or the pharmaceutical composition provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The polypeptide conjugate or the pharmaceutical composition provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

The polypeptide conjugate or the pharmaceutical composition may be administered alone or in combination with one or more additional therapeutic means or agents.

In certain embodiments, when used for treating a metabolic disease, the polypeptide conjugate or the pharmaceutical composition provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art.

Method of Preparation

The present disclosure provides isolated nucleic acids or polynucleotides that encode the fusion polypeptide as described herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the fusion polypeptide described herein can be constructed using recombinant techniques. To this end, DNA encoding the GLP-1 polypeptide and DNA encoding the FGF21 polypeptide can be obtained and operably linked to allow transcription and expression in a host cell to produce the fusion polypeptide. Polynucleotide sequences encoding for the polypeptide linkers are also operably linked to allow expression of the desired product.

The encoding polynucleotide sequences can be further operably linked to one or more regulatory sequences, optionally in an expression vector, such that the expression or production of the fusion polypeptides is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, lpp, npr, pac, syn, trc and T3, or eukaryotic promoters such as SV40, CMV, and EF-1a), and a transcription termination sequence.

Vectors and Host Cells

In another aspect, the present disclosure provides a vector comprising the polynucleotide of provided herein.

Vectors comprising the polynucleotide sequence(s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell or eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the fusion polypeptide can be subcloned into an expression vector, which is expressed as inclusion bodies in the host cells. The vector can be a viral vector, and any suitable viral vector can be used in this capacity.

In another aspect, the present disclosure provides a host cell comprising the vector provided herein. The host cell is prokaryotic cell or a eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the fusion polypeptide as described herein, comprising culturing the host cell provided herein under a condition that allows expression of the fusion polypeptide as described herein.

For production of the fusion polypeptide as described herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the fusion polypeptide as described herein, comprising culturing the host cell provided herein under the condition at which the fusion polypeptide as described herein is expressed.

In certain embodiments, the fusion polypeptide is expressed as inclusion bodies. In certain embodiments, the method further comprises renaturing the fusion polypeptide from the inclusion bodies.

When using recombinant techniques, the fusion polypeptide as described herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the fusion polypeptide.

The fusion polypeptide as described herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

Kit

Also provided are kits for practicing the disclosed methods. Such kits can comprise a pharmaceutical composition such as those described herein, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a fusion polypeptide conjugate; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular like dyslipidaemia, artherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

EXAMPLES

Example 1: Recombinant Expression of Fusion Proteins

The GLP-1/FGF21 fusion proteins listed in Table 1 were produced from bacterial *E. coli* expression system, using BL21(DE3) derivative strain. The DNA coding for the GLP-1/FGF21 fusion precursors was codon optimized for *E. coli* expression, de novo synthesized and subcloned into PET derivative expression vectors (Novagen). Amino acid substitutions were accomplished by modification of the corresponding genetic codes. Overexpression of GLP-1/FGF21 precursor as inclusion bodies was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours. The quality of inclusion bodies was analyzed with microscopic imaging.

Example 2: Refolding and Purification

Cells were harvested and lysed by cell disruptor (900 bar, for twice). The insoluble fraction, containing the fusion protein, were collected and washed twice by centrifugation (8,000×g, for 30 min). The 6M urea with 10 mM DTT buffer was then used to solubilize the inclusion bodies. After 0.5 hours, the solution was diluted with refolding buffer and stirred at the room temperature for 12 hours. After removing tag by protease, the protein was loaded on to anion exchange chromatography using Q Sepharose Fast flow resin (GE healthcare) and further polishing was performed by anion exchange chromatography using SuperQ-5PW resin (TOSOH). The samples in each step were characterized by LC/MS to confirm the correct molecular weight.

Example 3: Preparation of Fusion Protein Conjugates

To a solution of GLP1/FGF21 fusion protein (75 mg) in NaOH or Tris buffer was added with CRM reagent (i.e. HOOC—(CH2)16-CO-gGlu-2XADO, HOOC—(CH2)16-CO-gGlu-2XADO-EDA-CO—CH2, or HOOC—(CH2)20-CO-gGlu-2XADO-EDA-CO—CH2) (6 mg or 12 mg) in organic solvent dropwise. The reaction was stirred at room temperature for 1 h. Then the product was applied to anion exchange chromatography using Source 30Q resin (GE healthcare).

The conjugated fusion proteins (as shown in Table 2) were detected and characterized by LC-MS method with Waters BioAccord LC-MS system, or by UPLC with Waters Acquity UPLC system, using conditions optimized for different conjugates, following the supplier's manuals.

Example 4: In Vitro Activities of Exemplary Fusion Protein Conjugates

Method:

The in vitro GLP-1 activities of some exemplary fusion protein conjugates were measured using a BHK cell line overexpressing human GLP-1 receptor and CRE luciferase reporter. Tested fusion protein conjugates were measured at 1 nM top concentration with 3-fold serial dilutions. After cells were treated with fusion protein conjugates for 4 hours, luciferase activities were measured by Steadylite plus kit (Perkin Elmer, 6066751). Semaglutide was tested in parallel conditions as a control. Semaglutide was purchased from Novo Nordisk, lot JP51144. According to the product label, Semaglutide is a human GLP-1 analog conjugated with HOOC—(CH2)16-CO-gGlu-2XADO at the 26th residue (lysine).

The in vitro FGF21 activities of the exemplary fusion protein conjugates were assessed using a HEK293 cell line overexpressing human beta-Klotho. Tested fusion protein conjugates were measured at 200 nM top concentration with 3-fold serial dilutions. After cells were treated with fusion protein conjugates for 5 mins, p-ERK levels were measured by p-ERK kit (Cisbio, 64ERKPEH).

The activity of each exemplary fusion protein conjugate was represented by $EC_{50}$, derived from non-linear regression analysis.

Conclusion:

Exemplary fusion protein conjugates showed 3-9 fold less potent GLP-1 activities than Semaglutide, and similar or same magnitude of FGF21 activities compared to native FGF21 (Table 3).

TABLE 3

In vitro activities of exemplary fusion protein conjugates.

| Compound Code | GLP-1 activity ($EC_{50}$, pM) | FGF21 activity ($EC_{50}$, nM) |
|---|---|---|
| Semaglutide | 5.4 | n/a |
| Native FGF21 | n/a | 10.6 |
| 2 | 46.6 | 5.5 |
| 4 | 25.1 | 7.7 |
| 5 | 23.1 | 12.9 |
| 9 | 19.9 | 4.9 |
| 10 | 17.6 | 4.5 |
| 11 | 18.2 | 3.9 |
| 12 | 17.0 | 4.1 |
| 13 | 19.6 | 9.1 |
| 14 | 33.2 | 19.0 |
| 15 | 16.8 | 7.3 |
| 19 | 20.3 | 13.6 |
| 20 | 39.1 | 10.6 |
| 21 | 36.8 | 17.6 |
| 22 | 50.4 | 7.0 |
| 39 | 12.6 | 4.2 |
| 40 | 7.2 | 8 |
| 42 | 10 | 8.4 |
| 48 | 14.4 | 20.4 |
| 50 | 15.4 | 8.7 |
| 51 | 30.7 | 4.3 |
| 52 | 30.2 | 2.4 |
| 54 | 19 | 3.4 |
| 63 | 49.1 | 1.2 |
| 66 | 41.3 | 1.0 |
| 69 | >1000 | 0.53 |
| 70 | 24.8 | >100 |
| 71 | 16.5 | 2.7 |
| 72 | 16.5 | 2.4 |
| 73 | 16.6 | 3.6 |

Example 5: In Vivo Activities of Exemplary Fusion Protein Conjugates

Method:

10 week old male C57BL/6 mice were injected everyday subcutaneously with 30 nmol/kg exemplary fusion protein conjugates for 10 or 14 days (n=5). Body weight was daily monitored for each individual animal. Day 1 and Day 10 (or Day 14) are first day and last day of molecule dosage. % BW loss=100*(BW on Day n-BW on Day 1)/(BW on Day 1). Data are indicated as mean values and standard error (SEM) or pooled values. Statistical analysis was performed by One-way ANOVA. Body weight reduction on Day 11 in Table 5 is calculated by −1*(% BW loss−% BW loss of vehicle group).

TABLE 5

Body weight reduction in C57BL/6 mice at Day11

| Compound Code | Body weight reduction at 30 nmol/kg (% reduction compared to vehicle)(Day11) |
|---|---|
| Semaglutide | 6.4 |
| 4 | 27.0 |
| 5 | 14.4 |
| 10 | 20.0 |
| 2 | 18.2 |
| 9 | 27.2 |
| 11 | 10.4 |
| 12 | 22.8 |
| 13 | 23.6 |
| 14 | 9.8 |
| 15 | 11.3 |
| 19 | 27.0 |
| 20 | 26.6 |
| 21 | 34.4 |
| 22 | 32.9 |
| 50 | 9.4 |
| 39 | 32.5 |
| 40 | 33.1 |
| 42 | 33.6 |
| 48 | 27.8 |
| 51 | 26.2 |
| 52 | 20.9 |
| 54 | 13.5 |
| 63 | 24.5 |
| 66 | 18.9 |
| 71 | 24.5 |
| 72 | 25.8 |
| 73 | 20.2 |

Figure 1B:
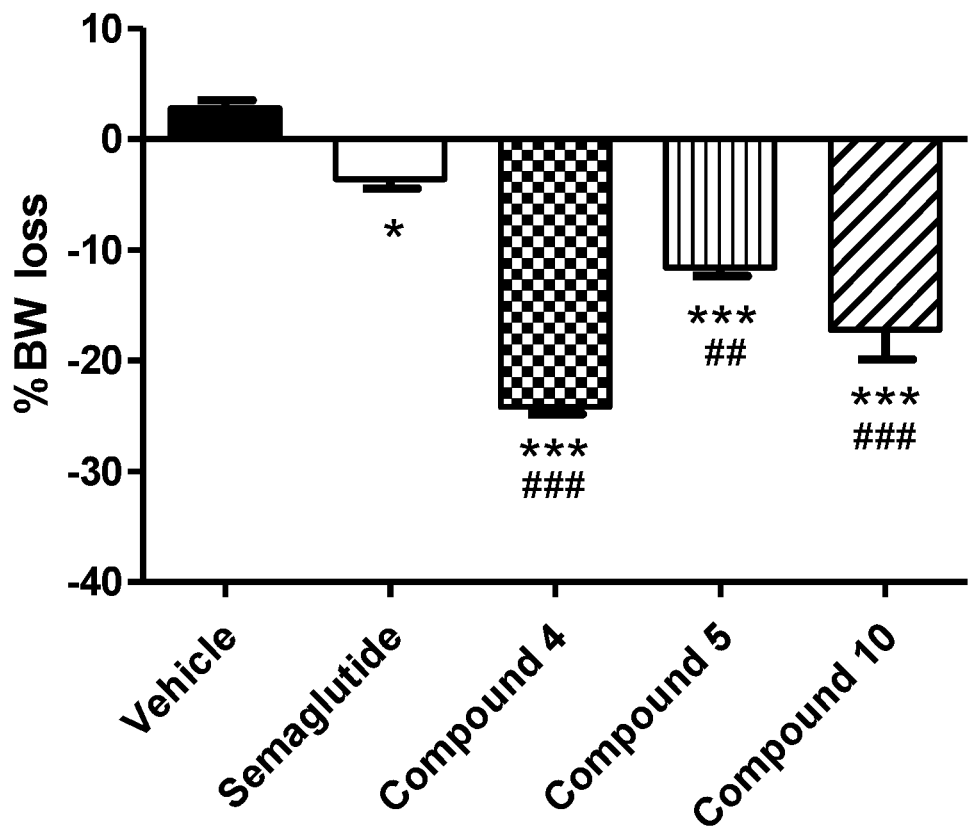
Figure 1C:
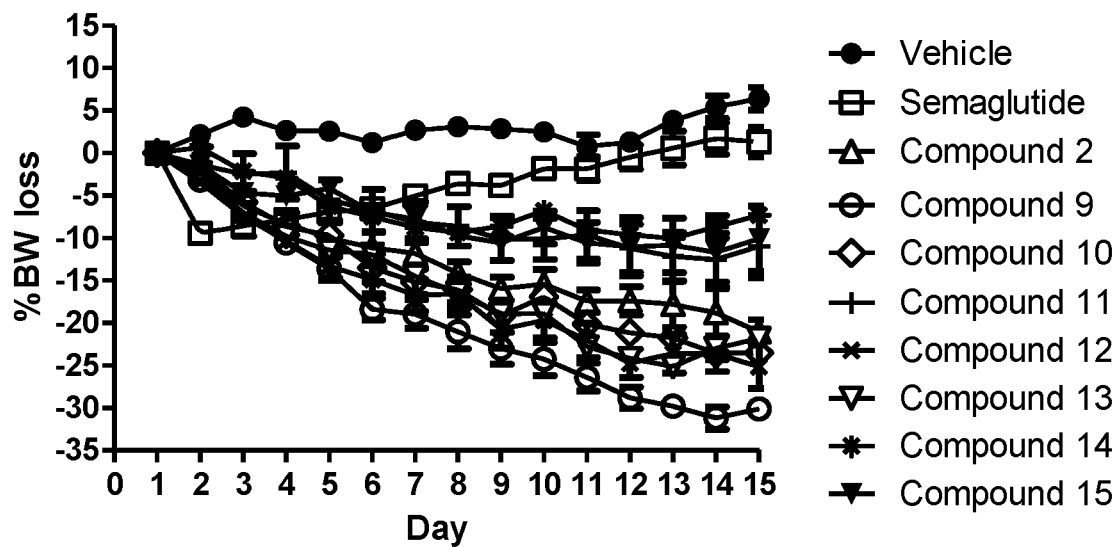
Figure 1D:
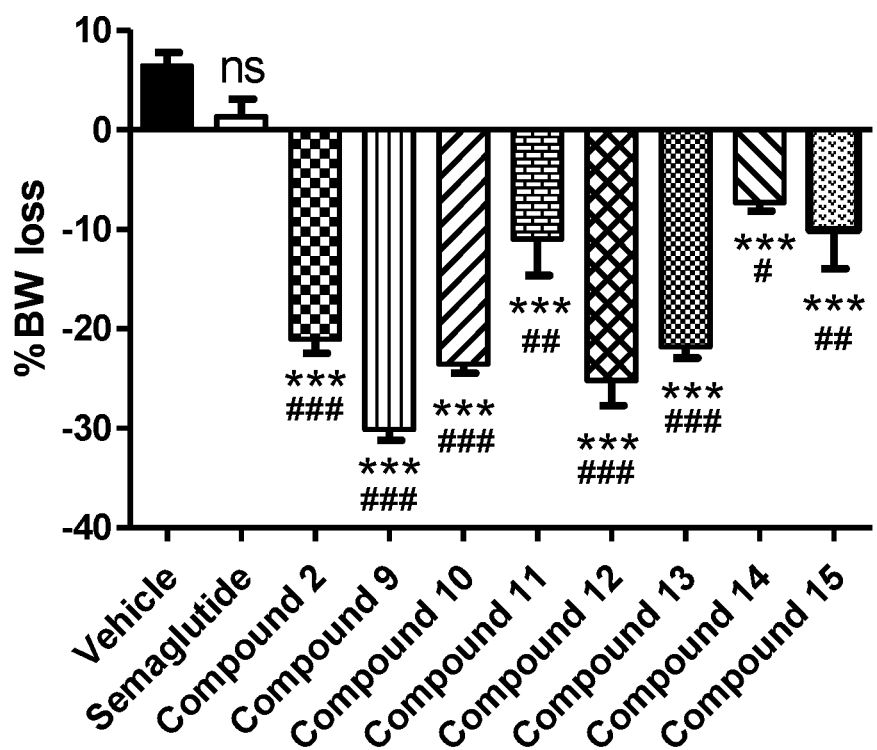
Figure 1E:
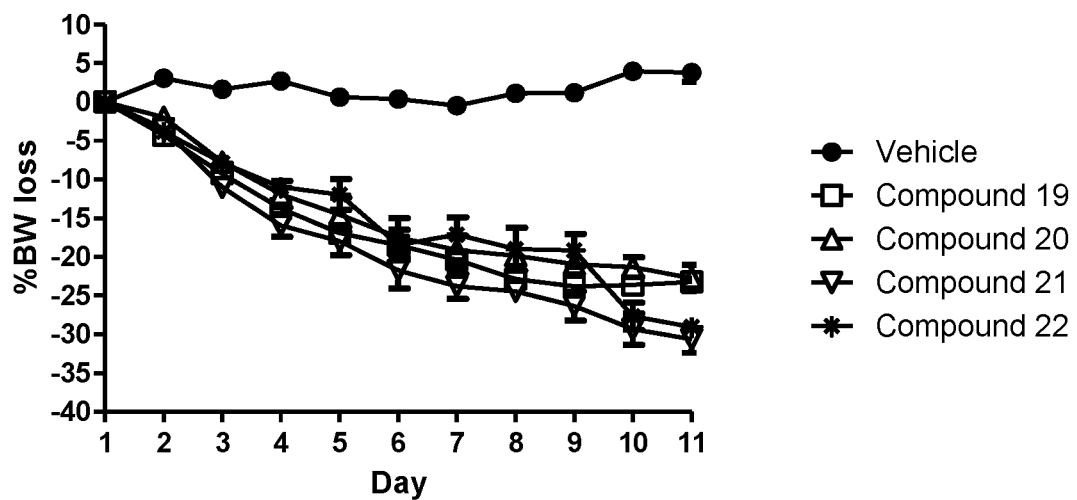
Figure 1F:
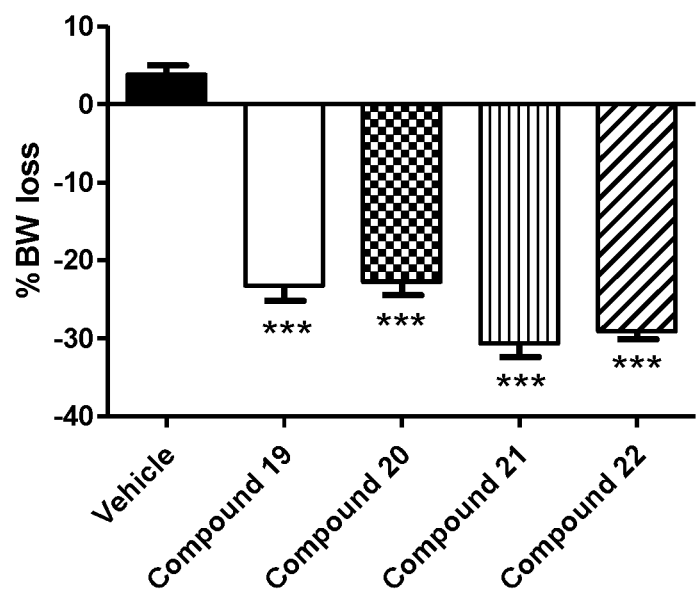

Conclusion:

All tested exemplary fusion protein conjugates (Compounds 4, 5 and 10) exhibited much more enhanced and persistent BW reduction compared to Semaglutide during the 10-day dosing period (FIGS. 1A-1B). All tested exemplary fusion protein conjugates (Compounds 2 and 9-15), exhibited much more enhanced and persistent BW reduction compared to Semaglutide during the 14-day dosing period (FIGS. 1C-1D). All tested exemplary fusion protein conjugates (Compounds 19-22), exhibited persistent BW reduction compared to Vehicle Control (FIGS. 1E-1F). All tested molecules in Table 5 showed better body weight reduction efficacy than Semaglutide. However, Compound 14 exhibited lower BW reduction efficacy compared to Compounds 10 and 13, indicating linker with negative charge may have adverse impact on fusion protein activity.

Example 6: Pharmacokinetic Measurement of Exemplary Fusion Protein Conjugates

Method:

6-8 week old male C57BL/6 mice were administrated in a single subcutaneous dose of 30 nmol/kg of the exemplary fusion protein conjugates (Compounds 4, 9, 10, 19, 63) or the non-acylated fusion protein (i.e., Compound 3, which has the amino acid sequence identical to Compound 2 but without any conjugation) (n=3/group). Plasma samples were collected pre-dose (−5 min), 0.5 hr, 1 hr, 2 hr, 4 hr, 6 hr, 8 hr, 12 hr and 24 hr hours after the injection. For Compound 3, plasma collection timepoints were −5 min, 0.25 h, 0.5 h, 1 h, 2 h, 4 h and 6 h. The concentrations of the fusion protein conjugates or the non-acylated fusion protein in the plasma were measured by an ELISA assay which has immunoreactivities towards both C-terminal FGF21 and intact N-terminal of GLP-1. Based on the graph showing plasma concentration of each protein versus time after subcutaneous injection, the pharmacokinetic parameters were calculated by WinNonlin.

Figure 2:
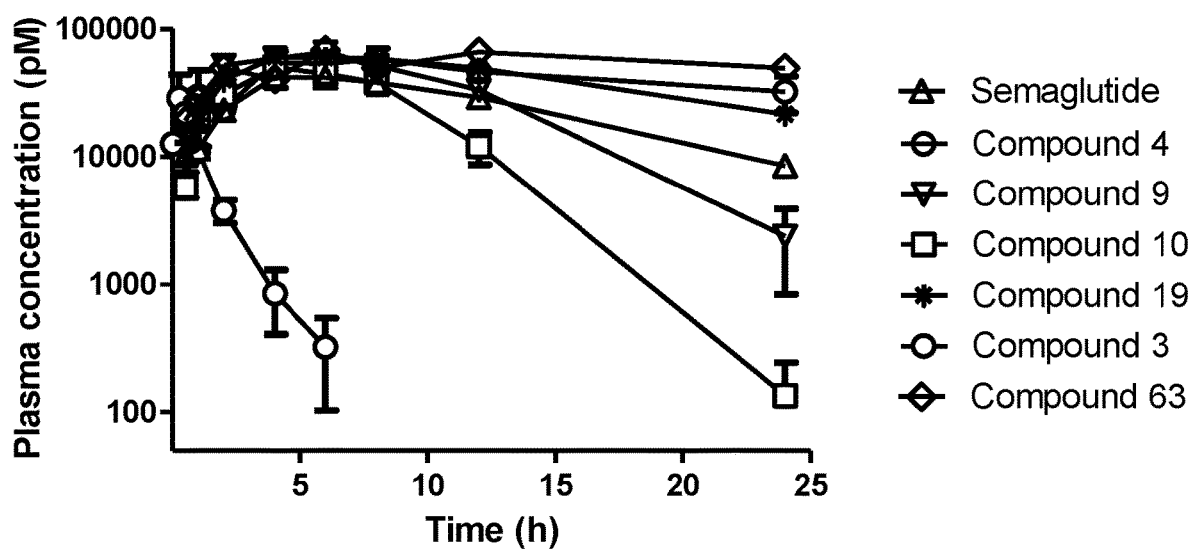
FIG. 2 shows pharmacokinetic measurement of fusion protein conjugates. Each fusion protein conjugate was injected subcutaneously into C57BL/6 mice (n=3/group) once and plasma samples were collected at designed timepoints and analyzed by ELISA method. Plasma concentrations are indicated as mean values and standard error (SEM).

Conclusion:

Acylated fusion protein conjugates including Compounds 4, 9, 10, 19 and 63 showed longer $T_{1/2}$ and larger AUC than non-acylated fusion protein (i.e. Compound 3), suggesting CRM conjugation improved PK profiles. Besides, double acylation significantly prolonged half-lives of protein conjugates compared to monoacylated molecules (double acylated Compounds 4 and 19 compared to monoacylated Compounds 9 and 10). Compounds 4 and 19 also showed better PK properties than Semaglutide (FIG. 2, and Table 4).

TABLE 4

Pharmacokinetic parameters.

| Compound Code | $T_{max}$ (hr) | $C_{max}$ (nmol/L) | Terminal $t_{1/2}$ (hr) | $AUC_{last}$ (hr*nmol/L) |
|---|---|---|---|---|
| Semaglutide (JP51144) | 4 | 43.1 | 7.4 | 614.7 |
| 4 | 8 | 58.3 | 19.7 | 1019.6 |
| 9 | 6 | 65.6 | 3.5 | 791.2 |
| 10 | 4 | 50.2 | 1.9 | 465.1 |
| 19 | 4 | 59.9 | 10.8 | 1018 |
| 3 | 0.5 | 28.9 | 1.1 | 59 |
| 63 | 6.7 | 88.8 | 16.7 | 1294.8 |

Pharmacokinetic data were analyzed by WinNonlin software. Tmax, Cmax, $T_{1/2}$, AUC and MRT were calculated for each molecule.

Example 7. Comparison of GLP-1/FGF21 Fusion Protein Conjugates Against GLP1 Alone and FGF21 Alone Method:

17 week old DIO male C57BL/6 mice (~45 g) were injected everyday subcutaneously with designated proteins (i.e., Compounds 63, 69 and 70) for 21 days. Body weight was measured daily and five animals were used for each treatment group. Day 1 and Day 21 are first day and last day of molecule dosage. % BW loss=100*(BW on Day n-BW on Day 1)/(BW on Day 1). Data are indicated as mean values and standard error (SEM).

Figure 3A:
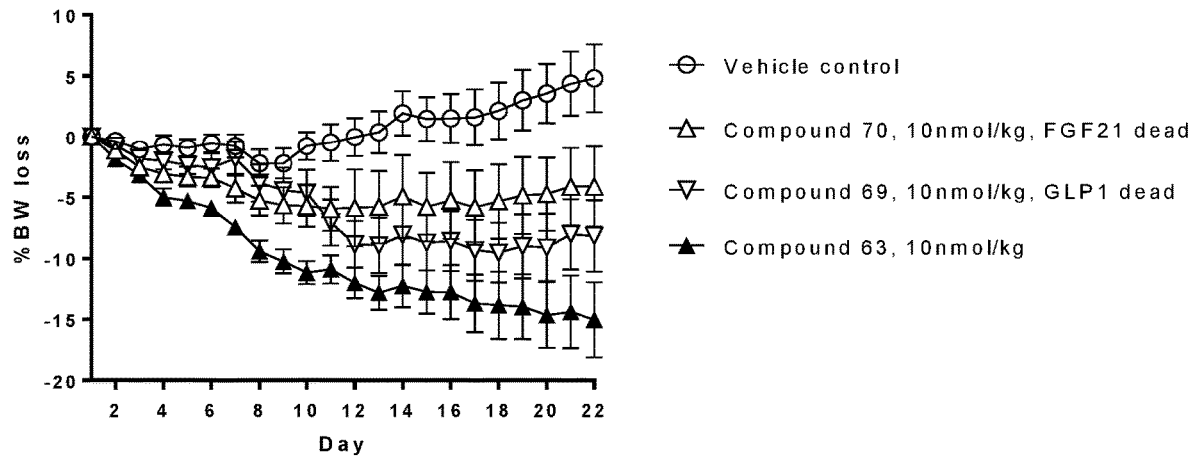
FIGS. 3A-3B show in vivo efficacy in DIO mice. To evaluate the body weight effect of the fusion proteins, 17 week old DIO mice (C57BL/6 mice on high fat diet for 13 weeks) were dosed everyday subcutaneously with different concentrations of compounds for 21 days.
Figure 3B:
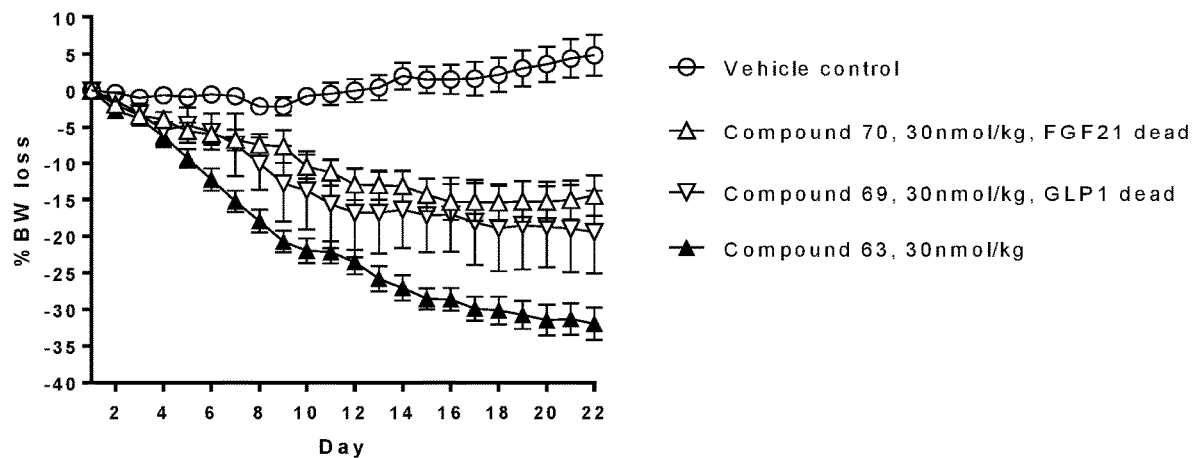
Figure 4A:
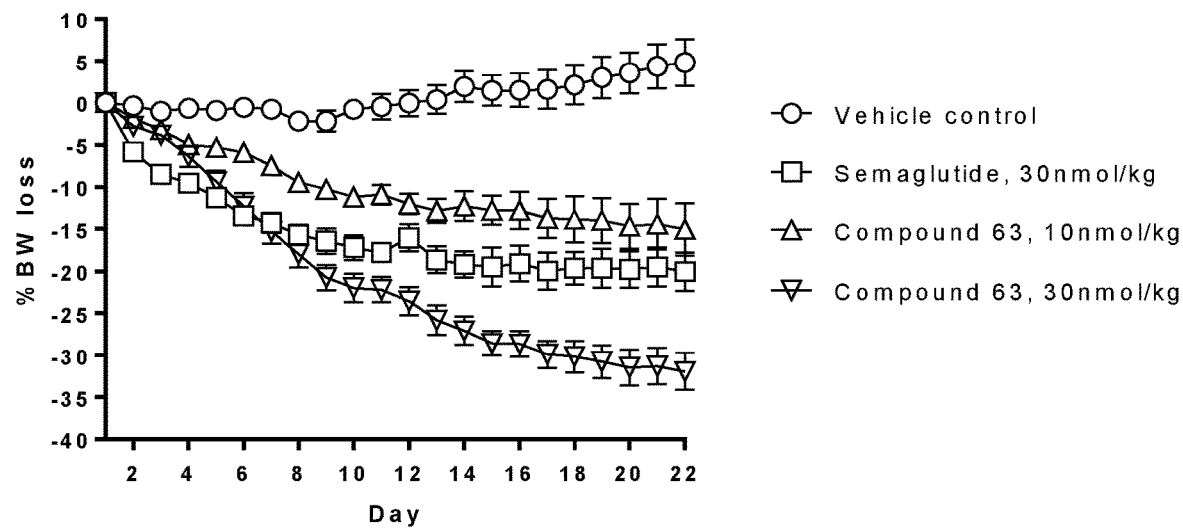
FIGS. 4A-4F show in vivo efficacy in DIO mice. To evaluate effects of the compounds on the body weight, blood glucose, plasma insulin and plasma triglyceride in vivo, 17-week old DIO mice (C57BL/6 mice on high fat diet for 13 weeks) were dosed everyday subcutaneously with different concentrations of compounds for 21 days.
Figure 4B:
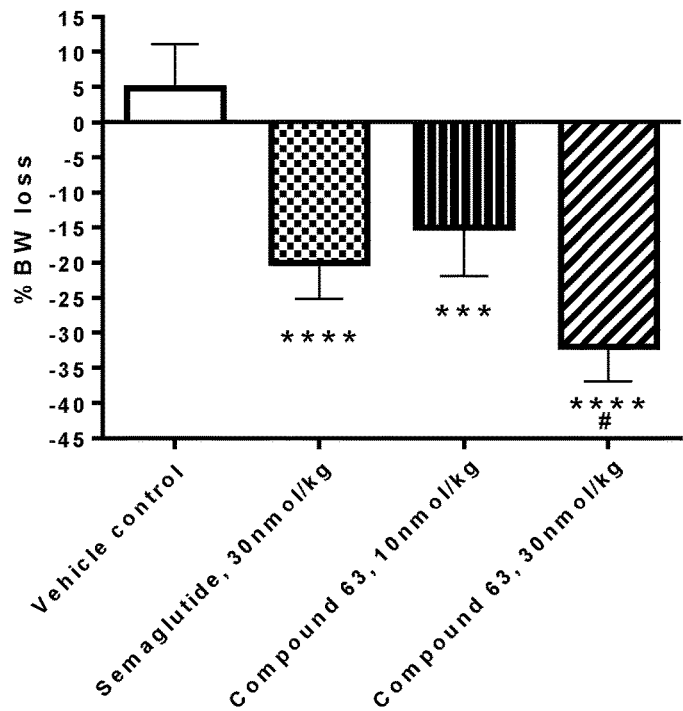
Figure 4C:
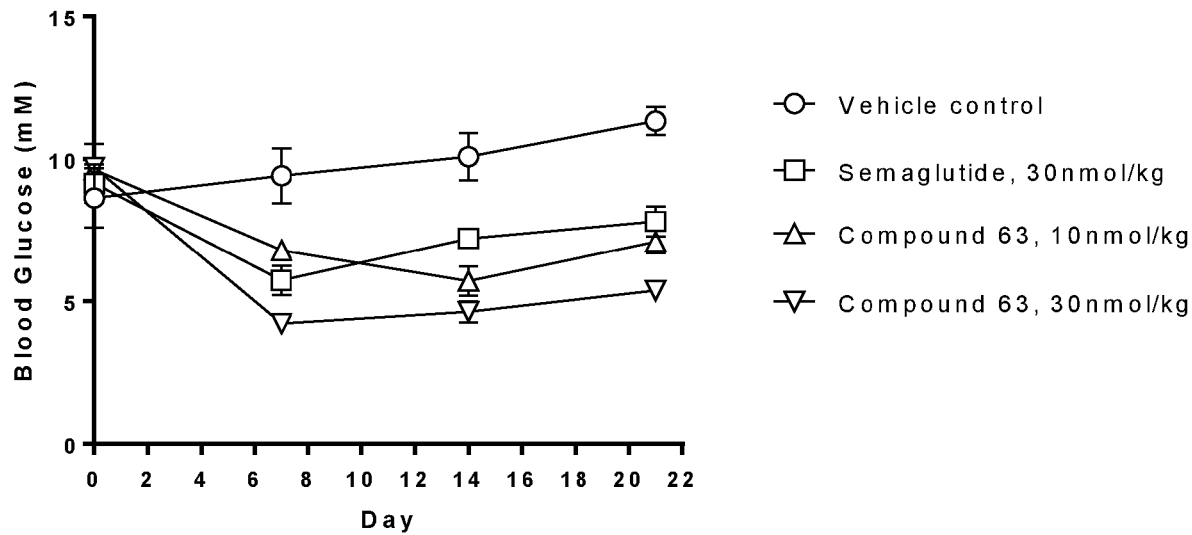
Figure 4D:
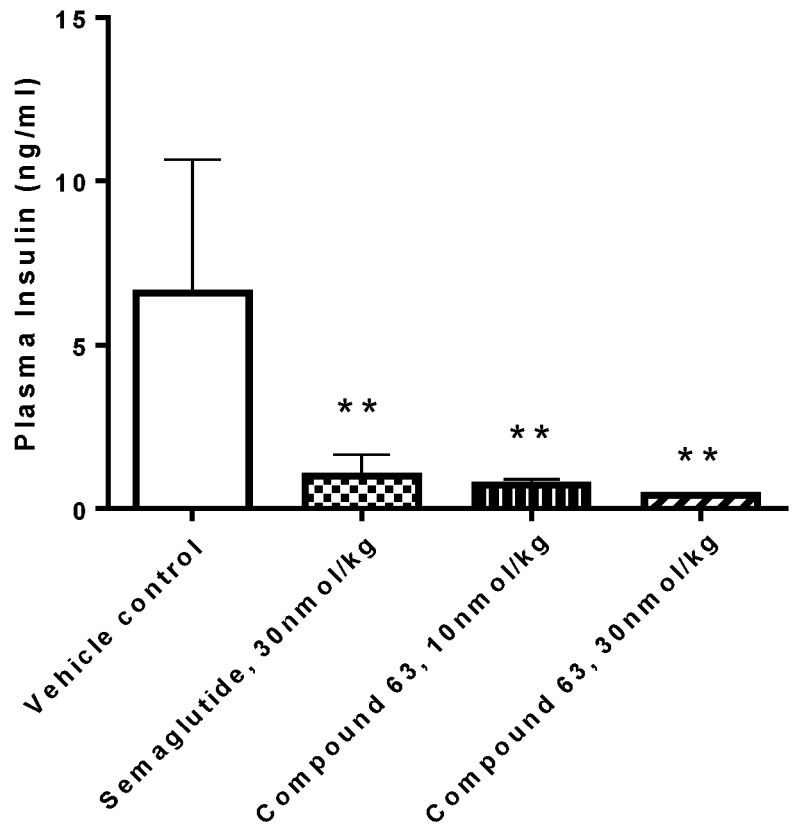
Figure 4E:
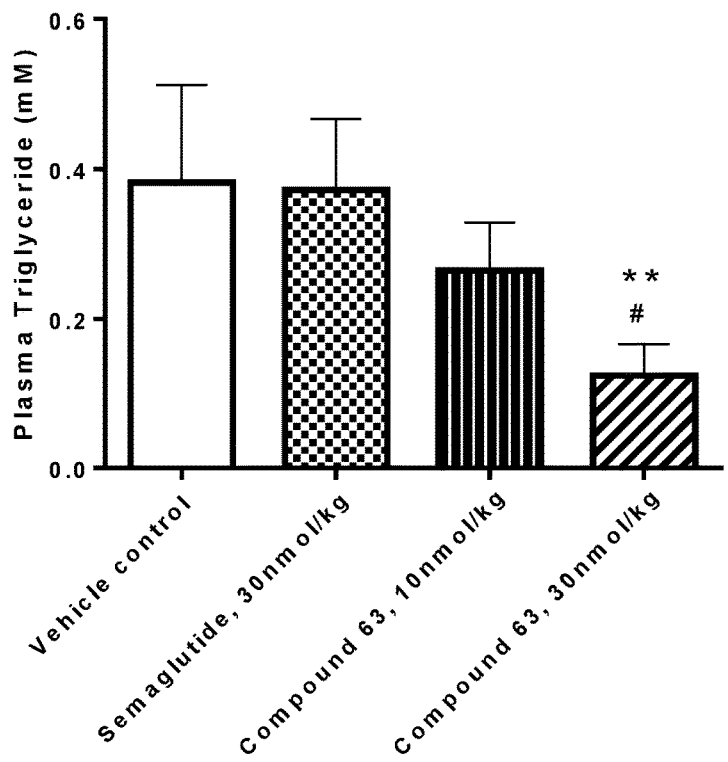
Figure 4F:
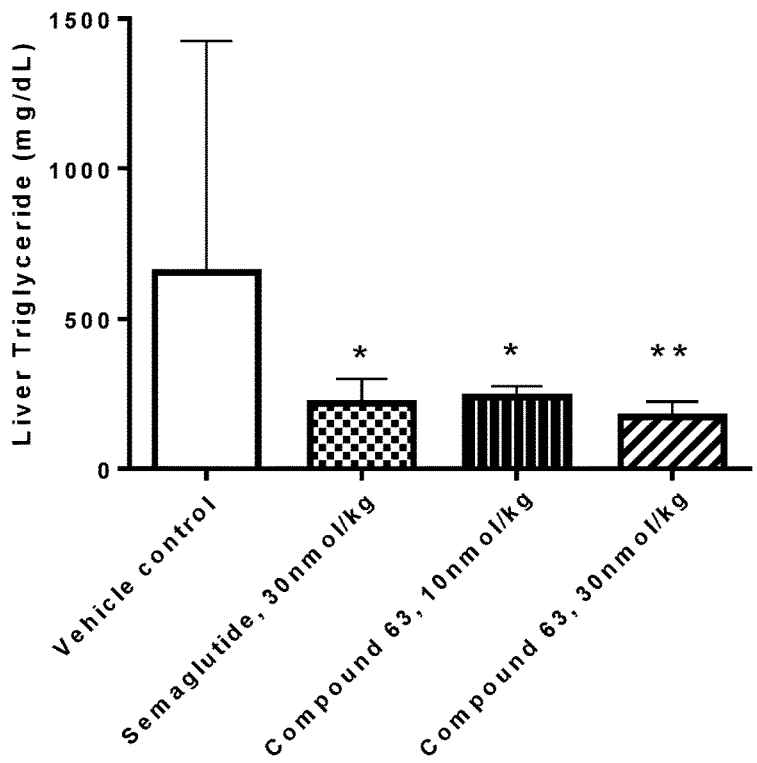

Conclusion:

As shown in FIGS. 3A-3B, Compound 63 at both 10 nmol/kg and 30 nmol/kg showed better body weight control than GLP1 alone (Compound 70) and FGF21 alone (Compound 69), indicating additive or synergistic effect exists when combining GLP1 and FGF21.

Example 8 Efficacy Study in Disease Models

Selected fusion protein conjugates are assessed in disease animal models (DIO mice, db/db mice, NASH model etc.) to determine body weight, food intake, glucose efficacy with dose responses. Some biomarkers are also measured, including fasting insulin, plasma triglyceride, and liver triglyceride.

Method:

17 week old DIO male C57BL/6 mice (~45 g) were injected everyday subcutaneously with designated proteins (i.e., Compound 63) for 21 days. Body weight was measured daily and five animals were used for each treatment group. Fasting glucose was also monitored on designated days. Body weight and glucose were monitored for each individual animal. Day 1 and Day 21 are first day and last day of molecule dosage. % BW loss=100*(BW on Day n-BW on Day 1)/(BW on Day 1). Terminal blood was collected and EDTA-2k plasma was prepared and frozen in −80° C. for biomarker measurement. Livers were also collected and frozen in liquid nitrogen and stored in −80° C.

Data are indicated as mean values and standard error (SEM). Statistical analysis was performed by One-way ANOVA.

Conclusion:

FIGS. 4A-4F showed 30 nmol/kg Compound 63 gave better body weight and glycemic control and lipid profile than 30 nmol/kg Semaglutide. Dose dependent efficacy was also observed when comparing 10 nmol/kg and 30 nmol/kg results.

Example 9: PK Study in Non-Human Primates

Pharmacokinetics of selected fusion protein conjugates are assessed in monkeys, via subcutaneous and intravenous injections, respectively.

Example 10: Stability Study

To test the stability, the different conjugated fusion proteins are formulated in buffers with different compositions (pH6, 7, 7.4 and 8.0) and stored at 4° C. for 2-4 weeks. The % HMWP and % LMW are analyzed by size exclusion chromatography (SEC)-HPLC. The concentration and modifications were analyzed by reverse phase (RP)-UPLC and LC/MS.

Example 11: Immunogenicity Assessment

Selected fusion protein conjugates are also assessed for immunogenicity by in silico (iTope and TCED methods) and ex vivo (EpiScreen) methods.

The invention claimed is:

1. A polypeptide conjugate comprising a fusion polypeptide conjugated to at least one clearance reducing moiety (CRM),
wherein the fusion polypeptide comprises or consists essentially of, from N-terminus to C terminus, a GLP-1, a polypeptide linker and a FGF21;
wherein the GLP-1 comprises no more than 4 substitutions relative to native human GLP-1(7-37) while retaining substantial biological activity of the native human GLP-1(7-37), and comprises one or more substitutions selected from the group consisting of: A8G, K34R, G22E, and R36G, or any combination thereof, wherein the sequence of the native human GLP-1(7-37) is set forth in SEQ ID NO: 50;
wherein the FGF21 comprises a combination of mutations relative to SEQ ID NO: 36 selected from the group consisting of: 1) 121Q, 168L, 171C, 180E; 2) 121Q, 168L, 171G, 174C, 180E; 3) 121Q, 168L, 171G, 180C; 4) 121Q, 168L, 171G, 180E; 5) 71C, 121Q, 168L, 171G, 180E; and 6) 121Q, 168L, 180E, 171G, ins 182C;
wherein the at least one CRM is conjugated to at least one conjugatable residue in the fusion polypeptide; and
wherein the polypeptide linker has a length of at least 4-120 amino acid residues, and
wherein the fusion polypeptide comprises up to two conjugatable residues,
wherein the fusion polypeptide comprises a first conjugatable residue and a second conjugatable residue, wherein: the first conjugatable residue is present in the FGF21 and the second conjugatable residue is present in the polypeptide linker,
wherein both the first and the second conjugatable residues are cysteine; and wherein the conjugatable residue in the polypeptide linker is the most C-terminal residue of the polypeptide linker, or is at least 5 residues away (inclusive of the conjugatable residue) from the most C terminal residue of the GLP-1.

2. The polypeptide conjugate according to claim 1, wherein the conjugatable residue in the FGF21 comprises a substitution selected from the group consisting of: P171C, G174C, A180C, S71C and ins182C relative to SEQ ID NO: 36.

3. The polypeptide conjugate according to claim 1, wherein the FGF21 comprises an amino acid sequence selected from SEQ ID NO: 136-140 and 171.

4. The polypeptide conjugate according to claim 1, wherein the polypeptide linker comprises one or more units of a repeating sequence, and the repeating sequence comprises no negatively charged amino acid residues.

5. The polypeptide conjugate according to claim 1, wherein the conjugatable residue in the polypeptide linker is cysteine and the polypeptide linker comprises an amino acid sequence selected from the group consisting of SEQ ID NO: 122-132.

6. The polypeptide conjugate according to claim 1, wherein the CRM comprises a structure of *-A-B-C-D-E, and wherein:

A is selected from a bond,

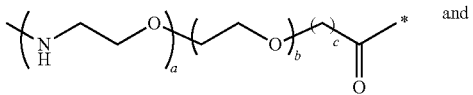

-continued

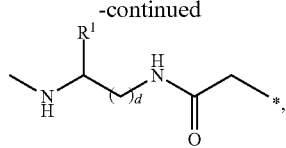

a, b, c and d are independently an integer from 0 to 4, $R^1$ is hydrogen or —COOH;

B is selected from a bond,

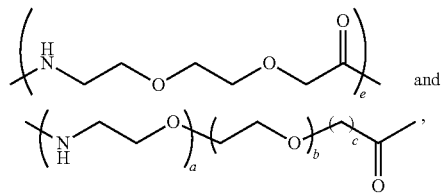

e is an integer from 1 to 4,
C is a bond or

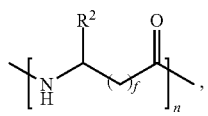

$R^2$ is —CH$_2$SO$_3$H or —COOH, f is an integer from 1 to 4, n is an integer from 1 to 25;

D is selected from a bond,

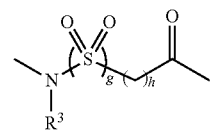 and 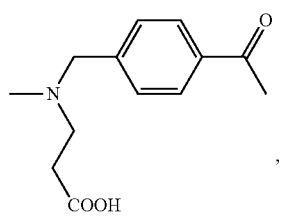, g and h are independently 0 or 1, and $R^3$ is H or —CH$_2$COOH;

E is an acidic group having a formula:

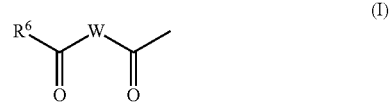

(I)

wherein W represents —(CR$^4$R$^5$)$_l$—, $R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, $R^6$ is selected from hydroxyl or NR$^7$R$^8$;

$R^7$ and $R^8$ are independently selected from the group consisting of hydrogen, alkyl, hydroxyl, and

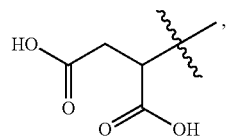

and l is an integer from 10 to 20, or a pharmaceutically acceptable salt thereof.

7. The polypeptide conjugate according to claim 6, wherein the CRM is conjugated to at least one cysteine residue in the fusion polypeptide, and wherein the CRM comprises the structure of below formula:

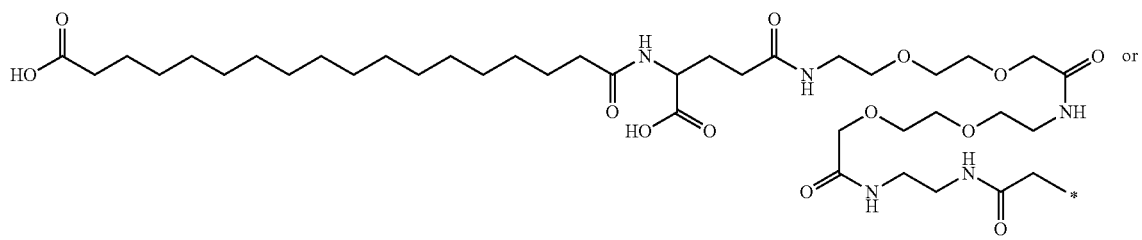 or

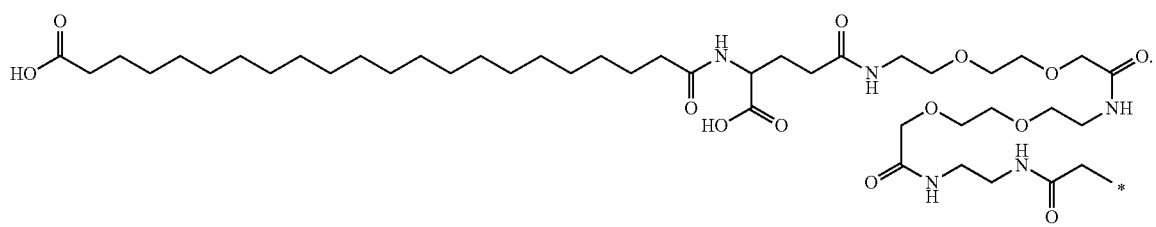

8. The polypeptide conjugate according to claim 1, wherein the polypeptide conjugate comprises a fusion polypeptide conjugated to a first CRM and a second CRM, and wherein the fusion polypeptide comprising an amino acid sequence of SEQ ID NO: X, and the first and the second CRMs that are covalently attached respectively to the $p^{th}$ and the $q^{th}$ residues counting in a direction from N terminus to C terminus in the fusion polypeptide, with one CRM attached to one residue, wherein the $p^{th}$ residue is cysteine (pC) and the $q^{th}$ residue is cysteine (qC), and wherein:

1) X is 148, p is 51, pC is 51C, q is 222, qC is 222C,
2) X is 149, p is 51, pC is 51C, q is 225, qC is 225C,
3) X is 150, p is 51, pC is 51C, q is 233, qC is 233C,
4) X is 151, p is 51, pC is 51C, q is 231, qC is 231C,
5) X is 152, p is 51, pC is 51C, q is 222, qC is 222C,
6) X is 153, p is 51, pC is 51C, q is 225, qC is 225C,
7) X is 154, p is 51, pC is 51C, q is 231, qC is 231C,
8) X is 155, p is 55, pC is 55C, q is 229, qC is 229C,
9) X is 156, p is 59, pC is 59C, q is 233, qC is 233C,
10) X is 157, p is 51, pC is 51C, q is 225, qC is 225C,
11) X is 158, p is 46, pC is 46C, q is 225, qC is 225C,
12) X is 159, p is 41, pC is 41C, q is 225, qC is 225C,
13) X is 160, p is 51, pC is 51C, q is 222, qC is 222C,
14) X is 161, p is 46, pC is 46C, q is 222, qC is 222C,
15) X is 162, p is 41, pC is 41C, q is 222, qC is 222C,
16) X is 163, p is 51, pC is 51C, q is 225, qC is 225C,
17) X is 164, p is 46, pC is 46C, q is 235, qC is 235C,
18) X is 165, p is 51, pC is 51C, q is 222, qC is 222C,
19) X is 168, p is 52, pC is 52C, q is 282, qC is 282C,
20) X is 169, p is 62, pC is 62C, q is 282, qC is 282C,
21) X is 170, p is 42, pC is 42C, q is 282, qC is 282C, or
22) X is 1, p is 51, pC is 51C, q is 122, qC is 122C, and wherein the CRM has the structure of below formula:

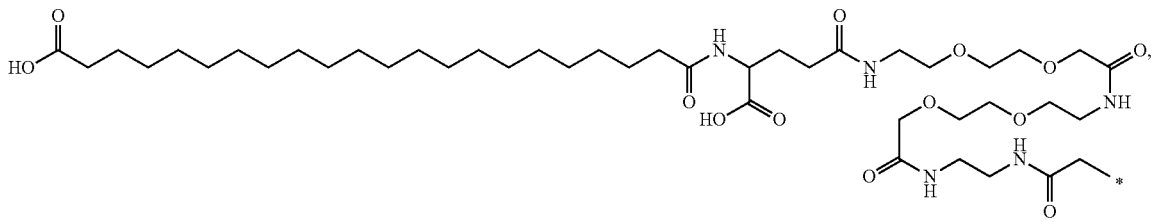 [SMILES: CCC(=O)NCCNC(=O)COCCOCCNC(=O)COCCOCCNC(=O)CCC(NC(=O)CCCCCCCCCCCCCCCCCCCCC(=O)O)C(=O)O]

or a pharmaceutically acceptable salt thereof.

9. The polypeptide conjugate of claim 1, wherein the GLP-1 comprises the amino acid sequence of SEQ ID NO: 52 or SEQ ID NO: 120.

10. The polypeptide conjugate of claim 1, wherein the fusion polypeptide comprises an amino acid sequence selected from the group consisting of: SEQ ID NO: 1, 148-165, and 168-170.

11. A pharmaceutical composition comprising the polypeptide conjugate according to claim 1 and a pharmaceutically acceptable carrier.

12. A polynucleotide that encodes the fusion polypeptide as defined in claim 1.

13. A vector comprising the polynucleotide according to claim 12.

14. A host cell comprising the vector according to claim 13.

15. A method of treating a metabolic disorder in a subject in need thereof, comprising administering a therapeutically effective amount of the polypeptide conjugate according to claim 1, wherein the treating does not include preventing or curing.

16. The method of claim 15, wherein the metabolic disorder is diabetes, obesity, non-alcoholic steatohepatitis (NASH), dyslipidaemia, arteriosclerosis, alcoholic steatohepatitis (ASH), diabetic nephropathy, gestational diabetes, metabolic syndrome X, nonalcoholic fatty liver disease (NAFLD), end-stage liver disease, hepatic steatosis (fatty liver), liver cirrhosis, or primary biliary cirrhosis (PBC).

* * * * *